US008506577B2

(12) United States Patent
Tanaka et al.

(10) Patent No.: US 8,506,577 B2
(45) Date of Patent: *Aug. 13, 2013

(54) TWO-PHASE SURGICAL PROCEDURE FOR CREATING A PNEUMOSTOMA TO TREAT CHRONIC OBSTRUCTIVE PULMONARY DISEASE

(75) Inventors: Don Tanaka, Saratoga, CA (US);
Joshua P. Wiesman, Boston, MA (US);
David C. Plough, Portola Valley, CA (US)

(73) Assignee: Portaero, Inc., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/543,588

(22) Filed: Jul. 6, 2012

(65) Prior Publication Data

US 2012/0277584 A1 Nov. 1, 2012

Related U.S. Application Data

(63) Continuation of application No. 12/388,435, filed on Feb. 18, 2009, now abandoned.

(60) Provisional application No. 61/029,830, filed on Feb. 19, 2008, provisional application No. 61/032,877, filed on Feb. 29, 2008, provisional application No. 61/038,371, filed on Mar. 20, 2008, provisional application No. 61/082,892, filed on Jul. 23, 2008, provisional application No. 61/083,573, filed on Jul. 25, 2008, provisional application No. 61/084,559, filed on Jul. 29, 2008, provisional application No. 61/088,118, filed on Aug. 12, 2008, provisional application No. 61/143,298, filed on Jan. 8, 2009, provisional application No. 61/151,581, filed on Feb. 11, 2009.

(51) Int. Cl.
| *A61F 11/00* | (2006.01) |
| *A61M 31/00* | (2006.01) |
| *A61M 37/00* | (2006.01) |
| *A61M 25/00* | (2006.01) |
| *A61M 5/178* | (2006.01) |
| *A61M 15/00* | (2006.01) |
| *A61M 16/00* | (2006.01) |
| *A62B 7/00* | (2006.01) |
| *A62B 9/00* | (2006.01) |
| *A62B 18/00* | (2006.01) |

(52) U.S. Cl.
USPC ... 606/108; 604/93.01; 604/264; 604/164.04; 128/200.24

(58) Field of Classification Search
USPC .................. 128/898, 200.24, 200.26, 204.18, 128/207.14–207.17; 604/44–45, 93.01, 96.01, 604/99.03, 102.01–102.03, 174, 180, 288.01, 604/540–541, 23–26, 27–28, 264, 164.04; 606/108

See application file for complete search history.

(56) References Cited

U.S. PATENT DOCUMENTS

| 733,152 A | 7/1903 | Chisholm |
| 953,922 A | 4/1910 | Rogers |

(Continued)

FOREIGN PATENT DOCUMENTS

| EP | 0260543 A1 | 3/1988 |
| EP | 1358904 | 5/2003 |

(Continued)

OTHER PUBLICATIONS

Sahn, Steven A. "Talc Should be Used for Pleurodesis." American Journal of Respiratory and Critical Care Medicine 163(2001 ): 2023-2024.*

(Continued)

*Primary Examiner* — Andrew Iwamaye
(74) *Attorney, Agent, or Firm* — Fliesler Meyer LLP

(57) ABSTRACT

A two-phase surgical procedure is disclosed for creating a pneumostoma to treat chronic obstructive pulmonary disease The first phase is a procedure to induce creation of a localized pleurodesis and is preferably performed as an outpatient procedure. The second phase is a procedure to introduce a surgical instrument into the lung via the pleurodesis to create the pneumostoma. An interval of about one of more days between the first and second phases allows the formation of a stable pleurodesis to prevent pneumothorax during the procedure.

15 Claims, 33 Drawing Sheets

(56) References Cited

U.S. PATENT DOCUMENTS

| | | |
|---|---|---|
| 2,206,687 A | 7/1940 | Bloomheart |
| 2,867,213 A | 1/1959 | Thomas, Jr. |
| 2,873,742 A | 2/1959 | Shelden |
| 2,991,787 A | 7/1961 | Shelden et al. |
| 3,253,594 A | 5/1966 | Matthews et al. |
| 3,294,355 A | 12/1966 | Topf |
| 3,384,087 A | 5/1968 | Brummelkamp |
| 3,463,159 A | 8/1969 | Heimlich |
| 3,511,243 A | 5/1970 | Toy |
| 3,556,103 A | 1/1971 | Calhoun et al. |
| 3,638,649 A | 2/1972 | Ersek |
| 3,682,166 A | 8/1972 | Jacobs |
| 3,688,773 A | 9/1972 | Weiss |
| 3,707,146 A | 12/1972 | Cook et al. |
| 3,766,920 A | 10/1973 | Greene |
| 3,777,757 A | 12/1973 | Gray et al. |
| 3,788,326 A | 1/1974 | Jacobs |
| 3,817,250 A | 6/1974 | Weiss et al. |
| 3,908,704 A | 9/1975 | Clement et al. |
| 3,916,903 A | 11/1975 | Pozzi |
| 4,153,058 A | 5/1979 | Nehme |
| 4,291,694 A | 9/1981 | Chai |
| 4,439,189 A | 3/1984 | Sargeant et al. |
| 4,465,062 A | 8/1984 | Versaggi et al. |
| 4,502,482 A | 3/1985 | DeLuccia et al. |
| 4,583,977 A | 4/1986 | Shishov et al. |
| 4,664,660 A | 5/1987 | Goldberg et al. |
| 4,705,039 A | 11/1987 | Sakaguchi et al. |
| 4,799,494 A | 1/1989 | Wang |
| 4,813,929 A | 3/1989 | Semrad |
| 4,826,495 A | 5/1989 | Petersen |
| 4,828,553 A | 5/1989 | Nielsen |
| 4,869,717 A | 9/1989 | Adair |
| 4,872,869 A | 10/1989 | Johns |
| 4,889,534 A | 12/1989 | Mohiuddin et al. |
| 4,905,694 A | 3/1990 | Will |
| 4,931,045 A | 6/1990 | Steer |
| 4,944,724 A | 7/1990 | Goldberg et al. |
| 4,959,054 A | 9/1990 | Heimke et al. |
| 4,976,688 A | 12/1990 | Rosenblum |
| 5,004,456 A | 4/1991 | Botterbusch et al. |
| 5,060,645 A | 10/1991 | Russell |
| 5,073,169 A | 12/1991 | Raiken |
| 5,078,689 A | 1/1992 | Keller |
| 5,137,509 A | 8/1992 | Freitas |
| 5,139,485 A | 8/1992 | Smith et al. |
| 5,141,516 A | 8/1992 | Detweiler |
| 5,218,957 A | 6/1993 | Strickland |
| 5,230,332 A | 7/1993 | Strickland |
| 5,230,350 A | 7/1993 | Fentress |
| 5,245,995 A | 9/1993 | Sullivan et al. |
| 5,261,708 A | 11/1993 | Steer |
| 5,263,939 A | 11/1993 | Wortrich |
| 5,312,331 A | 5/1994 | Knoepfler |
| 5,315,992 A | 5/1994 | Dalton |
| 5,318,523 A | 6/1994 | Lu |
| 5,336,206 A | 8/1994 | Shichman |
| 5,344,410 A | 9/1994 | Kolkin et al. |
| 5,354,283 A | 10/1994 | Bark et al. |
| 5,356,386 A | 10/1994 | Goldberg et al. |
| 5,366,478 A | 11/1994 | Brinkerhoff et al. |
| 5,370,625 A | 12/1994 | Shichman |
| 5,376,376 A | 12/1994 | Li |
| 5,389,077 A | 2/1995 | Melinyshyn et al. |
| 5,401,262 A | 3/1995 | Karwoski et al. |
| 5,403,264 A | 4/1995 | Wohlers et al. |
| 5,407,433 A | 4/1995 | Loomas |
| 5,431,633 A | 7/1995 | Fury |
| 5,478,333 A | 12/1995 | Asherman, Jr. |
| 5,484,401 A | 1/1996 | Rodriguez et al. |
| 5,496,297 A | 3/1996 | Olsen |
| 5,501,677 A | 3/1996 | Jensen |
| 5,501,678 A | 3/1996 | Olsen |
| 5,588,424 A | 12/1996 | Insler et al. |
| 5,616,131 A | 4/1997 | Sauer et al. |
| 5,660,175 A | 8/1997 | Dayal |
| 5,662,629 A | 9/1997 | Steer et al. |
| 5,728,066 A | 3/1998 | Daneshvar |
| 5,730,735 A | 3/1998 | Holmberg et al. |
| 5,738,661 A | 4/1998 | Larice |
| 5,807,341 A | 9/1998 | Heim |
| 5,817,113 A | 10/1998 | Gifford, III et al. |
| 5,830,200 A | 11/1998 | Steer et al. |
| 5,843,053 A | 12/1998 | Steer |
| 5,897,531 A | 4/1999 | Amirana |
| 5,931,821 A | 8/1999 | Weilbacher et al. |
| 5,954,636 A | 9/1999 | Schwartz et al. |
| 5,961,090 A | 10/1999 | Parkin |
| 5,971,962 A | 10/1999 | Kojima et al. |
| 5,972,026 A | 10/1999 | Laufer et al. |
| 5,991,980 A | 11/1999 | Meager |
| 6,056,744 A | 5/2000 | Edwards |
| 6,059,816 A | 5/2000 | Moenning |
| 6,083,255 A | 7/2000 | Laufer et al. |
| 6,174,323 B1 | 1/2001 | Biggs et al. |
| 6,197,010 B1 | 3/2001 | Leise, Jr. et al. |
| 6,200,333 B1 | 3/2001 | Laufer |
| 6,258,100 B1 | 7/2001 | Alferness et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,293,930 B1 | 9/2001 | Brunsgaard et al. |
| 6,293,951 B1 | 9/2001 | Alferness et al. |
| 6,299,633 B1 | 10/2001 | Laufer |
| 6,322,536 B1 | 11/2001 | Rosengart et al. |
| 6,328,689 B1 | 12/2001 | Gonzalez et al. |
| 6,330,882 B1 | 12/2001 | French |
| 6,334,441 B1 | 1/2002 | Zowtiak et al. |
| 6,358,269 B1 | 3/2002 | Aye |
| 6,398,775 B1 | 6/2002 | Perkins et al. |
| 6,402,754 B1 | 6/2002 | Gonzalez |
| 6,411,852 B1 | 6/2002 | Danek et al. |
| 6,416,554 B1 | 7/2002 | Alferness et al. |
| 6,432,100 B1 | 8/2002 | Affeld |
| 6,443,156 B1 | 9/2002 | Niklason et al. |
| 6,468,292 B1 | 10/2002 | Mollenauer et al. |
| 6,485,407 B2 | 11/2002 | Alferness et al. |
| 6,488,673 B1 | 12/2002 | Laufer et al. |
| 6,491,706 B1 | 12/2002 | Alferness et al. |
| 6,514,290 B1 | 2/2003 | Loomas |
| 6,517,519 B1 | 2/2003 | Rosen et al. |
| 6,520,183 B2 | 2/2003 | Amar |
| 6,527,761 B1 | 3/2003 | Soltesz et al. |
| 6,550,475 B1 | 4/2003 | Oldfield |
| 6,569,121 B1 | 5/2003 | Purow et al. |
| 6,569,166 B2 | 5/2003 | Gonzalez |
| 6,585,639 B1 | 7/2003 | Kotmel et al. |
| 6,589,161 B2 | 7/2003 | Corcoran |
| 6,592,594 B2 | 7/2003 | Rimbaugh et al. |
| 6,599,311 B1 | 7/2003 | Biggs et al. |
| 6,609,521 B1 | 8/2003 | Belani et al. |
| 6,629,951 B2 | 10/2003 | Laufer et al. |
| 6,632,239 B2 | 10/2003 | Snyder et al. |
| 6,632,243 B1 | 10/2003 | Zadno-Azizi et al. |
| 6,634,360 B1 | 10/2003 | Flodin |
| 6,634,363 B1 | 10/2003 | Danek et al. |
| 6,638,253 B2 | 10/2003 | Breznock |
| 6,653,525 B2 | 11/2003 | Ingenito et al. |
| 6,659,961 B2 | 12/2003 | Robinson |
| 6,679,264 B1 | 1/2004 | Deem et al. |
| 6,682,506 B1 | 1/2004 | Navarro |
| 6,692,494 B1 | 2/2004 | Cooper et al. |
| 6,694,979 B2 | 2/2004 | Deem et al. |
| 6,695,791 B2 | 2/2004 | Gonzalez |
| 6,709,401 B2 | 3/2004 | Perkins et al. |
| 6,712,812 B2 | 3/2004 | Roschak et al. |
| 6,726,598 B1 | 4/2004 | Jarvis et al. |
| 6,736,797 B1 | 5/2004 | Larsen et al. |
| 6,749,606 B2 | 6/2004 | Keast et al. |
| 6,770,063 B2 | 8/2004 | Goldberg et al. |
| 6,770,070 B1 | 8/2004 | Balbierz |
| 6,790,172 B2 | 9/2004 | Alferness et al. |
| 6,827,086 B2 | 12/2004 | Shuman |

| | | | | | | |
|---|---|---|---|---|---|---|
| 6,837,906 B2 | 1/2005 | Ginn | | 2003/0127090 A1 | 7/2003 | Gifford et al. |
| 6,840,243 B2 | 1/2005 | Deem et al. | | 2003/0130593 A1 | 7/2003 | Gonzalez |
| 6,843,767 B2 | 1/2005 | Corcoran et al. | | 2003/0149446 A1 | 8/2003 | Shuman |
| 6,846,292 B2 | 1/2005 | Bakry | | 2003/0154576 A1 | 8/2003 | Mirharooni |
| 6,849,061 B2 | 2/2005 | Wagner | | 2003/0154988 A1 | 8/2003 | DeVore et al. |
| 6,852,108 B2 | 2/2005 | Barry et al. | | 2003/0158515 A1 | 8/2003 | Gonzalez et al. |
| 6,860,847 B2 | 3/2005 | Alferness et al. | | 2003/0163024 A1 | 8/2003 | Corcoran |
| 6,878,141 B1 | 4/2005 | Perkins et al. | | 2003/0181356 A1 | 9/2003 | Ingenito |
| 6,886,558 B2 | 5/2005 | Tanaka | | 2003/0181922 A1 | 9/2003 | Alferness |
| 6,901,927 B2 | 6/2005 | Deem et al. | | 2003/0183235 A1 | 10/2003 | Rimbaugh et al. |
| 6,904,909 B2 | 6/2005 | Andreas et al. | | 2003/0186904 A1 | 10/2003 | Ruben et al. |
| 6,905,518 B2 | 6/2005 | Ginn | | 2003/0195385 A1 | 10/2003 | DeVore |
| 6,916,310 B2 | 7/2005 | Sommerich | | 2003/0195511 A1 | 10/2003 | Barry |
| 6,929,637 B2 | 8/2005 | Gonzalez et al. | | 2003/0212337 A1 | 11/2003 | Sirokman |
| 6,941,950 B2 | 9/2005 | Wilson et al. | | 2003/0212412 A1 | 11/2003 | Dillard et al. |
| 6,997,189 B2 | 2/2006 | Biggs et al. | | 2003/0216730 A1 | 11/2003 | Barry et al. |
| 6,997,918 B2 | 2/2006 | Soltesz et al. | | 2003/0216769 A1 | 11/2003 | Dillard et al. |
| 7,011,094 B2 | 3/2006 | Rapacki et al. | | 2003/0228344 A1 | 12/2003 | Fields et al. |
| 7,011,314 B2 | 3/2006 | McFarlane | | 2003/0233099 A1 | 12/2003 | Danaek et al. |
| 7,014,628 B2 | 3/2006 | Bousquet | | 2004/0010209 A1 | 1/2004 | Sirokman |
| 7,022,088 B2 | 4/2006 | Keast et al. | | 2004/0010289 A1 | 1/2004 | Biggs et al. |
| 7,033,387 B2 | 4/2006 | Zadno-Azizi et al. | | 2004/0016435 A1 | 1/2004 | Deem et al. |
| 7,036,509 B2 | 5/2006 | Rapacki et al. | | 2004/0024356 A1 | 2/2004 | Tanaka |
| 7,086,398 B2 | 8/2006 | Tanaka | | 2004/0031494 A1 | 2/2004 | Danek et al. |
| 7,100,616 B2 | 9/2006 | Springmeyer | | 2004/0040555 A1 | 3/2004 | Tanaka |
| 7,135,010 B2 | 11/2006 | Buckman et al. | | 2004/0047855 A1 | 3/2004 | Ingenito |
| 7,141,046 B2 | 11/2006 | Perkins et al. | | 2004/0055606 A1 | 3/2004 | Hendricksen et al. |
| 7,165,548 B2 | 1/2007 | Deem et al. | | 2004/0059263 A1 | 3/2004 | DeVore et al. |
| 7,172,581 B2 | 2/2007 | Ciok et al. | | 2004/0073155 A1 | 4/2004 | Laufer et al. |
| 7,175,644 B2 | 2/2007 | Cooper et al. | | 2004/0073191 A1 | 4/2004 | Soltesz et al. |
| 7,182,772 B2 | 2/2007 | Alferness et al. | | 2004/0073201 A1 | 4/2004 | Cooper et al. |
| 7,186,259 B2 | 3/2007 | Perkins et al. | | 2004/0073241 A1 | 4/2004 | Barry et al. |
| 7,192,420 B2 | 3/2007 | Whiteford | | 2004/0078026 A1 | 4/2004 | Wagner |
| 7,195,016 B2 | 3/2007 | Loyd et al. | | 2004/0078054 A1 | 4/2004 | Biggs et al. |
| 7,195,017 B2 | 3/2007 | Tanaka | | 2004/0087831 A1 | 5/2004 | Michels et al. |
| 7,207,946 B2 | 4/2007 | Sirokman | | 2004/0097983 A1 | 5/2004 | Snyder et al. |
| 7,232,414 B2 | 6/2007 | Gonzalez | | 2004/0143282 A1 | 7/2004 | Dillard et al. |
| 7,244,245 B2 | 7/2007 | Purow et al. | | 2004/0144387 A1 | 7/2004 | Amar |
| 7,252,086 B2 | 8/2007 | Tanaka | | 2004/0158228 A1 | 8/2004 | Perkins et al. |
| 7,377,278 B2 | 5/2008 | Tanaka | | 2004/0167636 A1 | 8/2004 | Dillard et al. |
| 7,383,740 B2 | 6/2008 | Krasilchikov et al. | | 2004/0173218 A1 | 9/2004 | Yamada et al. |
| 7,398,782 B2 | 7/2008 | Tanaka | | 2004/0199128 A1 | 10/2004 | Morris et al. |
| 7,406,963 B2 | 8/2008 | Chang et al. | | 2004/0200484 A1 | 10/2004 | Springmeyer |
| 7,422,584 B2 | 9/2008 | Loomas et al. | | 2004/0206349 A1 | 10/2004 | Alferness et al. |
| 7,426,929 B2 | 9/2008 | Tanaka | | 2004/0210248 A1 | 10/2004 | Gordon et al. |
| 7,533,667 B2 | 5/2009 | Tanaka | | 2004/0211412 A1 | 10/2004 | Alferness et al. |
| 7,594,914 B2 | 9/2009 | Luchetti | | 2004/0211434 A1* | 10/2004 | Loomas et al. ............... 128/898 |
| 7,682,332 B2 | 3/2010 | Tanaka | | 2004/0220446 A1 | 11/2004 | Corcoran et al. |
| 7,753,052 B2 | 7/2010 | Tanaka | | 2004/0220556 A1 | 11/2004 | Cooper et al. |
| 7,789,083 B2 | 9/2010 | Tanaka | | 2004/0225254 A1 | 11/2004 | Tanaka et al. |
| 7,811,274 B2 | 10/2010 | Tanaka | | 2004/0231674 A1* | 11/2004 | Tanaka ................... 128/207.14 |
| 7,824,366 B2 | 11/2010 | Tanaka | | 2004/0237966 A1 | 12/2004 | Tanaka |
| 7,828,789 B2 | 11/2010 | Tanaka | | 2004/0243140 A1 | 12/2004 | Alferness et al. |
| 7,896,008 B2 | 3/2011 | Tanaka | | 2004/0244802 A1 | 12/2004 | Tanaka |
| 7,909,803 B2 | 3/2011 | Tanaka | | 2004/0244803 A1 | 12/2004 | Tanaka |
| 8,252,003 B2* | 8/2012 | Tanaka et al. ............... 606/108 | | 2005/0005936 A1 | 1/2005 | Wondka |
| 2001/0025132 A1 | 9/2001 | Alferness et al. | | 2005/0015106 A1 | 1/2005 | Perkins et al. |
| 2001/0041906 A1 | 11/2001 | Gonzalez | | 2005/0022809 A1 | 2/2005 | Wondka |
| 2001/0041932 A1 | 11/2001 | Scholz et al. | | 2005/0025816 A1 | 2/2005 | Tanaka |
| 2002/0042564 A1 | 4/2002 | Cooper et al. | | 2005/0033310 A1 | 2/2005 | Alferness et al. |
| 2002/0062120 A1 | 5/2002 | Perkins et al. | | 2005/0033344 A1 | 2/2005 | Dillard et al. |
| 2002/0077593 A1 | 6/2002 | Perkins et al. | | 2005/0043745 A1 | 2/2005 | Alferness et al. |
| 2002/0087153 A1 | 7/2002 | Roschak et al. | | 2005/0043751 A1 | 2/2005 | Phan et al. |
| 2002/0111619 A1 | 8/2002 | Keast et al. | | 2005/0043752 A1 | 2/2005 | Phan et al. |
| 2002/0111620 A1 | 8/2002 | Cooper et al. | | 2005/0049615 A1 | 3/2005 | Cooper et al. |
| 2002/0112729 A1 | 8/2002 | DeVore et al. | | 2005/0056292 A1 | 3/2005 | Cooper |
| 2002/0120177 A1 | 8/2002 | Borst et al. | | 2005/0060041 A1 | 3/2005 | Phan et al. |
| 2002/0165618 A1 | 11/2002 | Ingenito et al. | | 2005/0060042 A1 | 3/2005 | Phan et al. |
| 2002/0188171 A1 | 12/2002 | Alferness et al. | | 2005/0060044 A1 | 3/2005 | Roschak et al. |
| 2003/0013935 A1 | 1/2003 | Alferness et al. | | 2005/0061322 A1 | 3/2005 | Freitag |
| 2003/0018344 A1 | 1/2003 | Kaji et al. | | 2005/0066976 A1 | 3/2005 | Wondka |
| 2003/0050648 A1 | 3/2003 | Alferness et al. | | 2005/0085801 A1 | 4/2005 | Cooper et al. |
| 2003/0051733 A1 | 3/2003 | Kotmel et al. | | 2005/0096529 A1 | 5/2005 | Cooper et al. |
| 2003/0055331 A1 | 3/2003 | Kotmel et al. | | 2005/0103340 A1 | 5/2005 | Wondka |
| 2003/0065339 A1 | 4/2003 | Snyder et al. | | 2005/0107783 A1 | 5/2005 | Tom et al. |
| 2003/0069488 A1 | 4/2003 | Alferness et al. | | 2005/0131276 A1 | 6/2005 | Alferness et al. |
| 2003/0078469 A1 | 4/2003 | Corcoran | | 2005/0137518 A1 | 6/2005 | Biggs et al. |
| 2003/0083542 A1 | 5/2003 | Alferness et al. | | 2005/0137611 A1 | 6/2005 | Escudero et al. |
| 2003/0083671 A1 | 5/2003 | Rimbaugh et al. | | 2005/0137712 A1 | 6/2005 | Biggs et al. |

| | | |
|---|---|---|
| 2005/0137715 A1 | 6/2005 | Phan et al. |
| 2005/0145253 A1 | 7/2005 | Wilson et al. |
| 2005/0161040 A1 | 7/2005 | Tanaka |
| 2005/0166925 A1 | 8/2005 | Wilson et al. |
| 2005/0171396 A1 | 8/2005 | Pankratov et al. |
| 2005/0177144 A1 | 8/2005 | Phan et al. |
| 2005/0178385 A1 | 8/2005 | Dellaca' et al. |
| 2005/0178389 A1 | 8/2005 | Shaw et al. |
| 2005/0192526 A1 | 9/2005 | Biggs et al. |
| 2005/0203483 A1 | 9/2005 | Perkins et al. |
| 2005/0205097 A1 | 9/2005 | Kyle |
| 2005/0244401 A1 | 11/2005 | Ingenito |
| 2005/0281797 A1 | 12/2005 | Gong et al. |
| 2005/0281801 A1 | 12/2005 | Gong et al. |
| 2005/0281802 A1 | 12/2005 | Gong et al. |
| 2005/0282748 A1 | 12/2005 | Gong et al. |
| 2005/0288549 A1 | 12/2005 | Mathis |
| 2005/0288550 A1 | 12/2005 | Mathis |
| 2005/0288684 A1 | 12/2005 | Aronson et al. |
| 2005/0288702 A1 | 12/2005 | McGurk et al. |
| 2006/0004400 A1 | 1/2006 | McGurk et al. |
| 2006/0009748 A1 | 1/2006 | Mathis |
| 2006/0025815 A1 | 2/2006 | McGurk et al. |
| 2006/0047291 A1 | 3/2006 | Barry |
| 2006/0076023 A1 | 4/2006 | Rapacki et al. |
| 2006/0079838 A1 | 4/2006 | Walker et al. |
| 2006/0079845 A1* | 4/2006 | Howard et al. ............... 604/175 |
| 2006/0095002 A1 | 5/2006 | Soltesz et al. |
| 2006/0107961 A1 | 5/2006 | Tanaka |
| 2006/0116749 A1 | 6/2006 | Willink et al. |
| 2006/0118125 A1 | 6/2006 | Tanaka |
| 2006/0118126 A1 | 6/2006 | Tanaka |
| 2006/0124126 A1 | 6/2006 | Tanaka |
| 2006/0130830 A1 | 6/2006 | Barry |
| 2006/0135947 A1 | 6/2006 | Soltesz et al. |
| 2006/0135984 A1 | 6/2006 | Kramer et al. |
| 2006/0142672 A1 | 6/2006 | Keast et al. |
| 2006/0161233 A1 | 7/2006 | Barry et al. |
| 2006/0162731 A1 | 7/2006 | Wondka et al. |
| 2006/0206147 A1 | 9/2006 | DeVore et al. |
| 2006/0212046 A1 | 9/2006 | Pearce et al. |
| 2006/0212051 A1 | 9/2006 | Snyder et al. |
| 2006/0235432 A1 | 10/2006 | DeVore et al. |
| 2006/0235467 A1 | 10/2006 | DeVore |
| 2006/0264772 A1 | 11/2006 | Aljuri et al. |
| 2006/0276807 A1 | 12/2006 | Keast et al. |
| 2006/0280772 A1 | 12/2006 | Roschak et al. |
| 2006/0280773 A1 | 12/2006 | Roschak et al. |
| 2006/0283462 A1 | 12/2006 | Fields et al. |
| 2007/0005083 A1 | 1/2007 | Sabanathan et al. |
| 2007/0027434 A1 | 2/2007 | Pedersen et al. |
| 2007/0038177 A1 | 2/2007 | Sinha et al. |
| 2007/0043350 A1 | 2/2007 | Soltesz et al. |
| 2007/0051372 A1 | 3/2007 | Tanaka |
| 2007/0055175 A1 | 3/2007 | Caro |
| 2007/0088300 A1 | 4/2007 | Cline et al. |
| 2007/0123922 A1 | 5/2007 | Cooper et al. |
| 2007/0128174 A1 | 6/2007 | Kleinsek et al. |
| 2007/0142742 A1 | 6/2007 | Aljuri et al. |
| 2007/0163598 A1 | 7/2007 | Chang et al. |
| 2007/0179426 A1 | 8/2007 | Selden |
| 2007/0185531 A1 | 8/2007 | Rimbaugh et al. |
| 2007/0186932 A1 | 8/2007 | Wondka et al. |
| 2007/0186933 A1 | 8/2007 | Domingo et al. |
| 2007/0299424 A1 | 12/2007 | Cumming et al. |
| 2008/0281151 A1 | 11/2008 | Chang et al. |
| 2008/0281295 A1 | 11/2008 | Chang et al. |
| 2008/0281433 A1 | 11/2008 | Chang et al. |
| 2008/0283065 A1 | 11/2008 | Chang et al. |
| 2008/0287878 A1 | 11/2008 | Tanaka |
| 2008/0287973 A1 | 11/2008 | Aster et al. |
| 2008/0295829 A1 | 12/2008 | Evens |
| 2009/0205641 A1 | 8/2009 | Tanaka |
| 2009/0205643 A1 | 8/2009 | Tanaka et al. |
| 2009/0205644 A1 | 8/2009 | Tanaka et al. |
| 2009/0205645 A1 | 8/2009 | Tanaka et al. |
| 2009/0205646 A1 | 8/2009 | Tanaka et al. |
| 2009/0205647 A1 | 8/2009 | Plough et al. |
| 2009/0205648 A1 | 8/2009 | Tanaka et al. |
| 2009/0205649 A1 | 8/2009 | Tanaka et al. |
| 2009/0205650 A1 | 8/2009 | Tanaka et al. |
| 2009/0205651 A1 | 8/2009 | Tanaka et al. |
| 2009/0205658 A1 | 8/2009 | Tanaka et al. |
| 2009/0205665 A1 | 8/2009 | Tanaka et al. |
| 2009/0209856 A1 | 8/2009 | Tanaka et al. |
| 2009/0209906 A1 | 8/2009 | Tanaka et al. |
| 2009/0209909 A1 | 8/2009 | Tanaka et al. |
| 2009/0209917 A1 | 8/2009 | Tanaka et al. |
| 2009/0209924 A1 | 8/2009 | Tanaka |
| 2009/0209936 A1 | 8/2009 | Tanaka et al. |
| 2009/0209970 A1 | 8/2009 | Tanaka et al. |
| 2009/0209971 A1 | 8/2009 | Tanaka et al. |
| 2010/0170507 A1 | 7/2010 | Tanaka et al. |
| 2010/0204707 A1* | 8/2010 | Tanaka et al. ............... 606/108 |
| 2010/0286544 A1 | 11/2010 | Tanaka et al. |

FOREIGN PATENT DOCUMENTS

| | | |
|---|---|---|
| EP | 1658867 | 5/2006 |
| EP | 1757322 A1 * | 2/2007 |
| EP | 1815821 | 8/2007 |
| JP | 62-202847 U | 6/1986 |
| JP | 2000197706 | 7/2000 |
| RU | 2192185 | 10/2002 |
| WO | WO96/39960 | 12/1996 |
| WO | WO99/66975 | 12/1999 |
| WO | WO00/76577 A1 | 12/2000 |
| WO | WO01/45568 A1 | 6/2001 |
| WO | WO02/04054 | 1/2002 |
| WO | WO2005070480 | 8/2005 |

OTHER PUBLICATIONS

Rockey, Edward Ernest. "Tube Pneumonostomy for Thoracotomy Reject Crippling Bullous Emphysema". New York State Journal of Medicine (1973): 664-671.*

Sugarmann et al. "Mesh inseration as an aid for pleurodesis". J. Cardiovasc Surgery 37 (1996): 173-175.*

Stewart et al. "Decompression of Giant Bulla in Acute Pneumonia: Surgical Palliation Prior to Definitive Management". Ann Thoac Surg 82 (2006): 2308-2309.*

MacArthur et al., "Intracavity suction and drainage in the treatment of emphysematous bullae", Thorax 1977; 32, 668-672.

Sahn, Steven A., "Talc Should be Used for Pleurodesis", American Journal of Respiratory and Critical Care Medicine 2001; 163, 2023-2024.

Sugarmann et al., "Mesh insertion as an aid for pleurodesis", Journal of Cardiovascular Surgery 1996; 37 (Suppl. 1 to No. 6):173-5.

Swallow et al., "Quadriceps strength predicts mortality in patients with moderate to severe chronic obstructive pulmonary disease", Thorax 2007; 62: 115-120.

Symbas et al., "Nontuberculous Pleural Empyema in Adults, The Role of a Modified Eloesser Procedure in Its Management", The Annals of Thoracic Surgery 1971; 12: 69-78.

Takizawa et al., "Computed tomography-guided drainage for large pulmonary bullae", Interactive Cardiovascular and Thoracic Surgery 2004; 3: 283-285.

Terry et al., "Collateral Ventilation in Man", The New England Journal of Medicine 1978; 298(1): 10-15.

Thourani et al., "Twenty-six Years of Experience With the Modified Eloesser Flap", Ann Thorac Surg 2003; 76: 401-406.

Toma et al., "Brave new world for interventional bronchoscopy", Thorax 2005; 60: 180-181.

Ugama et al., "Drainage of Giant Bulla with Balloon Catheter Using Chemical Irritant and Fibrin Glue", Chest 1988; 94(6): 1289-1290.

Vainrub et al., "Percutaneous Drainage of Lung Abscess", American Review of Respiratory Disease 1978; 117: 153-160.

Venn et al., "Intracavity drainage for Bulbous, emphysematous lung disease: experience with the Brompton technique", Thorax 1988; 43: 998-1002.

Wood et al., "A multicenter trial of an intrabronchial valve for treatment of severe emphysema", The Journal of Thoracic and Cardiovascular Surgery 2007; 133: 65-73.e2.

Woodring et al., "Pneumothorax ex vacuo", Chest 1996, 110: 1102-1124.

Woolcock et al., "Mechanical factors influencing collateral ventilation in human, dog, and pig lungs", Journal of Applied Physiology 1971; 30: 99-115.

Yellin et al., "Percutaneous Tube Drainage: The Treatment of Choice for Refractory Lung Abscess", The Annals of Thoracic Surgery 1985; 39: 266-270.

Yim et al., "Minimally invasive thoracic surgery: where do we stand now?" Hong Kong Medical Journal 1995; 1: 115-122.

Yim et al., "Early results of endoscopic lung volume reduction for emphysema", The Journal of Thoracic and Cardiovascular Surgery 2004; 127: 1564-1573.

International Search Report for PCT/US/2009/034374 dated Aug. 28, 2009; 13 pages.

International Search Report for PCT/US/2009/034380 dated Sep. 24, 2009; 12 pages.

International Search Report for PCT/US2009/034322 dated Oct. 5, 2009; 14 pages.

International Search Report for PCT/US2009/034406 dated Dec. 2, 2009; 16 pages.

Extended European Search Report dated Jun. 22, 2011 for PCT/US2009034374, 7 pages.

Extended European Search Report dated Jun. 15, 2011 for PCT/US2009034322, 7 pages.

Aljuri et al., "Validation and pilot clinical study of a new bronchoscopic method to measure collateral ventilation before endobronchial lung volume reduction", J Appl Physio 106: 774-783, 2009.

Al-Salem et al., "Computed tomography-guided percutaneous needle aspiration of lung abscesses in neonates and children", Pediatr Surg Int (1997) 12: 417-419, copyright Springer-Verlag 1997.

Ball, Jr et al., "Percutaneous Drainage of Chest Abscesses in Children", Radiology 1989; 171: 431-434.

Becker et al., "Lung Volumes before and after Lung Volume Reduction Surgery: Quantitative CT Analysis", Am J Respir Crit Care Med 1998; 157: 1593-1599.

Brenner et al., "Innovative Approaches to Lung Volume Reduction for Emphysema", Chest 2004; 126: 238-248.

Brutinel et al., "A two-year experience with the neodymium-YAG laser in endobronchial obstruction", Chest 1987; 91: 159-165.

Celli et al. "Standards for the diagnosis and treatment of patients with COPD: a summary of the ATS/ERS position paper", European Respiratory Journal 2004; 23; 932-946.

Cetti et al., "Collateral ventilation", Thorax 2006; 61: 371-373.

Chino et al., "Ventilation of Excised Human Lungs Via Spiracles through the Pleura", Thematic Poster Session (Abstract p. A546) Session: 12:45 pm-4:15 pm, May 2003, Mechanics of the Lung and Respiratory System.

Choong et al., "Feasibility and safety of airway bypass stent placement and influence of topical mitomycin C on stent patency", The Journal of Thoracic and Cardiovascular Surgery 2005; 129: 632-638.

Choong et al., "Transpleural ventilation of explanted human lungs", Thorax 2007; 62: 623-630; originally published online Apr. 5, 2007.

Cope, J. Hallam, "Monaldi Procedure", Presented at the annual meeting of the California Tuberculosis and Health Association and the California Trudeau Society, Mar. 30-Apr. 1, 1950, San Diego; retrieved from California Medicine Dec. 1950; vol. 73, No. 6: 563-564.

Dumon, J. F., "A Dedicated Tracheobronchial Stent", Chest 1990; 97: 328-332.

Eloesser, "An Operation for Tuberculous Empyema", Chest 1935; 1: 8-23.

Fein, Alan M, "Lung Volume Reduction Surgery: Answering the Crucial Questions", Chest 1998; 113: 277-282.

Fernandes et al., "*Airway Hyperresponsiveness: From Molecules to Bedside Invited Review*: Do inflammatory mediators influence the contribution of airway smooth muscle contraction to airway hyperresponsiveness in asthma?", Journal Appl Physiol 2003; 95; 844-853.

Fessler, Henry E., "Collateral Ventilation, the Bane of Bronchoscopic Volume Reduction", Am J Respir Crit Care Med 2005; 171: 423-425.

Frawley et al., "Airway Pressure Release Ventilation: Theory and Practice", AACN Clinical Issues 2001; vol. 12, No. 2: 234-246.

Freitag et al., "Theoretical and experimental basis for the development of a dynamic airway stent", European Respiratory Journal 1994; 7: 2038-2045.

Ghaye et al., "Imaging guided thoracic interventions", European Respiratory Journal 2001; 17: 507-528.

Golding et al., "External drainage of large bullae in severe generalized emphysema", Journal of Thoracic and Cardiovascular Surgery Jun. 1968; vol. 55, No. 6: 891-894.

Goldstraw et al., "The Surgical Treatment of Emphysema: The Brompton Approach", Chest Surgery Clinics of North America Nov. 1995; vol. 5, No. 4: 777-797.

Habashi, Nader M., "Other approaches to open-lung ventilation: Airway pressure release ventilation", Crit Care Med 2005, vol. 33, No. 3 (Suppl): S228-S240.

Harada et al., "Re-expansion of Refractory Atelectasis Using a Bronchofiberscope with a Balloon Cuff", Chest 1983; 84: 725-728.

Head et al., "Intracavitary Suction (Monaldi) in the Treatment of Emphysematous Bullae and Blebs", Journal of Thoracic Surgery Dec. 1949; vol. 18, No. 6: 761-776.

Heimlich, Henry J., "Respiratory Rehabilitation with Transtracheal Oxygen System", Ann Otol Rhinol Laryngol Nov./Dec. 1982; 91: 643-647.

Hogg et al., "Chronic obstructive pulmonary disease c2: Pathology and biochemistry of emphysema", Thorax 2002; 57: 830-834.

Hogg et al., "The Resistance of Collateral Channels in Excised Human Lungs", Journal of Clinical Investigation 1969; 48: 421-431.

Joannette, Albert, "Drainage of Tuberculous Cavities by Aspiration (Monaldi Method)", The Canadian Medical Association Journal Jan. 1941; 46-48.

Korpela et al., "Bioabsorbable Self-reinforced Poly-L-Lactide, Metallic, and Silicone Stents in the Management of Experimental Tracheal Stenosis", Chest 1999; 115: 490-495.

Lausberg et al., "Bronchial Fenestration Improves Expiratory Flow in Emphysematous Human Lungs", Annals of Thoracic Surgery 2003; 75: 393-398.

Lorenzo et al., "Lung Abscesses in Children: Diagnostic and Therapeutic Needle Aspiration", Radiology Oct. 1985; 157: 79-80.

MacArthur et al., "Intracavity suction and drainage in the treatment of emphysematous bullae", Thorax 1977; 32: 668-672.

Macklem, Peter T., "Collateral Ventilation", The New England Journal of Medicine Jan. 5, 1978; 298(1): 49-50.

Matson et al., "Evaluation of Various Surgical Procedures in the Treatment of Pulmonary Tuberculosis", Chest 1946; 12: 40-47.

McCoy, Robert, "Oxygen-Conserving Techniques and Devices", Respiratory Care Jan. 2000, vol. 45, No. 1: 95-104.

Meyers et al., "Chronic obstructive pulmonary disease 10: Bullectomy, lung volume reduction surgery, and transplantation for patients with chronic obstructive pulmonary disease", Thorax 2003; 58: 634-638.

Mineo et al., "Awake Nonresectional Lung Volume Reduction Surgery", Annals of Surgery 2006; 243: 131-136.

Monaldi, V., "Endocavitary Aspiration: Its Practical Application", Tubercle 1947: 223-228.

Monaldi, V., "Endocavitary Aspiration in the Treatment of Lung Abscess", Chest 1956; 29: 193-201.

Monaldi, V., "Endocavitary Aspiration in the Treatment of Pathological Cavities of the Lung", Proceedings of the International Conference on Tuberculosis, Scandinavian Journal of Respiratory Diseases Supplementum 1968; 65: 113-121.

Moore et al., "Unilateral Extrapulmonary Airway Bypass in Advanced Emphysema", The Annals of Thoracic Surgery 2010; 89:899-906.

U.S. Department of Health and Human Services; National Institutes of Health National Heart, Lung, and Blood Institute; "Chronic Obstructive Pulmonary Disease", NIH Publication No. 03-5229 Mar. 2003: 1-6.

Parker et al., "Percutaneous small bore catheter drainage in the management of lung abscesses", Chest 1987; 92: 213-218.

Petty, Thomas L., "The history of COPD", International Journal of COPD 2006; 1(1): 3-14.

Polkey, M. J., "Surgical procedures in emphysema: any impact on dynamic hyperinflation?" European Respiratory Review 2006; 15(100): 96-98.

Polkey, M. J., "Bronchoscopic lung volume reduction", European Respiratory Review 2006; 15(100): 99-103.

Rendina et al., "Feasibility and safety of the airway bypass procedure for patients with emphysema", The Journal of Thoracic and Cardiovascular Surgery 2003; 125: 1294-1299.

Rockey, Edward E., "Tube Pneumonostomy for Thoracotomy Reject Crippling Bulbous Emphysema", New York State Journal of Medicine Mar. 1, 1973: 664-671.

Rousseau et al., "Self-expandable Prostheses in the Tracheobronchial Tree", Thoracic Radiology 1993; 188: 199-203.

Russi et al., "Lung volume reduction surgery: what can we learn from the National Emphysema Treatment Trial?" European Respiratory Journal 2003; 22: 571-573.

Saad et al., "Surgical treatment of bullae for Bulbous emphysema: a simple drainage", J. Pneumologia 2000; 26(3): 1-11, retrieved from <http://www.scielo.br/scielo.php?script=arttext&pid=S0102-35862000000300003&Ing=e . . . > May 2, 2007.

Shah, Pallav, "Surgical and Non-surgical Volume Reduction for COPD", Presented at the Clinical Consensus on COPD, Mar. 2-3, 2007, Novotel London West, 56 pages; see p. 55 of 56.

Shah et al., "Surgical Treatment of Bulbous Emphysema: Experience with the Brompton Technique", Annals of Thoracic Surgery 1994; 58: 1452-1456.

Shim et al., "Percutaneous Drainage of Lung Abscess", Lung 1990; 168: 201-207.

Snell et al., "The Potential for Bronchoscopic Lung Volume Reduction Using Bronchial Prosteses: A Pilot Study", Chest 2003; 124: 1073-1080.

Snell, Gregory I., "Airway Bypass Stenting for Severe Emphysema", retrieved from <http://www.ctsnet.org/sections/thoracic/newtechnology/article-4.html>, Aug. 6, 2007, 4 pages.

Springmeyer, Steven C., "Development of a Bronchial Valve for Treatment of Severe Emphysema", retrieved from <http://www.ctsnet.org/sections/thoracic/newtechnology/article-10.html>, Jul. 16, 2007, 6 pages.

Stewart et al., "Decompression of Giant Bulla in Acute Pneumonia: Surgical Palliation Prior to Definitive Management", Ann Thoracic Surg 2006; 82: 2308-2309.

* cited by examiner

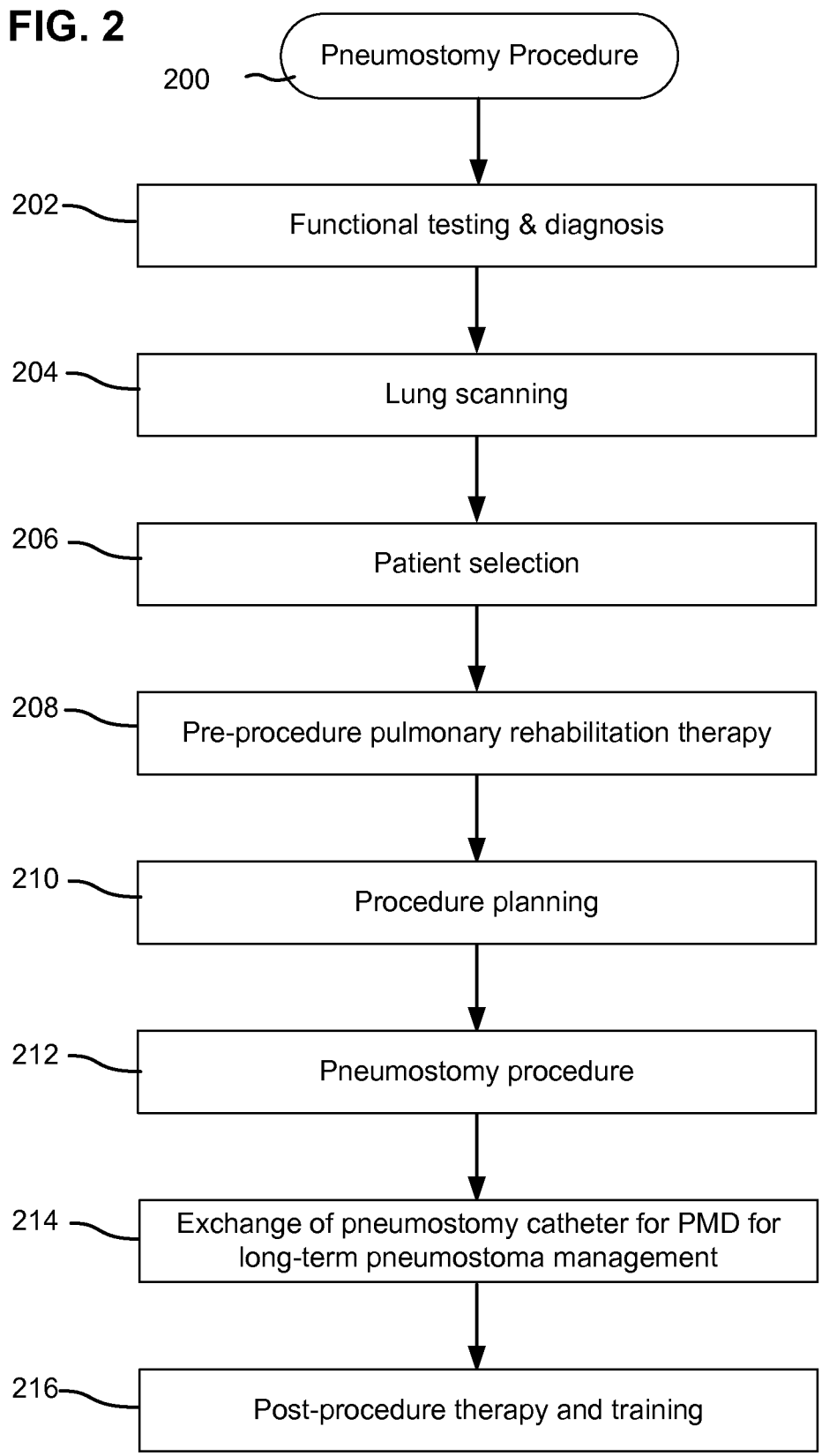

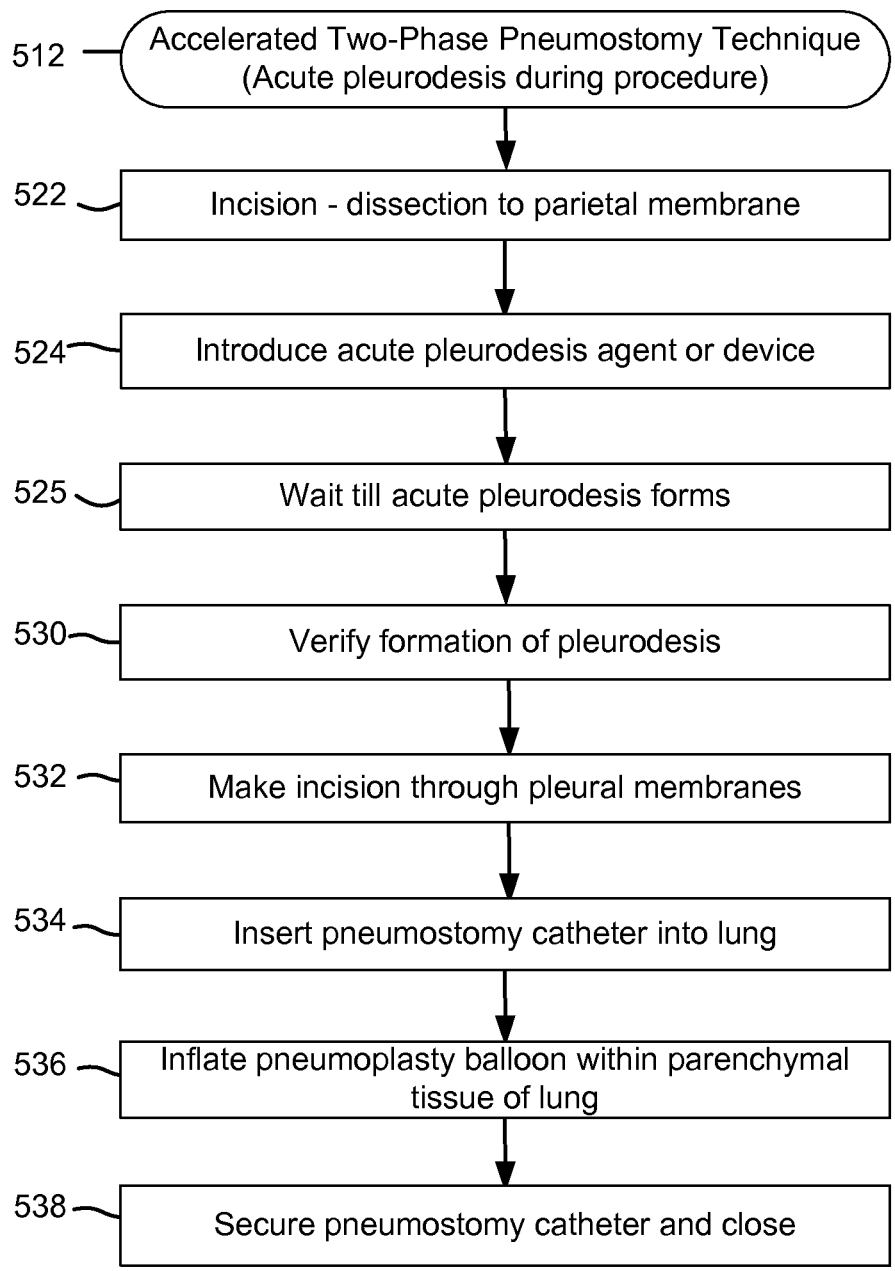

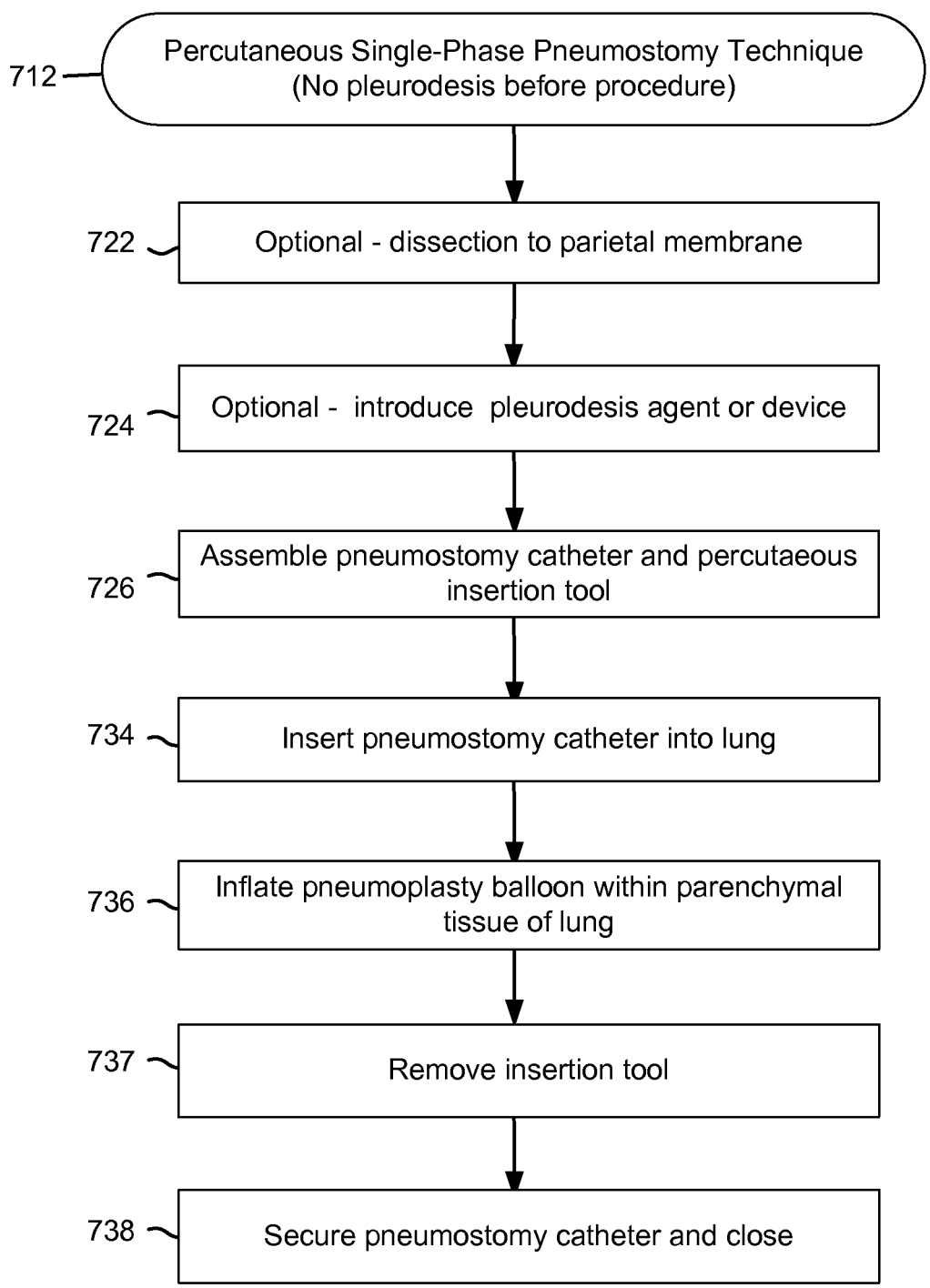

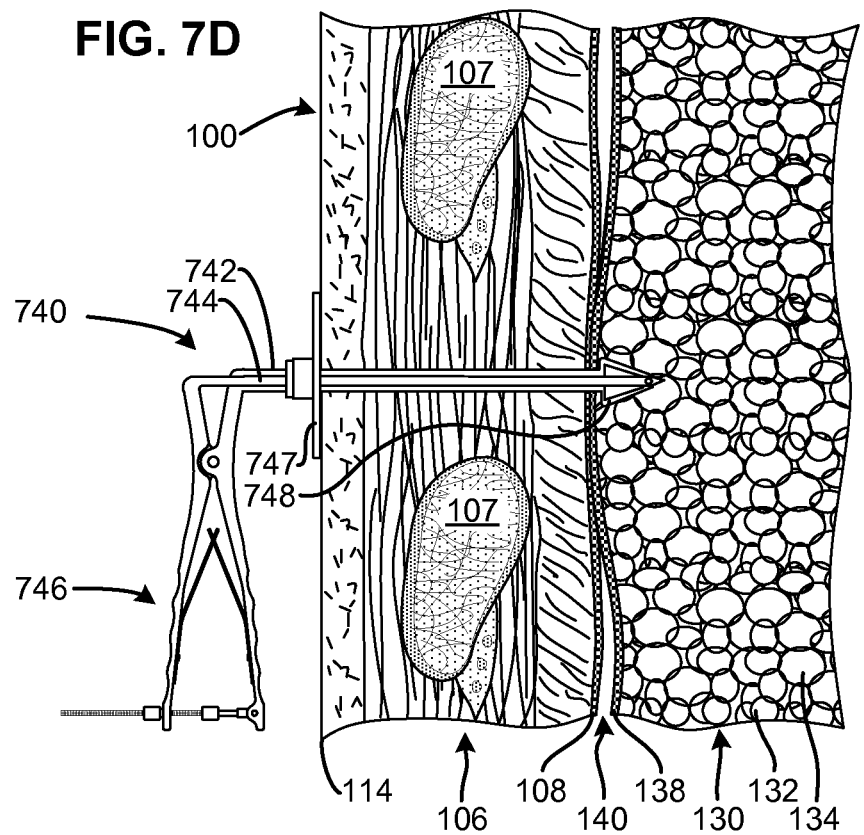
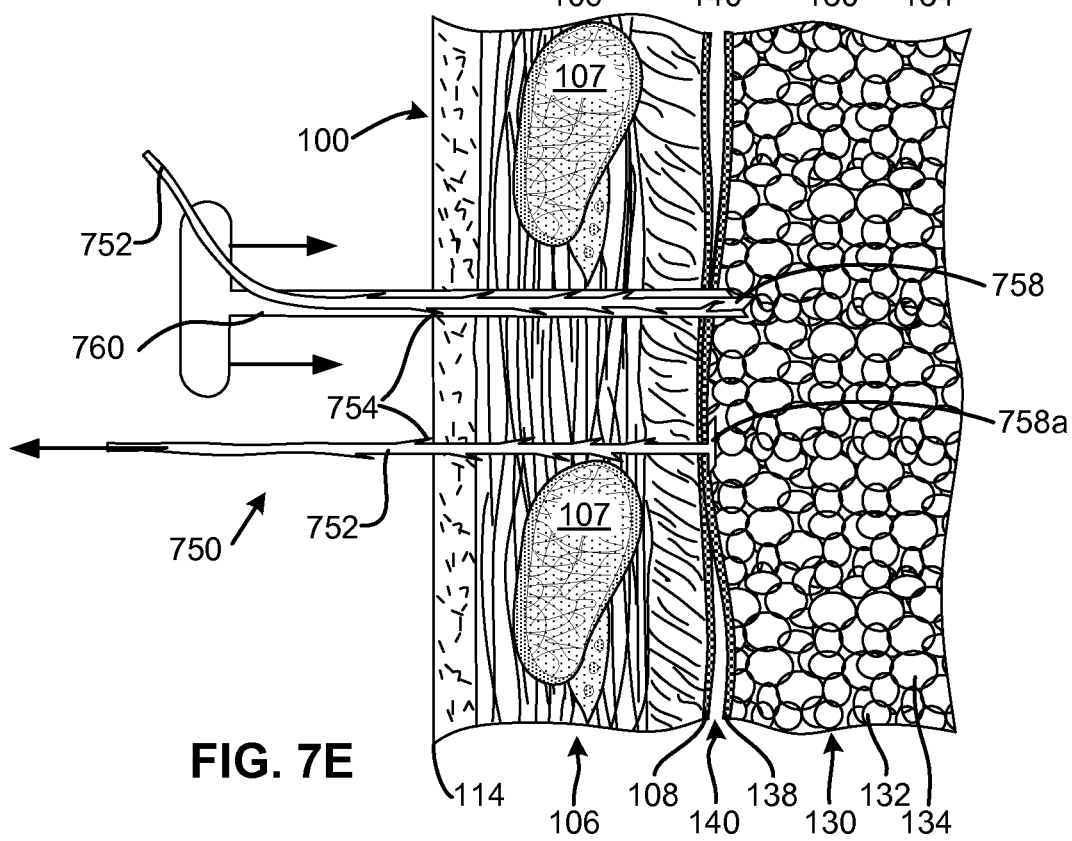

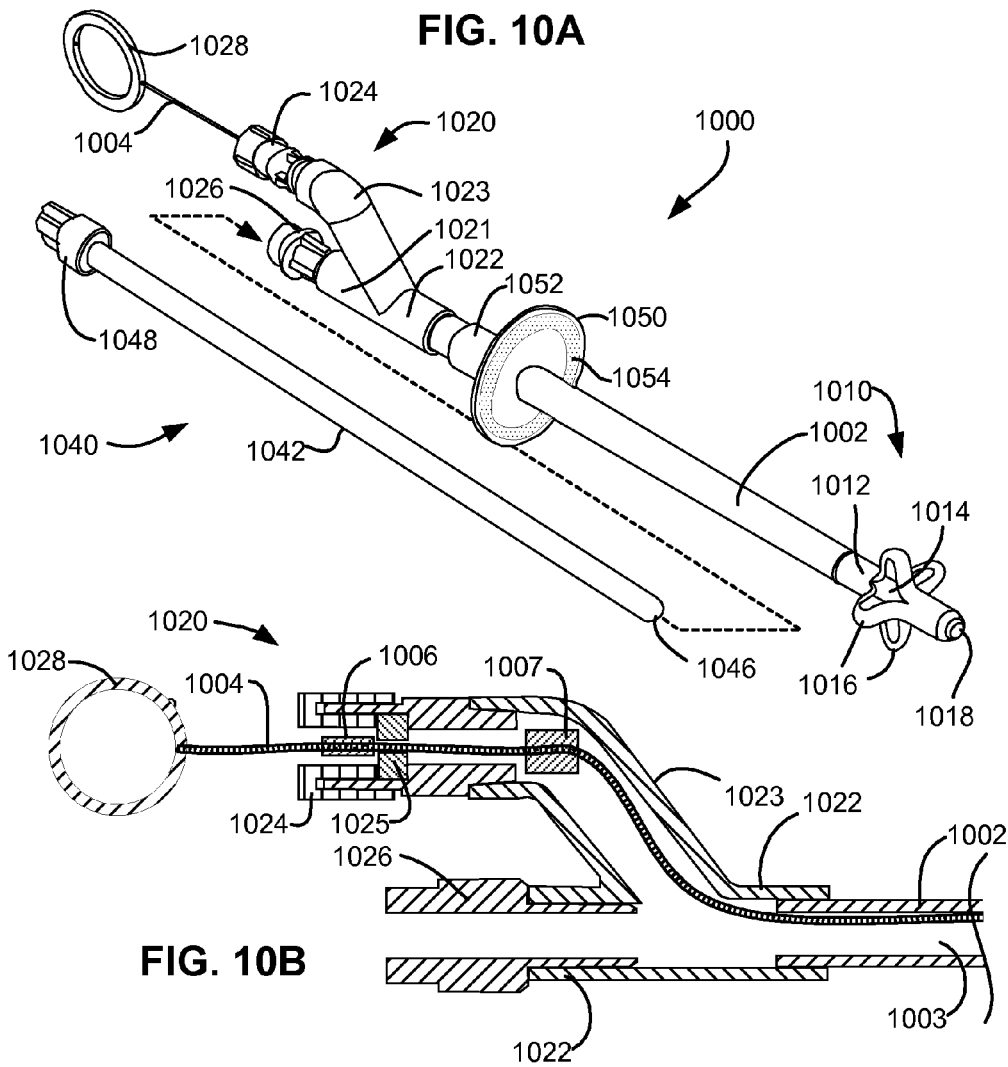
FIG. 10A
FIG. 10B
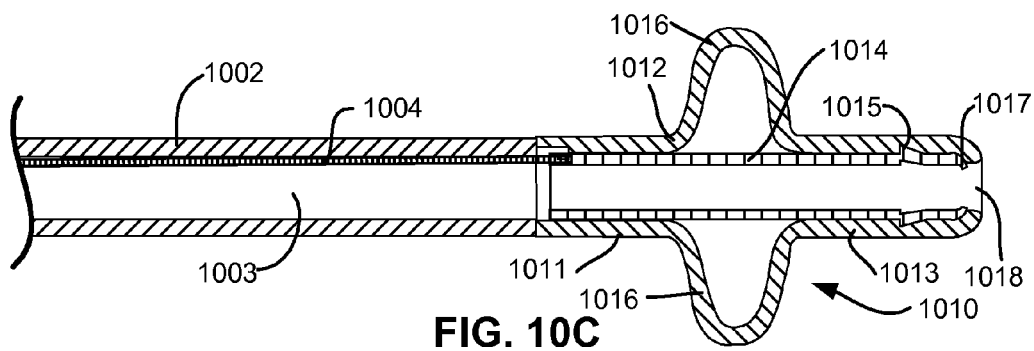
FIG. 10C

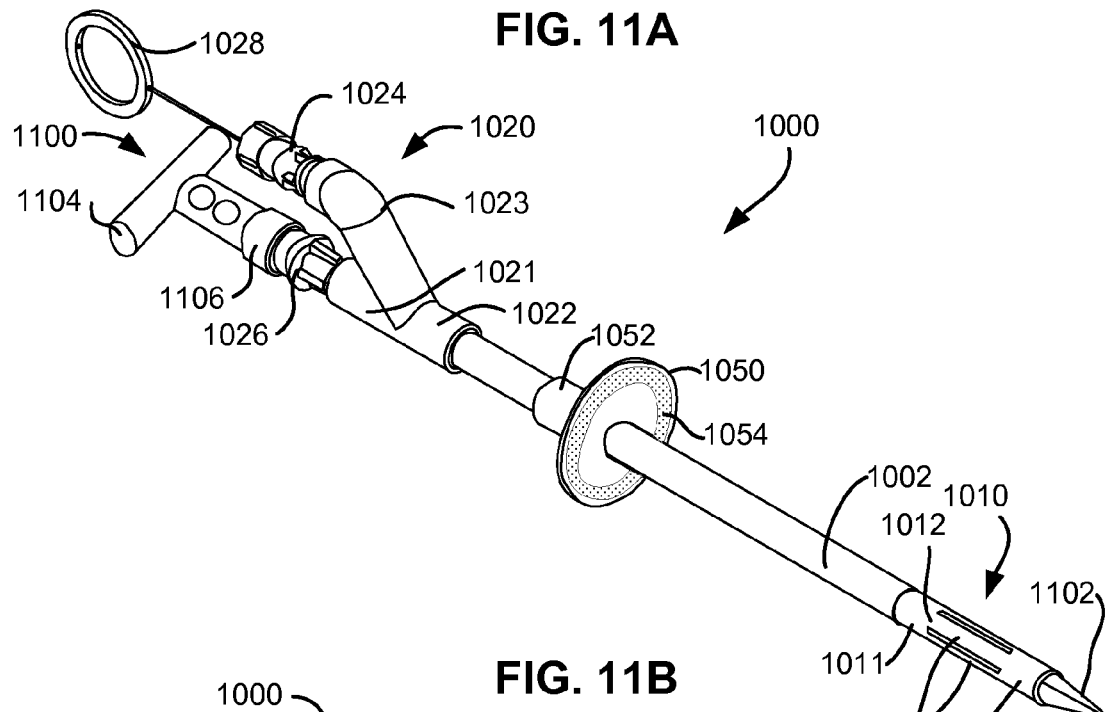
FIG. 11A
FIG. 11B
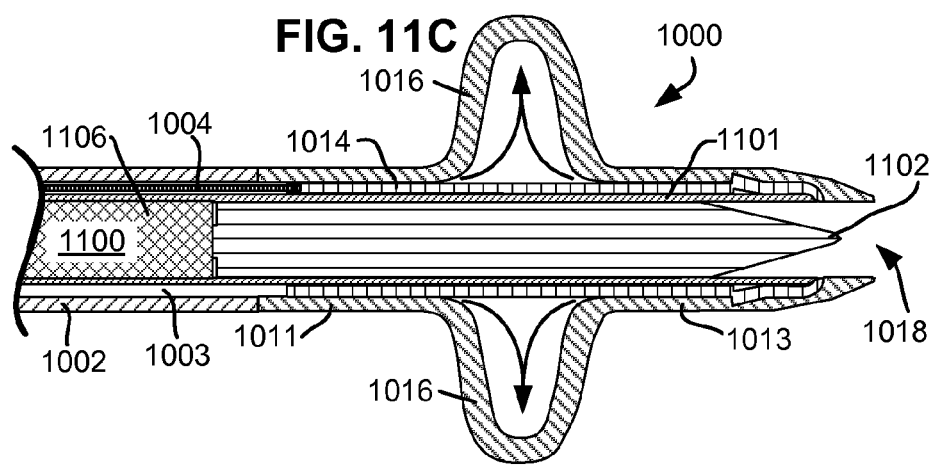
FIG. 11C

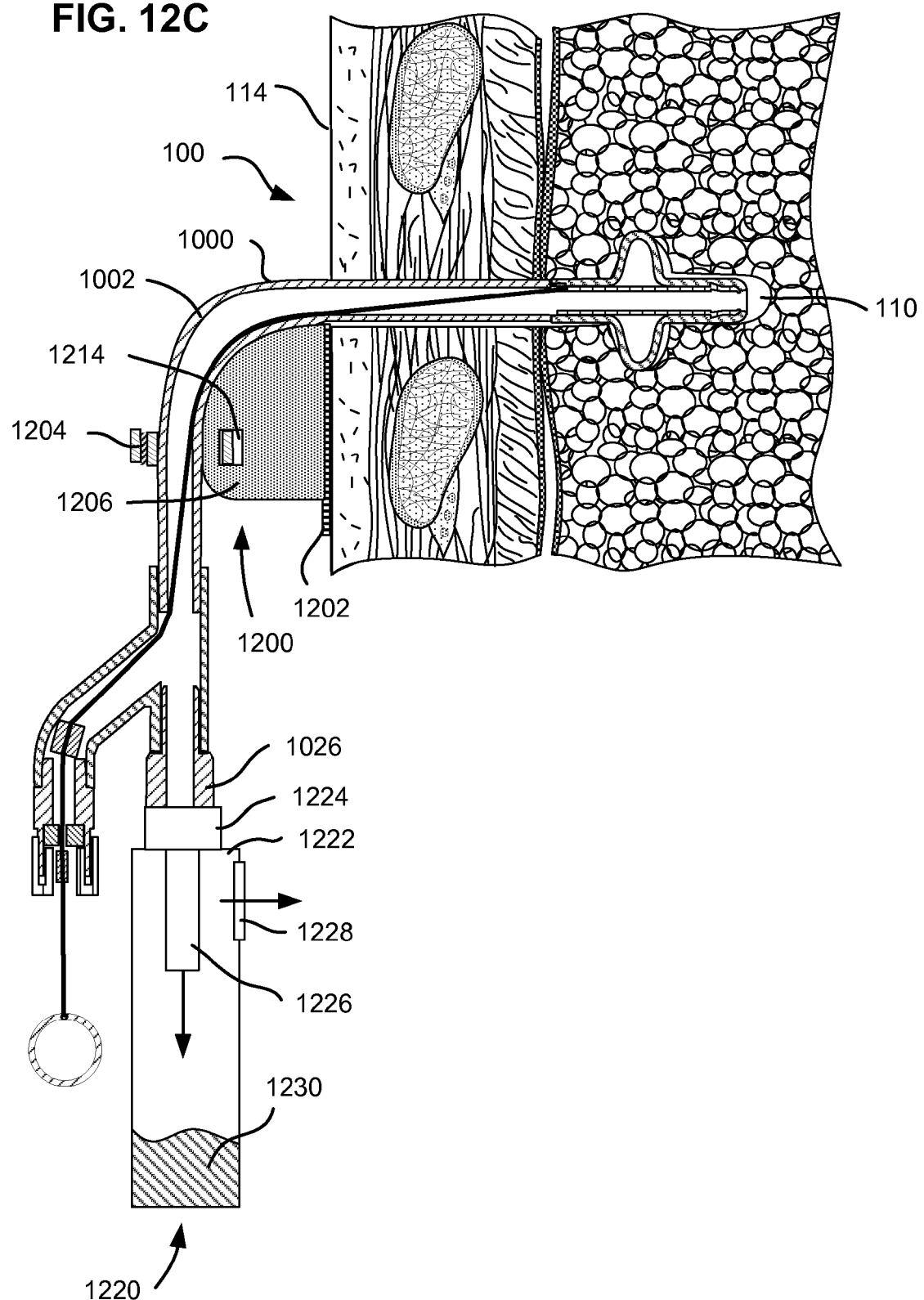

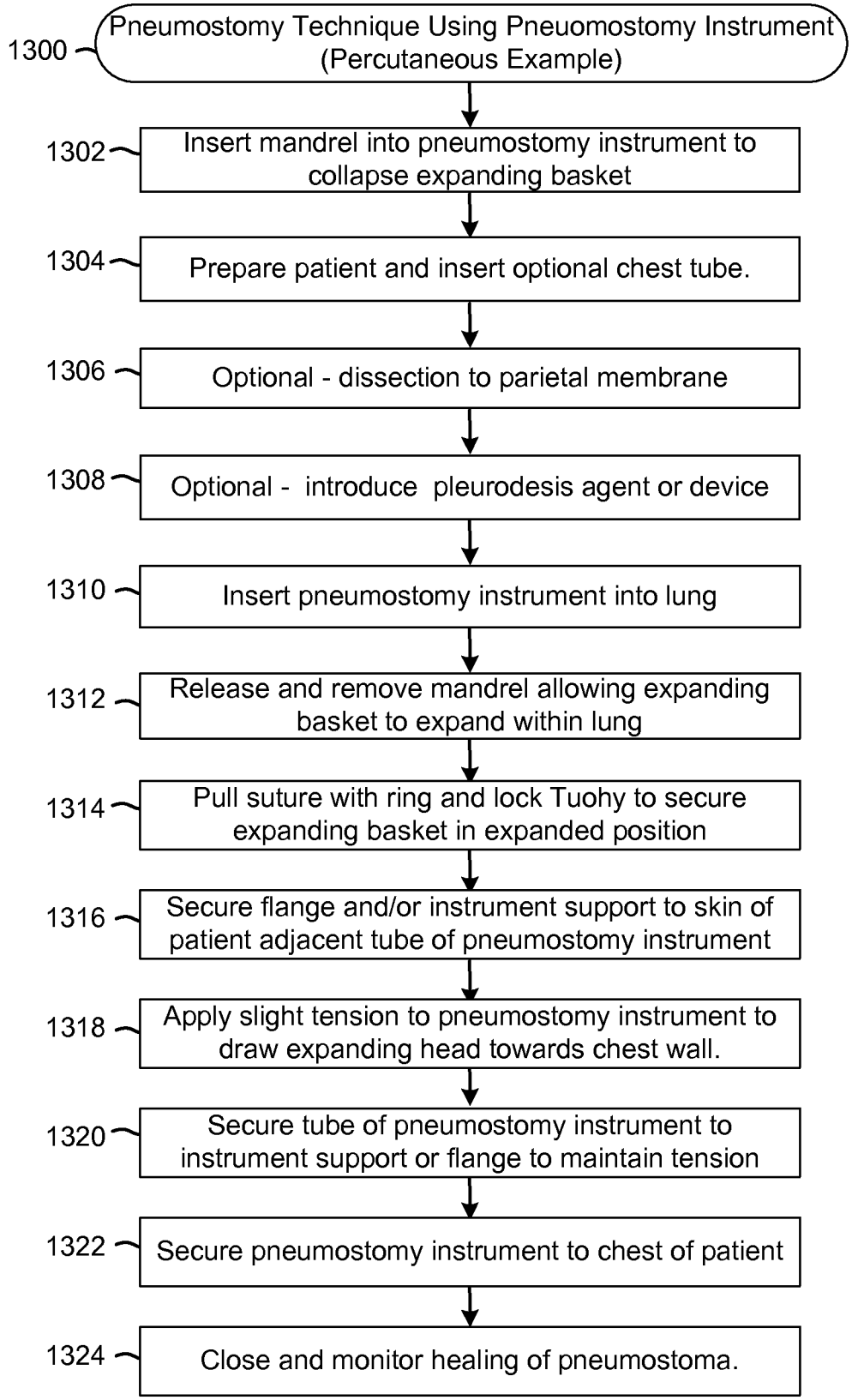

TWO-PHASE SURGICAL PROCEDURE FOR CREATING A PNEUMOSTOMA TO TREAT CHRONIC OBSTRUCTIVE PULMONARY DISEASE

CLAIM TO PRIORITY

This application is a continuation application of U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE" which application claims priority to all of the following applications including:

U.S. Provisional Application No. 61/029,830, filed Feb. 19, 2008, entitled "ENHANCED PNEUMOSTOMA MANAGEMENT DEVICE AND METHODS FOR TREATMENT OF CHRONIC OBSTRUCTIVE PULMONARY DISEASE";

U.S. Provisional Application No. 61/032,877, filed Feb. 29, 2008, entitled "PNEUMOSTOMA MANAGEMENT SYSTEM AND METHODS FOR TREATMENT OF CHRONIC OBSTRUCTIVE PULMONARY DISEASE";

U.S. Provisional Application No. 61/038,371, filed Mar. 20, 2008, entitled "SURGICAL PROCEDURE AND INSTRUMENT TO CREATE A PNEUMOSTOMA AND TREAT CHRONIC OBSTRUCTIVE PULMONARY DISEASE";

U.S. Provisional Application No. 61/082,892, filed Jul. 23, 2008, entitled "PNEUMOSTOMA MANAGEMENT SYSTEM HAVING A COSMETIC AND/OR PROTECTIVE COVER";

U.S. Provisional Application No. 61/083,573, filed Jul. 25, 2008, entitled "DEVICES AND METHODS FOR DELIVERY OF A THERAPEUTIC AGENT THROUGH A PNEUMOSTOMA";

U.S. Provisional Application No. 61/084,559, filed Jul. 29, 2008, entitled "ASPIRATOR FOR PNEUMOSTOMA MANAGEMENT";

U.S. Provisional Application No. 61/088,118, filed Aug. 12, 2008, entitled "FLEXIBLE PNEUMOSTOMA MANAGEMENT SYSTEM AND METHODS FOR TREATMENT OF CHRONIC OBSTRUCTIVE PULMONARY DISEASE";

U.S. Provisional Application No. 61/143,298, filed Jan. 8, 2009, entitled "METHODS AND APPARATUS FOR THE CRYOTHERAPY CREATION OR RE-CREATION OF PNEUMOSTOMY"; and U.S. Provisional Application No. 61/151,581, filed Feb. 11, 2009, entitled "SURGICAL INSTRUMENTS AND PROCEDURES TO CREATE A PNEUMOSTOMA AND TREAT CHRONIC OBSTRUCTIVE PULMONARY DISEASE".

All of the afore-mentioned applications are incorporated herein by reference in their entireties.

CROSS-REFERENCE TO RELATED APPLICATIONS

This application is related to all of the above provisional applications and all the patent applications that claim priority thereto including:

This application is related to all of the following applications including U.S. patent application Ser. No. 12/388,465, filed Feb. 18, 2009, now U.S. Pat. No. 7,909,803, issued Mar. 22, 2011, entitled "ENHANCED PNEUMOSTOMA MANAGEMENT DEVICE AND METHODS FOR TREATMENT OF CHRONIC OBSTRUCTIVE PULMONARY DISEASE";

U.S. patent application Ser. No. 12/388,447, filed Feb. 18, 2009, entitled "PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,451, filed Feb. 18, 2009, entitled "PNEUMOSTOMA MANAGEMENT METHOD FOR TREATMENT OF CHRONIC OBSTRUCTIVE PULMONARY DISEASE";

U.S. patent application Ser. No. 12/388,435, filed Feb. 18, 2009, entitled "TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,438, filed Feb. 18, 2009, entitled "ACCELERATED TWO-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,441, filed Feb. 18, 2009, entitled "SINGLE-PHASE SURGICAL PROCEDURE FOR CREATING A PNEUMOSTOMA TO TREAT CHRONIC OBSTRUCTIVE PULMONARY DISEASE";

U.S. patent application Ser. No. 12/388,460, filed Feb. 13, 2009, entitled "PNEUMOSTOMA MANAGEMENT SYSTEM HAVING A COSTMETIC AND/OR PROTECTIVE COVER"

U.S. patent application Ser. No. 12/388,455, filed Feb. 18, 2009, entitled "DEVICES AND METHODS FOR DELIVERY OF A THERAPEUTIC AGENT THROUGH A PNEUMOSTOMA";

U.S. patent application Ser. No. 12/388,461, filed Feb. 18, 2009, now U.S. Pat. No. 8,348,906 issued Jan. 8, 2013, entitled "ASPIRATOR FOR PNEUMOSTOMA MANAGEMENT";

U.S. patent application Ser. No. 12/388,462, filed Feb. 18, 2009, now U.S. Pat. No. 7,927,324 issued Apr. 19, 2011, entitled "ASPIRATOR AND METHOD FOR PNEUMOSTOMA MANAGEMENT";

U.S. patent application Ser. No. 12/388,458, filed Feb. 18, 2009, entitled "FLEXIBLE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,459, filed Feb. 18, 2009, entitled "METHODS AND DEVICES FOR FOLLOW-UP CARE AND TREATMENT OF A PNEUMOSTOMA";

U.S. patent application Ser. No. 12/388,453, filed Feb. 18, 2009, now U.S. Pat. No. 8,252,003 issued Aug. 28, 2012, entitled "SURGICAL INSTRUMENTS FOR CREATING A PNEUMOSTOMA AND TREATING CHRONIC OBSTRUCTIVE PULMONARY DISEASE";

U.S. patent application Ser. No. 12/388,466, filed Feb. 18, 2009, entitled "ONE-PIECE PNEUMOSTOMA MANAGEMENT SYSTEM AND METHODS FOR TREATMENT OF CHRONIC OBSTRUCTIVE PULMONARY DISEASE";

U.S. patent application Ser. No. 12/388,467, filed Feb. 18, 2009, now U.S. Pat. No. 8,347,880 issued Jan. 8, 2013, entitled "PNEUMOSTOMA MANAGEMENT SYSTEM WITH SECRETION MANAGEMENT FEATURES FOR TREATMENT OF CHRONIC OBSTRUCTIVE PULMONARY DISEASE";

U.S. patent application Ser. No. 12/388,468, filed Feb. 18, 2009, now U.S. Pat. No. 8,365,722 issued Feb. 5, 2013, entitled "MULTI-LAYER PNEUMOSTOMA MANAGE-

MENT SYSTEM AND METHODS FOR TREATMENT OF CHRONIC OBSTRUCTIVE PULMONARY DISEASE";

U.S. patent application Ser. No. 12/388,469, filed Feb. 18, 2009, entitled "VARIABLE LENGTH PNEUMOSTOMA MANAGEMENT SYSTEM FOR TREATMENT OF CHRONIC OBSTRUCTIVE PULMONARY DISEASE";

U.S. patent application Ser. No. 12/388,470, filed Feb. 18, 2009, now U.S. Pat. No. 8,021,320 issued Sep. 20, 2011, entitled "SELF-SEALING DEVICE AND METHOD FOR DELIVERY OF A THERAPEUTIC AGENT THROUGH A PNEUMOSTOMA".

All of the afore-mentioned applications are incorporated herein by reference in their entireties. This patent application also incorporates by reference all patents, applications, and articles discussed and/or cited herein.

BACKGROUND OF THE INVENTION

In the United States alone, approximately 14 million people suffer from some form of Chronic Obstructive Pulmonary Disease (COPD). However, an additional ten million adults have evidence of impaired lung function indicating that COPD may be significantly underdiagnosed. The cost of COPD to the nation in 2002 was estimated to be $32.1 billion. Medicare expenses for COPD beneficiaries were nearly 2.5 times that of the expenditures for all other patients. Direct medical services accounted for $18.0 billion, and indirect cost of morbidity and premature mortality was $14.1 billion. COPD is the fourth leading cause of death in the U.S. and is projected to be the third leading cause of death for both males and females by the year 2020.

Chronic Obstructive Pulmonary Disease (COPD) is a progressive disease of the airways that is characterized by a gradual loss of lung function. In the United States, the term COPD includes chronic bronchitis, chronic obstructive bronchitis, and emphysema, or combinations of these conditions. In emphysema the alveoli walls of the lung tissue are progressively weakened and lose their elastic recoil. The breakdown of lung tissue causes progressive loss of elastic recoil and the loss of radial support of the airways which traps residual air in the lung. This increases the work of exhaling and leads to hyperinflation of the lung. When the lungs become hyperinflated, forced expiration cannot reduce the residual volume of the lungs because the force exerted to empty the lungs collapses the small airways and blocks air from being exhaled. As the disease progresses, the inspiratory capacity and air exchange surface area of the lungs is reduced until air exchange becomes seriously impaired and the individual can only take short shallow labored breaths (dyspnea).

The symptoms of COPD can range from the chronic cough and sputum production of chronic bronchitis to the severe disabling shortness of breath of emphysema. In some individuals, chronic cough and sputum production are the first signs that they are at risk for developing the airflow obstruction and shortness of breath characteristic of COPD. With continued exposure to cigarettes or noxious particles, the disease progresses and individuals with COPD increasingly lose their ability to breathe. Acute infections or certain weather conditions may temporarily worsen symptoms (exacerbations), occasionally where hospitalization may be required. In others, shortness of breath may be the first indication of the disease. The diagnosis of COPD is confirmed by the presence of airway obstruction on testing with spirometry. Ultimately, severe emphysema may lead to severe dyspnea, severe limitation of daily activities, illness and death.

There is no cure for COPD or pulmonary emphysema, only various treatments, for ameliorating the symptoms. The goal of current treatments is to help people live with the disease more comfortably and to prevent the progression of the disease. The current options include: self-care (e.g., quitting smoking), medications (such as bronchodilators which do not address emphysema physiology), long-term oxygen therapy, and surgery (lung transplantation and lung volume reduction surgery). Lung Volume Reduction Surgery (LVRS) is an invasive procedure primarily for patients who have a localized (heterogeneous) version of emphysema; in which, the most diseased area of the lung is surgically removed to allow the remaining tissue to work more efficiently. Patients with diffuse emphysema cannot be treated with LVRS, and typically only have lung transplantation as an end-stage option. However, many patients are not candidates for such a taxing procedure.

A number of less-invasive surgical methods have been proposed for ameliorating the symptoms of COPD. In one approach new windows are opened inside the lung to allow air to more easily escape from the diseased tissue into the natural airways. These windows are kept open with permanently implanted stents. Other approaches attempt to seal off and shrink portions of the hyperinflated lung using chemical treatments and/or implantable plugs. However, these proposals remain significantly invasive and are still in clinical trails in 2008. None of the surgical approaches to treatment of COPD is widely accepted. Therefore, a large unmet need remains for a medical procedure that can sufficiently alleviate the debilitating effects of COPD and emphysema.

SUMMARY OF THE INVENTION

In view of the disadvantages of the state of the art, Applicants have developed a method for treating COPD in which an artificial passageway is made through the chest wall into the lung. An anastomosis is formed between the artificial passageway and the lung by creating a seal, adhesion and/or pleurodesis between the visceral and parietal membranes surrounding the passageway as it enters the lung. The seal, adhesion and/or pleurodesis prevent air from entering the pleural cavity and causing a pneumothorax (deflation of the lung due to air pressure in the pleural cavity). The pleurodesis is stabilized by a fibrotic healing response between the membranes. The artificial passageway through the chest wall also becomes epithelialized. The result is a stable artificial aperture through the chest wall which communicates with the parenchymal tissue of the lung.

The artificial aperture into the lung through the chest wall is referred to herein as a pneumostoma. A pneumostoma provides an extra pathway that allows air to exit the lung while bypassing the natural airways which have been impaired by COPD and emphysema. By providing this ventilation bypass, the pneumostoma allows the stale air trapped in the lung to escape from the lung thereby shrinking the lung (reducing hyperinflation). By shrinking the lung, the ventilation bypass reduces breathing effort (reducing dyspnea), allows more fresh air to be drawn in through the natural airways and increases the effectiveness of all of the tissues of the lung for gas exchange. Increasing the effectiveness of gas exchange allows for increased absorption of oxygen into the bloodstream and also increased removal of carbon dioxide from the bloodstream. Reducing the amount of carbon dioxide retained in the lung reduces hypercapnia which also reduces dyspnea. The pneumostoma thereby achieves the advantages of lung volume reduction surgery without surgically removing a portion of the lung or sealing off a portion of the lung.

Pneumonostomy is a general term for the surgical creation of an artificial opening into the pleural cavity or lung such as for drainage of an abscess. The procedure for creating a pneumostoma is a type of pneumonostomy. However, to differentiate it from other types of pneumonostomy procedures, the term pneumostomy will be used herein to refer to procedures for creating a pneumostoma.

In accordance with embodiments, the present invention provides surgical techniques, procedures and instruments for pneumostomy.

In accordance with one embodiment, the present invention provides a two-phase pneumostomy technique in which a pleurodesis is created in a first procedure and a pneumostoma is created as a second procedure after a delay for creation of the pleurodesis.

In accordance with one embodiment, the present invention provides an accelerated two-phase pneumostomy technique in which a pleurodesis is created acutely at the first phase of a procedure and a pneumostoma is created as a second phase of the same procedure after creation of the pleurodesis.

In accordance with one embodiment, the present invention provides a single-phase pneumostomy technique for creating a pneumostoma in which a pleurodesis and a pneumostoma are created concurrently.

In accordance with specific embodiments, the present invention provides minimally-invasive approaches for performing a pneumostomy.

In accordance with specific embodiments, the present invention provides a percutaneous approach for performing a pneumostomy.

In accordance with specific embodiments, the present invention provides a minithoracotomy approach for performing a pneumostomy.

In accordance with specific embodiments, the present invention provides an intercostal approach for performing a pneumostomy.

In accordance with specific embodiments, the present invention provides perioperative procedures associated with performing pneumostomy.

Thus, various pneumostomy techniques, procedures and instruments are provided for creating a pneumostoma and thereby treating COPD. Other objects, features and advantages of the invention will be apparent from the drawings and detailed description to follow.

BRIEF DESCRIPTION OF THE DRAWINGS

The above and further features, advantages and benefits of the present invention will be apparent upon consideration of the present description taken in conjunction with the accompanying drawings.

FIG. 2 shows the general steps for pneumostomy in accordance with an embodiment of the present invention.

FIG. 5A shows the steps of an accelerated two-phase pneumostomy technique in accordance with an embodiment of the present invention.

FIG. 7A shows the steps of a percutaneous single-phase pneumostomy technique in accordance with an embodiment of the present invention.

FIG. 7D illustrates a lung retraction instrument for use in a pneumostomy procedure in accordance with an embodiment of the present invention.

FIG. 7E illustrates a lung anchor for use in a pneumostomy procedure in accordance with an embodiment of the present invention.

FIGS. 10A-10F show views of an alternate pneumostomy instrument for use in pneumostomy procedures in accordance with embodiments of the present invention.

FIGS. 11A-11C show views of a percutaneous insertion instrument for use in pneumostomy procedures in accordance with embodiments of the present invention.

FIGS. 12A-12E show views of an external support for a pneumostomy instrument in accordance with embodiments of the present invention FIGS. 13A-13C show steps for pneumostomy procedures in accordance with embodiments of the present invention.

DETAILED DESCRIPTION OF THE INVENTION

Figure 1A:
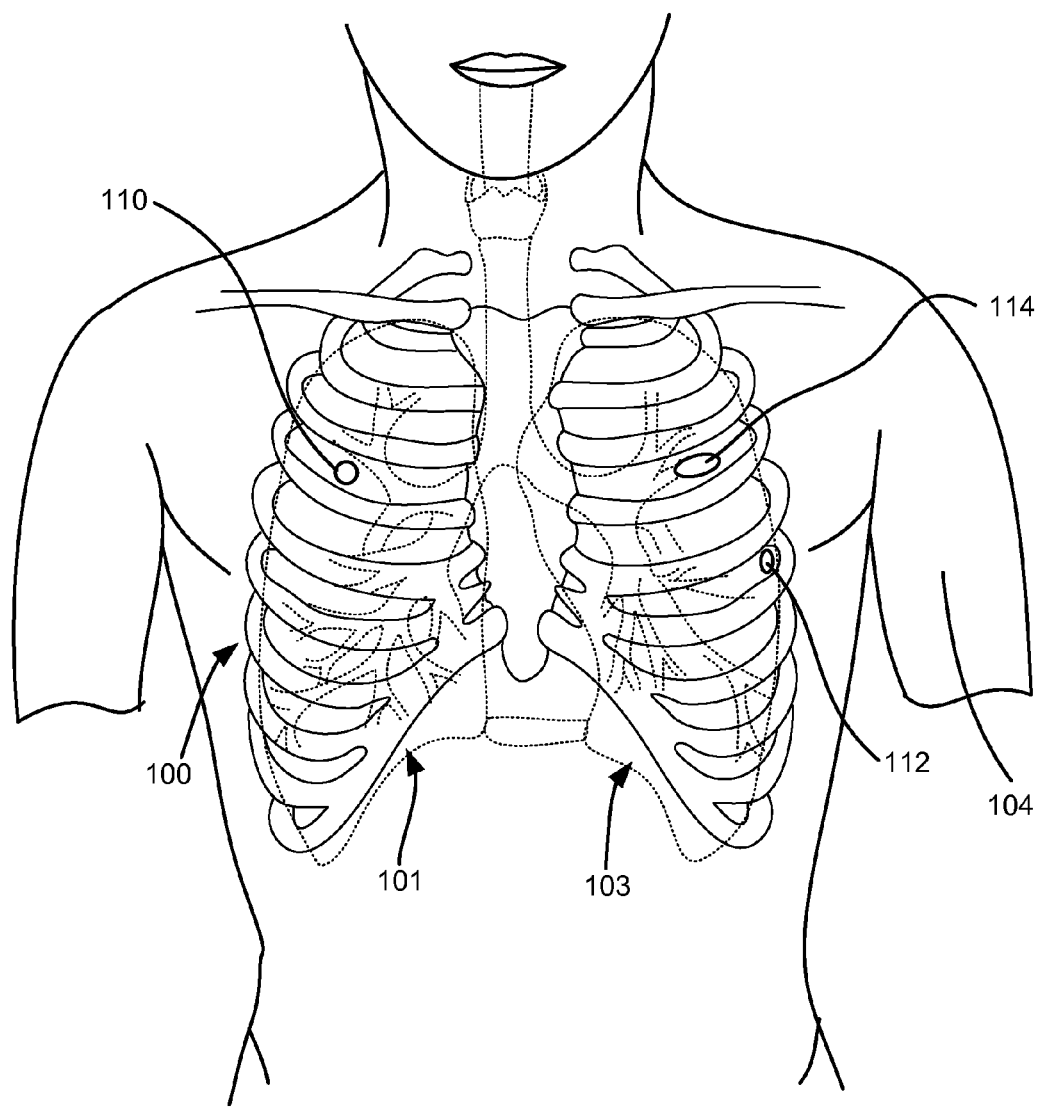
FIG. 1A shows the chest of a patient indicating alternative locations for pneumostoma that may be created using pneumostomy procedures and surgical tools of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

Pneumostoma Anatomy

FIG. 1A shows the chest of patient indicating alternative locations for creating a pneumostoma that may be managed using the system and methods of the present invention. A first pneumostoma 110 is shown on the front of the chest 100 over the right lung 101 (shown in dashed lines). The pneumostoma is preferably positioned over the second or third intercostal space on the mid-clavicular line. Thus, the pneumostoma 110 is located on the front of the chest between the second and third or third and fourth ribs. Although the pneumostoma 110 is preferably located between two ribs, in alternative procedures a pneumostoma can also be prepared using a minithoracotomy with a rib resection.

In FIG. 1A, a second pneumostoma 112 is illustrated in a lateral position entering the left lung 103 (shown in dashed lines). The pneumostoma 112 is preferably positioned over the second, third, fourth or fifth intercostal space on the mid-axillary line under the arm 104. In FIG. 1A, a third pneumostoma 114 is illustrated on the front of the chest over the left lung 103 (shown in dashed lines). The pneumostoma 114 is oval rather than round which allows a larger cross-section for the pneumostoma while still fitting within the intercostal space. In general, one pneumostoma per lung is created; however, more or less than one pneumostoma per lung may be created depending upon the needs of the patient. In most humans, the lobes of the lung are not completely separate and air may pass between the lobes. Although the pneumostoma 112 and 114 are preferably located between two ribs, in alternative procedures a pneumostoma can also be prepared using a minithoracotomy with a rib resection.

A pneumostoma is surgically created by forming an artificial channel through the chest wall and joining that channel with an opening through the visceral membrane of the lung into parenchymal tissue of the lung. The joining of two separate hollow cavities, vessels or organs to form a continuous channel is termed anastomosis. In this case the anastomosis is the joining of the artificial channel and the opening in the visceral membrane. Anastomosis seals the channel from the pleural cavity and can be achieved using adhesives, mechanical sealing and/or pleurodesis. General methods for forming the channel, forming the opening, anastomosis and pleurodesis are disclosed in Applicants' pending and issued patents and applications including U.S. patent application Ser. No. 10/881,408, now U.S. Pat. No. 7,682,332, entitled "Methods to Accelerate Wound Healing in Thoracic Anastomosis Applications" and U.S. patent application Ser. No. 12/030,006, now U.S. Pat. No. 8,062,315, entitled "Variable Parietal/Visceral Pleural Coupling" which are incorporated herein by reference in their entireties.

Figure 1B:
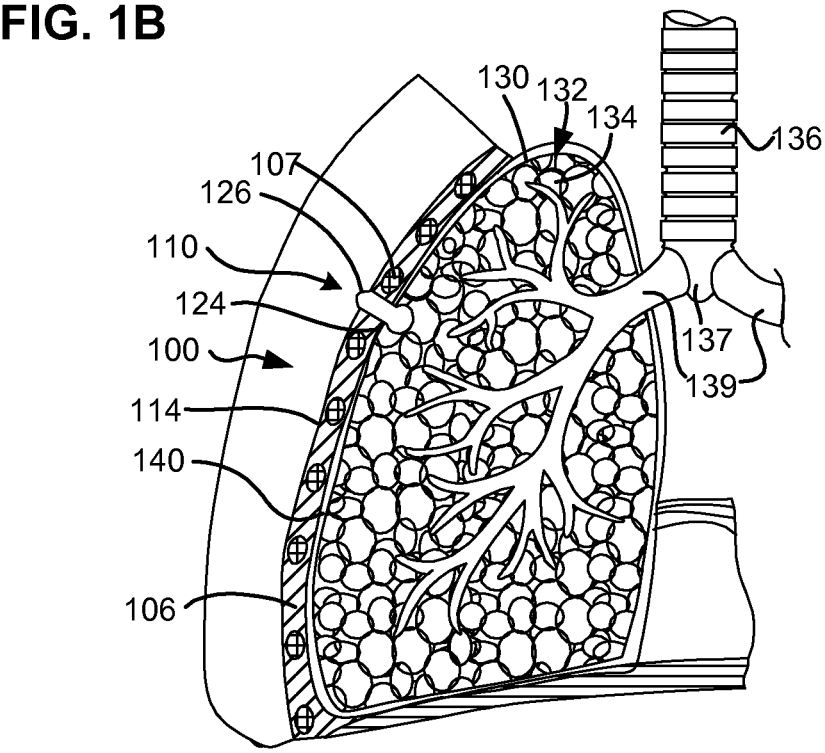
FIG. 1B shows a sectional view of the chest illustrating the relationship between the pneumostoma, lung and natural airways.

FIG. 1B shows a sectional view of chest 100 illustrating the position of the pneumostoma 110 relative to the lung and natural airways. The parenchymal tissue 132 of the lung 130 is comprised principally of alveoli 134. The alveoli 134 are the thin walled air-filled sacs in which gas exchange takes place. Air flows into the lungs through the natural airways including the trachea 136, carina 137, and bronchi 139. Inside the lungs, the bronchi branch into a multiplicity of smaller vessels referred to as bronchioles (not shown). Typically, there are more than one million bronchioles in each lung. Each bronchiole connects a cluster of alveoli to the natural airways. As illustrated in FIG. 1B, pneumostoma 110 comprises a channel through the thoracic wall 106 of the chest 100 between two ribs 107. Pneumostoma 110 opens at an aperture 126 through the skin 114 of chest 100. Aperture 126 may be round, oval or another suitable shape that allows air flow while fitting within a desirable anatomical position.

Figure 1C:
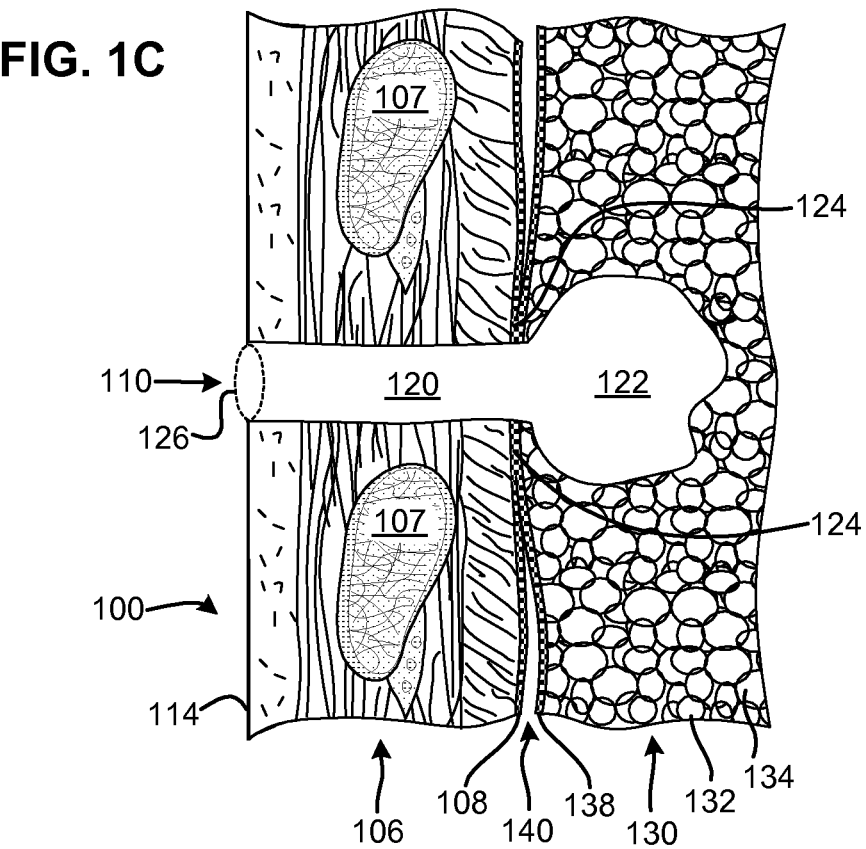
FIG. 1C shows a detailed sectional view of the pneumostoma.

FIG. 1C shows a detailed sectional view of the pneumostoma 110 and the tissue of the lung 130. As illustrated in FIG. 1C, the thoracic wall 106 is lined with the parietal membrane 108. The surface of the lung 130 is covered with a continuous sac called the visceral membrane 138. The parietal membrane 108 and visceral membrane 138 are often referred to collectively as the pleural membranes. Between the parietal membrane 108 and visceral membrane 138 is the pleural cavity (pleural space) 140. The pleural cavity usually only contains a thin film of fluid that serves as a lubricant between the lungs and the chest wall. As illustrated in FIG. 1C, pneumostoma 110 comprises a channel 120 through the thoracic wall 106 of the chest 100 between the ribs 107. The channel 120 is joined to cavity 122 in the parenchymal tissue 132 of lung 130. Although shown in FIG. 1C, having a particular shape, the channel 120 and cavity 122 will typically conform to the shape of a device inserted into the pneumostoma 110. The channel 120 may be round, oval or another suitable shape that allows air flow while fitting within a desirable anatomical position. An adhesion or pleurodesis 124 surrounds the channel 120 where it enters the lung 130. In pleurodesis 124 the pleural membranes are fused and/or adhered to one another eliminating the space between the pleural membranes in that region.

An important feature of pneumostoma 110 is the seal or adhesion surrounding the channel 120 where it enters the lung 130 which may comprise a pleurodesis 124. Pleurodesis 124 is the fusion or adhesion of the parietal membrane 108 and visceral membrane 138. A pleurodesis may be a complete pleurodesis in which the entire pleural cavity 140 is removed by fusion of the visceral membrane 138 with the parietal membrane 108 over the entire surface of the lung 130. However, as shown in FIG. 1C, the pleurodesis is preferably localized to the region surrounding the channel 120. The pleurodesis 124 surrounding the channel 120 prevents air from entering the pleural cavity 140. If air is permitted to enter pleural cavity 140, a pneumothorax will result and the lung 130 may collapse.

When formed, pneumostoma 110 provides an extra pathway for exhaled air to exit the lung 130 reducing residual volume and intra-thoracic pressure without the air passing through the major natural airways such as the bronchi 139 and trachea 136. Collateral ventilation is particularly prevalent in an emphysemous lung because of the deterioration of lung tissue caused by emphysema. Collateral ventilation is the term given to leakage of air through the connective tissue between the alveoli 134. Collateral ventilation may include leakage of air through pathways that include the interalveolar pores of Kohn, bronchiole-alveolar communications of Lambert, and interbronchiolar pathways of Martin. This air typically becomes trapped in the lung and contributes to hyperinflation. In lungs that have been damaged by COPD and emphysema, the resistance to flow in collateral channels (not shown) of the parenchymal tissue 132 is reduced allowing collateral ventilation to increase. Air from alveoli 134 of parenchymal tissue 132 that passes into collateral pathways of lung 130 is collected in cavity 122 of pneumostoma 110. Pneumostoma 110, thus, makes use of collateral ventilation to collect air in cavity 122 and vent the air outside the body via channel 120 reducing residual volume and intra-thoracic pressure and bypassing the natural airways which have been impaired by COPD and emphysema.

By providing this ventilation bypass, the pneumostoma allows stale air trapped in the parenchymal tissue 132 to escape from the lung 130. This reduces the residual volume and intra-thoracic pressure. The lower intra-thoracic pressure reduces the dynamic collapse of airways during exhalation. By allowing the airways to remain patent during exhalation, labored breathing (dyspnea) and residual volume (hyperinflation) are both reduced. Pneumostoma 110 not only provides an extra pathway that allows air to exit the lung 130 but also allows more fresh air to be drawn in through the natural airways. This increases the effectiveness of all of the tissues of the lung 130 and improves gas exchange. Increasing the effectiveness of gas exchange allows for increased absorption of oxygen into the bloodstream and also increased removal of carbon dioxide from the bloodstream. Reducing the amount of carbon dioxide retained in the lung reduces hypercapnia which also reduces dyspnea. Pneumostoma 110, thus, achieves many of the advantages sought by lung volume reduction surgery without surgically removing, disabling and/or sealing off a portion of the lung.

Applicants have found that pneumostomy procedures carried out with the techniques, procedures, and instruments of the present invention are desirable to create the pneumostoma. The pneumostomy procedures may also advantageously utilize one or more of the associated kits and perioperative methods described herein.

Perioperative Procedure & General Procedure

FIG. 2 provides a flowchart illustrating the general steps of a pneumostomy procedure 200 including diagnosis, scanning, pneumostomy and perioperative procedures.

The first step 202 of the procedure is functional testing and diagnosis. Preliminary diagnosis of COPD is considered where a patient has symptoms of a chronic cough, sputum production, dyspnea (difficult or labored breathing) and a history of exposure to risk factors for the disease—the most significant risk factor being a history of smoking. Clinical diagnosis of COPD requires confirmation by pulmonary function testing.

There are four components to pulmonary function testing: spirometry, post-bronchodilator spirometry, lung volumes, and diffusion capacity. Spirometry is the most reliable way to determine reversible airway obstruction. Spirometry is therefore often performed to assess progression of disease and to determine the effectiveness of medication. Spirometry measures the amount of air entering and leaving the lungs using a spirometry machine. The patient inhales as deeply as possible and then exhales, as forcefully and rapidly as they can into a port in the machine. The machine measures airflow that passes through the port. Usually, several exhalations are measured. The machine provides several metrics. They are expressed as percentages of what is predicted for normal lung function. Those most commonly used diagnostics of COPD are (1) forced expiratory volume after 1 second [FEV1], (2) forced vital capacity [FVC], and (3) forced expiratory flow at 25%-75% of maximal lung volume [FEF25-75]. Peak expiratory flow rate (PEFR) also can be obtained. PEFR can be compared with readings the patient obtains at home with a peak flow meter.

In a patient with COPD, the amount of air exhaled (forced vital capacity, or FVC) is reduced, compared to a person with normal lung function. Furthermore, the amount of air exhaled during the initial 1 second (FEV1) is reduced and is reduced to a greater degree than the entire FVC. Therefore, the ratio of air exhaled after 1 second to the total amount of air exhaled. In healthy lungs, 70%-75% of all the air exhaled after maximum inhalation (FVC) is exhaled within the first second (FEV1), known as the FEV1/FVC ratio. In lungs with COPD, the FEV1/FVC ratio falls below 70%-75%. The absolute value of the FEV1 is also reduced and the extent of the reduction in FEV1 is used to quantify the severity of obstruction. FEV1<70% of what is predicted for age, height, weight and race is considered mild COPD; <50% to 69%, moderate COPD; <35%-49%, severe COPD; and <35%, very severe COPD.

Post-bronchodilator Spirometry uses the same spirometry testing after giving the patient a bronchodilator, such as an inhaled beta-agonist. This procedure provides information regarding whether the airway obstruction is reversible and the potential responsiveness of the airways to medication. It is also useful for determining whether steroid treatment has been beneficial, a few weeks after initiating therapy.

Lung volumes are measured in two ways, gas dilution or body plethysmography. The gas dilution method is performed after the patient inhales a gas, such as nitrogen or helium. The amount of volume in which the gas has distributed is used to calculate the volume of air the lungs can hold. Body plethysmography requires the patient to sit in an airtight chamber (usually transparent to prevent claustrophobia) and inhale and exhale into a tube. The pressure changes in the plethysmograph are used to calculate the volume of air in the lungs. The most important lung volume measurements obtained are residual volume and total lung capacity (TLC). These measurements vary with age, height, weight, and race and are usually expressed as an absolute number and a percentage of what is predicted for a person with normal lung function. A high TLC demonstrates hyperinflation of the lungs, which is consistent with emphysema. Increased residual volume signifies air trapping. This demonstrates an obstruction to exhalation.

Blood gas analysis determines the effectiveness of gas exchange in the lungs by observing concentrations in the blood. Various non-invasive oxymetric methods may be used for measuring blood gas concentrations. Alternatively, arterial blood can be drawn and analyzed. Arterial blood gases are measured to determine the amount of oxygen dissolved in the blood (pO2), the percentage of hemoglobin saturated with oxygen (O2 sat), the amount of carbon dioxide dissolved in the blood (pCO2), and the amount of acid in the blood pH. The carbon dioxide and oxygen measures may be used to determine whether a patient needs oxygen therapy. Gas exchange can also be measured using diffusion capacity which is a measurement of gases transferred from the alveoli to the capillary. Diffusion capacity is measured by examining the uptake of a very small amount of inhaled carbon monoxide. A reduced diffusion capacity is consistent with emphysema.

Referring again to FIG. 2, lung scanning at step 204 may be used to confirm the diagnosis of COPD developed during the functional testing step 202. The CT scan may be useful to more accurately diagnose emphysema. This is usually not necessary, however, and abnormal lung anatomy is not always detected. The development of multi-channel CT scanning allows for the quantitative assessment of both the airway and parenchymal processes. CT scanning is also useful to provide images of the lung as an aid to the planning of surgical interventions such as pneumostomy. Lung scanning such as CT scanning may also be used to assess collateral ventilation in the lung including the extent of collateral ventilation both within and between lobes of the lung. The results of the pneumostomy procedure are improved by placing the pneumostoma in a region of high collateral ventilation. Thus, the extent of collateral ventilation observed by lung scanning may be used to determine the patients that will benefit most of pneumostomy and the best placement of a pneumostoma in a particular patient. Lung scanning is, therefore, typically performed to confirm the COPD diagnosis and determine a suitable placement for the pneumostoma.

Based upon the functional testing and lung imaging, it may be determined at step 206 whether a particular patient meets the criteria for pneumostoma creation. As a general rule, pneumostoma creation is suitable for patients with COPD that is not reversible using pharmaceuticals and pulmonary rehabilitation therapy. Pneumostomy will be most advantageous for patients with severe and very severe COPD as indicated by functional testing though patients with moderate COPD may also benefit. The general health of the patient and their ability to tolerate the procedure should also be taken into account.

For patients who will benefit from pneumostomy, several weeks of pulmonary rehabilitation therapy 208 should be performed before the procedure. Pulmonary rehabilitation therapy 208 combines exercise training and behavioral and educational programs designed to help patients with COPD control symptoms and improve day-to-day activities. The main goals of pulmonary rehabilitation therapy are to help patients improve their lung health and function. Pulmonary rehabilitation may reduce and control breathing difficulties and other symptoms; provide coping strategies and maintain healthy behaviors such as smoking cessation, good nutrition, and exercise. Pulmonary rehabilitation can reduce the number and length of hospital stays and increase the patient's chances of living longer. Pulmonary rehabilitation improves the likelihood of a successful outcome in a procedure to create a pneumostoma and maintain a pneumostoma after the procedure.

In procedure planning step 210, the physician determines a suitable placement for the pneumostoma based upon the results of the lung scanning, patient anatomy and physical abilities of the patient. It is desirable that the patient be able to undertake the long-term management of the pneumostoma. Thus, it is important that the patient be able to comfortably view (with a mirror) and reach the location of the pneumostoma in order to clean the pneumostoma and insert or remove pneumostoma management devices. Other factors to consider in determining placement include the thickness of muscle and/or fat at the possible location sites, the disease state of the lung, any abnormal lung anatomy, and cosmetic considerations. Also, in planning the procedure, the physician may choose one of several different approaches to the procedure. In particular, there are open, minimally invasive and percutaneous approaches. Which approach is selected will depend upon the selected placement, the results of the CT scan, patient anatomy and patient procedure tolerance. One important aspect of procedure tolerance is the need for general anesthetic and ventilation. COPD patients are often highly sensitive to anesthesia and ventilation, and, thus, it is desirable to avoid them if possible. In general, the physician will select the least invasive procedure with good probability of success.

After planning the placement, procedure and approach, the pneumostomy procedure 212 may be performed. The pneumostomy procedure creates a pneumostoma as described with respect to FIGS. 1A-1C above. The goal of the procedure is to form a stable epithelialized channel through the chest wall connected with a cavity in the parenchymal tissue of the lung inside the visceral membrane with a seal between the visceral and parietal membranes surrounding the channel such as a pleurodesis. There are four different techniques for the pneumostomy procedure which differ primarily in the time and/or manner in which a pleurodesis is created. In a two-phase technique, a pleurodesis is formed in a preliminary procedure and after one or more days, when the pleurodesis has developed, the pneumostoma is created utilizing a pneumostomy catheter in a second procedure. (see FIGS. 4A-4E). In an accelerated two-phase technique, a pleurodesis is formed in an acute manner at the beginning of a procedure. After a short period, when the pleurodesis is secure, the pneumostoma is created using a pneumostomy catheter as a second step in the same procedure. (see FIGS. 5A-5C). In a single-phase technique the pleurodesis is formed at the same time as the pneumostoma and does not require a separate step. The thoracic cavity is accessed to visualize the lung, the pneumostomy catheter is inserted into the lung and then the lung is secured to the channel through the chest wall creating a sealed anastomosis which matures into a pleurodesis after the procedure. (see FIGS. 6A-6C). In a percutaneous single-phase technique, an instrument, including the pneumostomy catheter, is inserted percutaneously through the thoracic wall and into the lung. The pneumostomy catheter is then used to secure the lung to the channel through the chest wall creating a sealed anastomosis which matures into a pleurodesis after the procedure. (see FIGS. 7A-7C). Each of these procedures is described in detail below.

In each procedure, the patency of the channel is maintained in the immediate post-operative period utilizing a pneumostomy catheter. (see FIGS. 3A-3C). When the channel has healed sufficiently—usually between one and two weeks post-operatively—the pneumostomy catheter is removed and replaced with a pneumostoma management device (PMD) (see FIGS. 8A-8B). The procedure then progresses to long-term pneumostoma management 214.

After the procedure it is important that the patient continues with pulmonary rehabilitation therapy 216 to maximize the benefit of the procedure and ensure compliance with the pneumostoma management protocols. At follow-up visits the pneumostoma is inspected for injury and/or infection. Additionally, the pneumostoma is checked for continued patency. In some cases it may be necessary to intermittently reestablish the patency of the channel. Follow-up on spirometry testing may be used to monitor the benefits of the pneumostoma.

Pneumostomy Catheter

A specialized pneumostomy catheter is utilized to create a cavity in the parenchymal tissue of the lung and maintain the patency of the channel through the chest wall into the lung in each technique. The pneumostomy catheter keeps the lung apposed to the interior of the thoracic wall to safely and properly allow the pneumonostomy to heal and form. In general, the aperture and channel of the pneumostoma will conform to the exterior dimensions of the pneumostomy catheter. The pneumostomy catheter may be round, oval or another suitable shape that allows air flow while fitting within a desirable anatomical position. The pneumostomy catheter is used by the physician during the procedure to safely create the pneumonostomy channel through the chest wall and cavity in the parenchymal tissue of the lung. The pneumostomy catheter secures the lung by means of an inflatable pneumoplasty balloon on the distal end of the catheter. The pneumoplasty balloon is inflated within the parenchymal tissue to create a chamber and engage the tissue. With the pneumoplasty balloon inflated, the pneumostomy catheter can be used to position the lung against the inner thoracic wall. The catheter will be placed under a slight tension by the physician in order to hold the lung up against the inner thoracic wall. A flange sliding on the catheter acts as the counterforce member to keep the lung and the device/pneumoplasty balloon apposed to the thoracic wall. The position of the catheter and pneumoplasty balloon and the apposition of the tissues guide the formation of the transthoracic pneumostoma.

As is commonly with respect to medical devices, the proximal end of the device is that end that is closest to the user, typically an EMT, paramedic, surgeon, or emergency physician. The distal end of the device is that end closest to the patient or that is first inserted into the patient. The diameter of a catheter is often measured in "French Size" which is 3 times the diameter of a round catheter in millimeters (mm). For example, a 15 French catheter is 5 mm in diameter. The French size is designed to approximate the circumference of the catheter in mm and is often useful for catheters that have non-circular cross-sectional configurations.

Figure 3A:
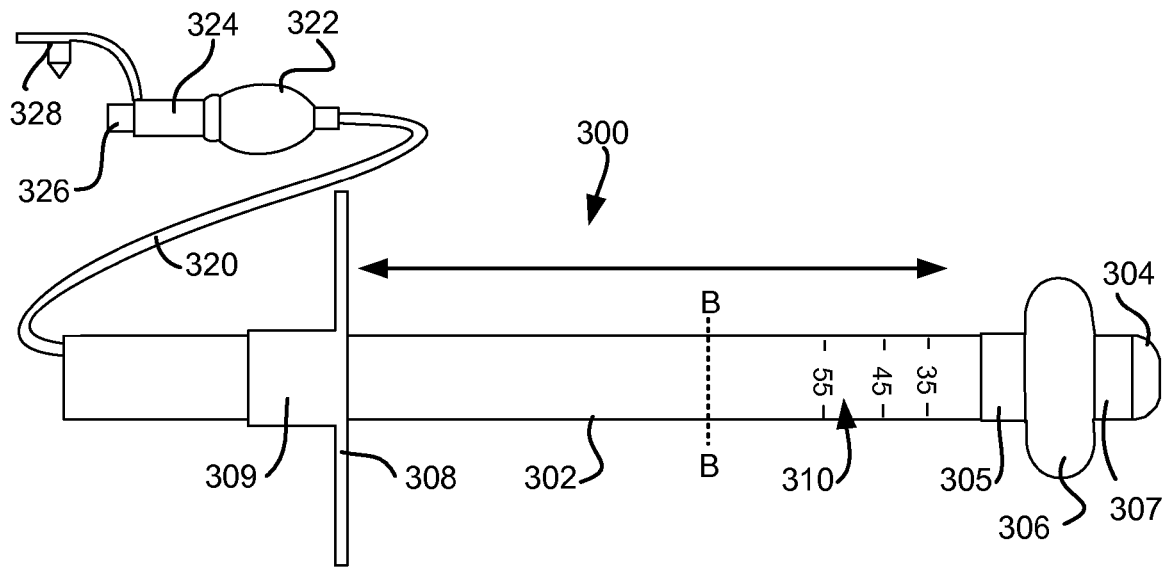
FIGS. 3A-3C show views of a pneumostomy catheter for use in pneumostomy procedures in accordance with embodiments of the present invention.
Figure 3B:
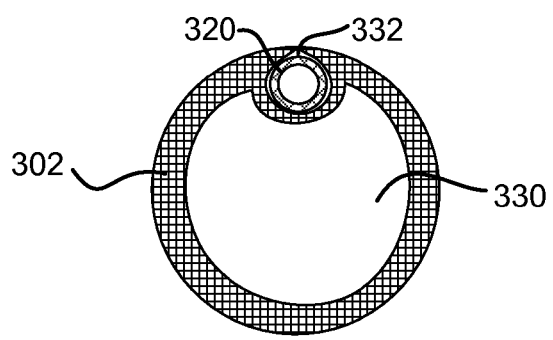
Figure 3C:
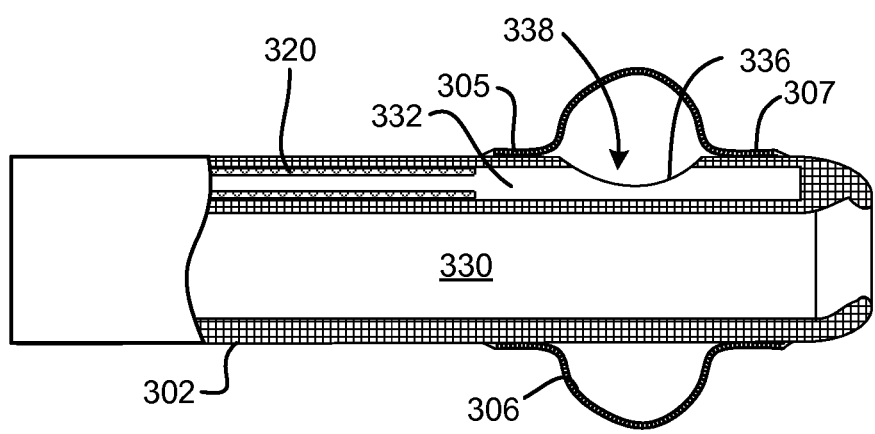

A pneumostomy catheter in accordance with one embodiment of the present invention is illustrated in FIGS. 3A-3C. As shown in FIG. 3A, pneumostomy catheter 300 comprises a tube 302 having an atraumatic distal tip 304. The tube may be from five to ten inches in length and is preferably between six and seven inches in length. The tube may be from one quarter to three quarters of an inch in diameter and is preferably between one quarter and one half of an inch in diameter. A pneumoplasty balloon 306 is located adjacent distal tip 304. An access flange 308 is connected by a collar 309 fitted around tube 302 and can slide up and down tube 302. Markings 310 on tube 302 indicate the distance from tip 304. A radio-marker or radiopaque material may be incorporated in the distal tip so that the tip may be visualized during insertion of the pneumostomy catheter. Tube 302 is also connected to an inflation tube 320. At the proximal end of the inflation tube 320 is a pilot balloon 322, a check valve 324 a coupling 326 and cap 328. Coupling 326 is designed to receive a syringe so that air, water or saline may be injected through inflation tube 320 into pneumoplasty balloon 306. Pilot balloon 322 is also connected to inflation tube 320 such that a physician may palpate pilot balloon 322 in order to gauge the level to which pneumoplasty balloon 306 is inflated. Additionally, a contrast medium may be injected into the balloon during inflation so that the inflation of the balloon may be visualized fluoroscopically or using ultrasound.

Pneumoplasty balloon 306 is preferably an elastic balloon made of silicone or its equivalent that has a low profile when not inflated. Pneumoplasty balloon 306 can alternatively be formed of a relatively inelastic material, such as polyurethane or its equivalent so that, upon injection of air water or saline, it takes on a fixed shape. In some cases, pneumoplasty balloon 306 may be made of, impregnated with, or coated with, a material that promotes pleurodesis. For example, use of a latex balloon, without another pleurodesis agent, can cause inflammation leading to pleurodesis. Pneumoplasty balloon 306 is designed to push aside the parenchymal tissues of the lung when inflated thereby creating a cavity within the parenchymal tissue. Pneumoplasty balloon 306 is also designed to anchor pneumostomy catheter 300 within the parenchymal tissue of the lung. Alternative expanding devices may be used so long as they achieve these same functions.

Pneumoplasty balloon 306 is formed as a tube, then assembled over tube 302 and sealed to tube 302 at a proximal seal 305 and distal seal 307. Pneumoplasty balloon 306 is designed to be inflated within the parenchymal tissue of the lung. Pneumoplasty balloon 306 is designed to create a cavity with the parenchymal tissue. After the cavity is created, pneumoplasty balloon 306 is designed to anchor tube 302 within the lung. Upon inflation, the diameter of pneumoplasty balloon 306 is sized as needed to create a chamber within the parenchymal tissue of the lung and anchor the pneumostomy catheter within the lung. The diameter of pneumoplasty balloon 306 may be between three quarters of an inch and two inches in diameter and is preferably between one inch and one and a quarter inches in diameter FIG. 3B shows a sectional view of tube 302 along line B-B of FIG. 3A. Tube 302 has two lumens. Main lumen 330 passes along the entire length of tube 302 and is open at the proximal end and distal end of tube 302. Inflation lumen 332 is located on the side of tube 302. Lumen 332 is open at a slit along most of the length of tube 302. Inflation lumen 332 is connected to inflation tube 320 adjacent pneumoplasty balloon 306. The distal tip of inflation tube 320 is secured into inflation lumen 332 and inflation tube 320 is removably received in the open portion of inflation lumen 332. As shown in FIG. 3C, the distal end of inflation lumen 332 is sealed. However, tube 302 is skived at location 336 between proximal seal 305 and distal seal 307 creating an aperture 338 penetrating into inflation lumen 332. The aperture 338 allows air, water or saline to be forced into pneumoplasty balloon 306 from inflation lumen 332. The components may be secured to each other using adhesive, welding, melting or other techniques appropriate to the materials to be secured.

The pneumostomy catheter may be round, oval or another suitable shape that allows air flow while fitting within a desirable anatomical position. FIG. 3F shows a sectional view of an alternative tube 303 having an oval cross-section. The cross-sectional area of tube 303 and inflation lumen 330 is increased relative to tube 302. There is no need to increase the size of inflation lumen 332 as the inflation tube 320 remains the same size. The minor dimension of tube 303 is selected such that it will fit in the intercostal space. This oval tube 303 creates an oval pneumostoma allowing for the creation of a larger cross-section pneumostoma in the intercostal space than may be achieved using a round pneumostomy catheter. Where oval tube 303 is used instead of tube 302, the other components of the pneumostomy catheter (such as flange 308) are shaped as necessary to accommodate oval tube 303.

Figure 3D:
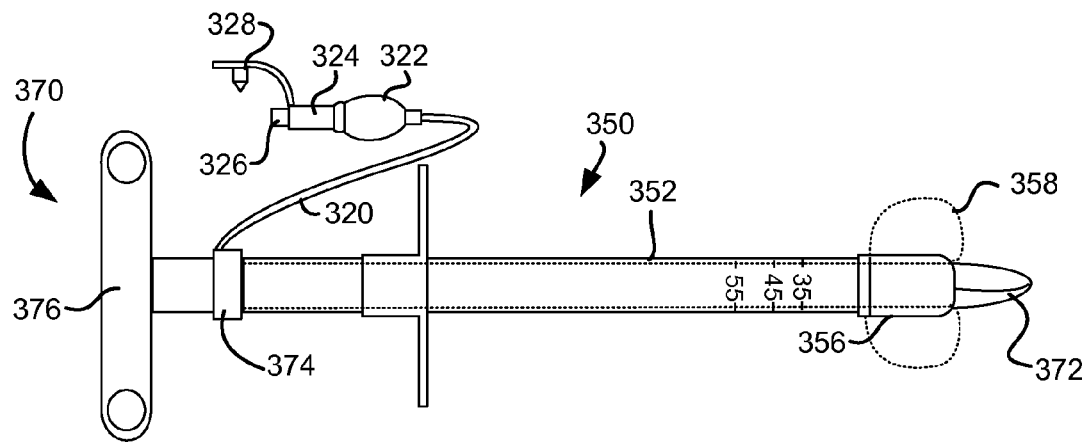
FIGS. 3D-3E show views of an alternative pneumostomy catheter assembled with a percutaneous insertion tool for use in pneumostomy procedures in accordance with embodiments of the present invention.
Figure 3E:
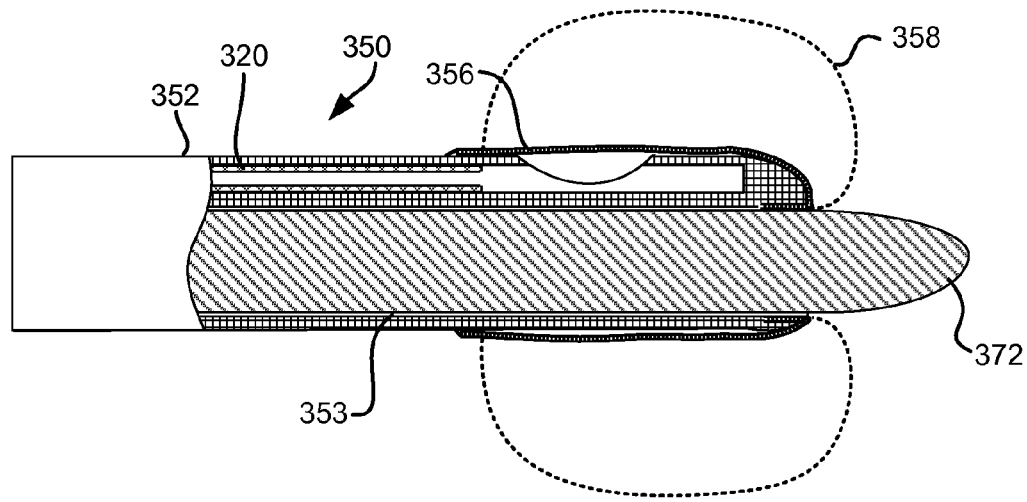
Figure 3F:
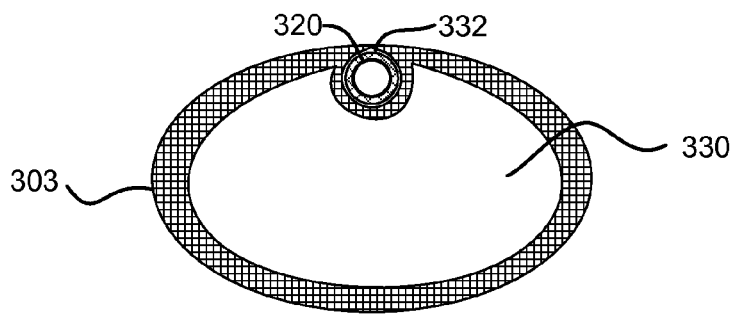
FIG. 3F shows a sectional view of an alternative component of the pneumostomy catheters of FIGS. 3A-3E.
Figure 3G:
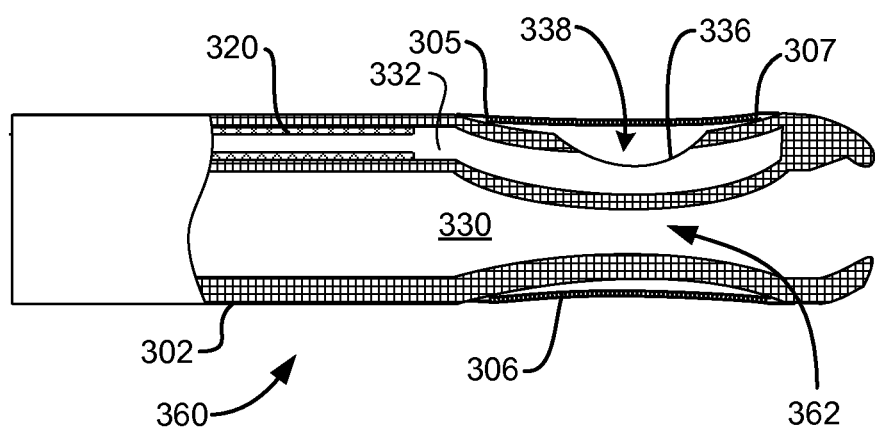
FIG. 3G shows a section view of the tip of an alternative pneumostomy catheter in accordance with an embodiment of the present invention.

FIG. 3G shows a sectional view of an alternative distal tip of a pneumostomy catheter 360. In the design shown in FIG. 3G, tube 302 is necked down in the vicinity 362 of pneumoplasty balloon 306. The necking down of tube 302 allows additional space for pneumoplasty balloon 306 in its deflated state. This is particularly useful for non-porous inelastic balloons which may be bulky when deflated. By necking down tube 302, towards the distal tip in region 362, the exterior profile of pneumoplasty balloon 306, when deflated, approaches the diameter of the main length of tube 302. This allows for easier insertion and removal of pneumostomy catheter 360.

Referring again to FIG. 3A, access flange 308 is designed such that it may be secured against the skin of the chest of the patient and collar 309 may be secured to tube 302 thereby fixing tube 302 in position relative to the chest of the patient. Access flange 308, is slidable along the length of the tube 302. The flange is designed to be positioned against the skin. The flange 308 can be sutured to the main shaft to secure the flange in position along the catheter or fixed in place by other means such as tape, adhesive, clips and staples and the like or by having a built-in securing mechanism, such as a cam, ratchet, lock or the like. The pneumostomy catheter 300 is designed to maintain a tension between the pneumoplasty balloon embedded in the lung and the thoracic wall. Once access flange 308 is secured to the main shaft, access flange 308 provides the necessary counterforce for the pneumoplasty balloon 306. Access flange 308 may also be provided with an adhesive coating to temporarily secure the flange to the skin of the patient and thereby preclude accidental dislodgment of the catheter.

After access flange 308 has been secured to the catheter, the excess length of tube 302 can be trimmed. However, prior to cutting the excess length of the tube 302, the inflation tube 320 must be separated from the tube 302 in order to maintain the inflation of the pneumoplasty balloon 306. The inflation tube 320 fits in lumen 332 of tube 302. Lumen 332 has a tear-away feature that allows inflation tube 320 to be separated from tube 302 by pulling it through the slit in the inflation lumen along the excess length. When inflation tube 320 has been separated along the excess length of tube 302, the tube 302 can be trimmed safely. Inflation tube 320 with the check valve/pilot balloon assembly is wrapped around collar 309 of access flange 308 and taped down so as not to inconvenience the patient.

For certain applications it is desirable to assemble a pneumostomy catheter with a percutaneous insertion tool so that the pneumostoma catheter can penetrate through the pleural membranes and the parenchymal tissue without previous incision or dissection. The percutaneous insertion tool is a device that permits the rapid deployment of the pneumostomy catheter through the parietal and visceral membranes into the lung. The insertion tool preferably prevents deflation of the lung by rapid deployment of the pneumostomy catheter and subsequent inflation of the pneumoplasty balloon. The percutaneous insertion tool may comprise a trocar, mandrel or the like designed to fit through the main lumen of the pneumostomy catheter and dissect tissue in a minimally traumatic way thereby allowing the pneumostomy catheter to penetrate the pleural membranes and enter the parenchymal tissue of the lung.

FIG. 3D shows a pneumostomy catheter 350 assembled with a percutaneous insertion tool 370. Percutaneous insertion tool 370 is sized to fit through the main lumen of pneumostomy catheter 350. A dissecting tip 372 of percutaneous insertion tool 370 protrudes beyond the distal tip of pneumostomy catheter 350. Dissecting tip 372 is preferably a blunt dissecting tip that pushes tissue aside rather than cutting through tissue. A shoulder 374 engages the proximal end of pneumostomy catheter 350 such that dissecting tip 372 is correctly positioned relative to the distal tip of pneumostomy catheter 350. The percutaneous insertion tool 370 has a handle 376 at the proximal end. The handle 376 is used by a physician to position the percutaneous insertion tool 370. Pneumostomy catheter 350 is similar in design to pneumostomy catheter 300 of FIG. 3A.

As shown in FIGS. 3D and 3E, the pneumoplasty balloon 356 of pneumostomy catheter 350 is preferably low profile. Likewise, tube 352 of pneumostomy catheter 350 is also preferably low profile such that the diameter of tube 352 is preferably only slightly greater than the diameter of dissecting tip 372 of percutaneous insertion tool 370. The low profile of pneumoplasty balloon 356 and tube 352 facilitate the passage of pneumostomy catheter 350 into the parenchymal tissue of the lung following the dissecting tip 372 of percutaneous insertion tool 370. In addition, as shown in FIGS. 3D and 3E, balloon 356 is attached at its distal end inside main lumen 353 of tube 352. This allows pneumostomy catheter 350 to have a lower profile at its distal end. This also allows the inflation profile of balloon 356 shown by dashed line 358 to overlap somewhat the position of dissecting tip 372.

Two-Phase Pneumostomy Technique

Figure 4A:
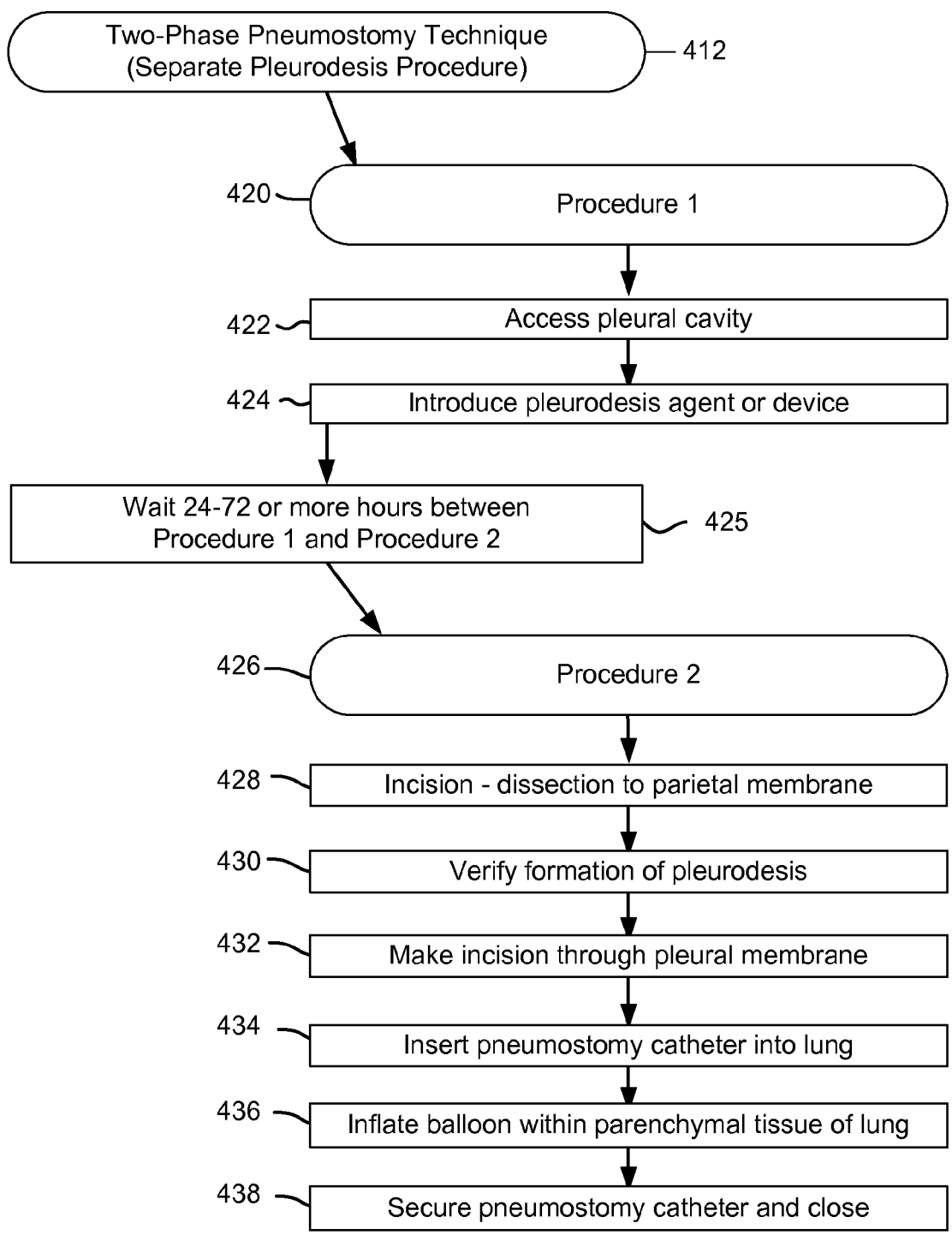
FIG. 4A shows the steps of a two-phase pneumostomy technique in accordance with an embodiment of the present invention.

FIG. 4A is a flowchart showing the steps of the two-phase pneumostomy technique 412. The two-phase technique 412 is divided into two separate procedures. In the first procedure 420 a pleurodesis is created at the site of each planned pneumostoma. The pleurodesis can be created using chemical methods including introducing into the pleural space irritants such as antibiotics (e.g. Doxycycline or Quinacrine), irritants (e.g. iodopovidone or silver nitrate), anticancer drugs (e.g. Bleomycin, Mitoxantrone or Cisplatin), cytokines (e.g. interferon alpha-2β and Transforming growth factor-β); pyrogens (e.g. *Corynebacterium parvum, Staphylococcus aureus* superantigen or OK432); connective tissue proteins (e.g. fibrin or collagen) and minerals (e.g. talc slurry). A pleurodesis can also be created using surgical methods including pleurectomy. For example, the pleural space may be mechanically abraded during thoracoscopy or thoracotomy. This procedure is called dry abrasion pleurodesis. A pleurodesis may also be created using radiotherapy methods, including radioactive gold or external radiation. These methods cause an inflammatory response and or fibrosis, healing, and fusion of the pleural membranes.

In preferred embodiments, the pleurodesis procedure is performed under local anesthetic as an out-patient procedure. The pleurodesis is created between the visceral membrane of the lung and the parietal membrane on the inner wall of the thoracic cavity. At step 422, a small incision is made at the target location under local anesthesia. At step 424, a catheter is introduced into the pleural cavity to deliver a pleurodesis agent to the localized area surrounding the target location. A guide-wire may optionally be used to guide the catheter or other delivery mechanism into the pleural cavity while avoiding perforation of the lung. The pleurodesis agent is preferably a solid, mesh or gel which can be localized to the target location. Alternatively or in combination, a device may be introduced through the incision to perform a pleurectomy of the target location by e.g. mechanical abrasion of the parietal membrane. Localized pleurodesis may be enhanced by insertion of an absorbable polyglactin mesh in combination with localized pleurodesis. The mesh may be anchored in place with a suture to the chest wall. The absorbable mesh also serves to reinforce the pleural membranes at the site of the pleurodesis which may be advantageous in the second phase of the technique.

A pleurodesis may also be created at step 422 without entering the thoracic cavity or penetrating the parietal pleura. The physician makes a small incision to visualize the parietal membrane without penetrating the parietal membrane. Once the parietal membrane is exposed, an irritant is packed against the parietal membrane external to the pleural cavity. Over time the irritant causes inflammation of the parietal membrane and pleurodesis between pleural membranes. Pleurodesis agents may be utilized as described above.

The location of the pleurodesis should either be recorded with respect to a stable anatomic feature, or marked on the skin of the patient (if the time between the first and second procedures is to be short). Alternatively, an implantable marker may be used that can be located fluoroscopically or under ultrasound. Where an implantable mesh is used as part of the pleurodesis procedure, the mesh may be provided with markers including, for example, radiopaque fibers for radiographic imaging, or echogenic cavities for ultrasound imaging. Echogenic cavities may be readily formed when extruding polyglactin and can be incorporated in the polyglactin mesh used to help generate pleurodesis. Alternatively, markers such as RFID tags or metal components may be used which may be located from out side of the device with simple handheld devices, for example, RFID antenna and/or metal detector. The marker is preferably readily localized in order to guide placement of the channel for the pneumostoma in the second phase of the procedure.

Figure 4B:
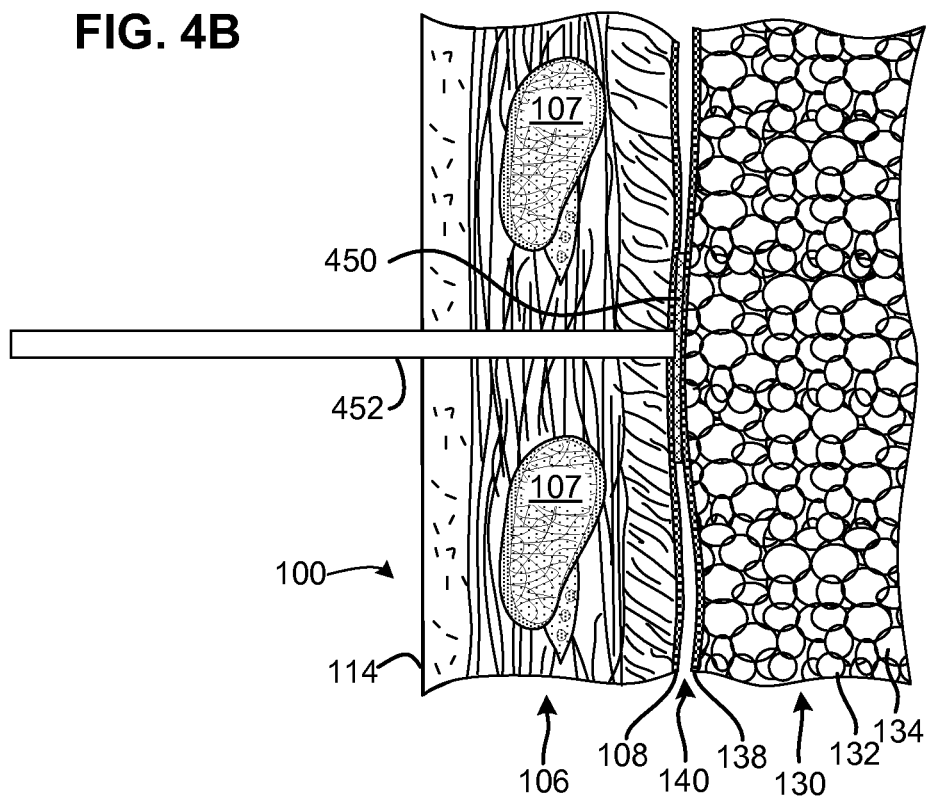
FIGS. 4B-4C illustrate the first phase of the two-phase pneumostomy technique of FIG. 4A.

FIG. 4B, illustrates the delivery of a mesh 450 through a delivery catheter 452 into the pleural cavity 140 between the visceral membrane 138 and parietal membrane 108. After initiating the pleurodesis, catheter 452 is removed and the opening closed with a suture. Alternatively, a catheter or other device may be left in place to continue delivery of a pleurodesis-inducing agent until the pleurodesis is formed. Mesh 450 may be anchored in place with a suture and/or adhesive. Applicants' U.S. patent application Ser. No. 12/030,006, now U.S. Pat. No. 8,062,315, entitled "VARIABLE PARIETAL/VISCERAL PLEURAL COUPLING" discloses methods such as pleurodesis for coupling a channel through the chest wall to the inner volume of the lung without causing a pneumothorax and is incorporated herein by reference for all purposes.

Figure 4C:
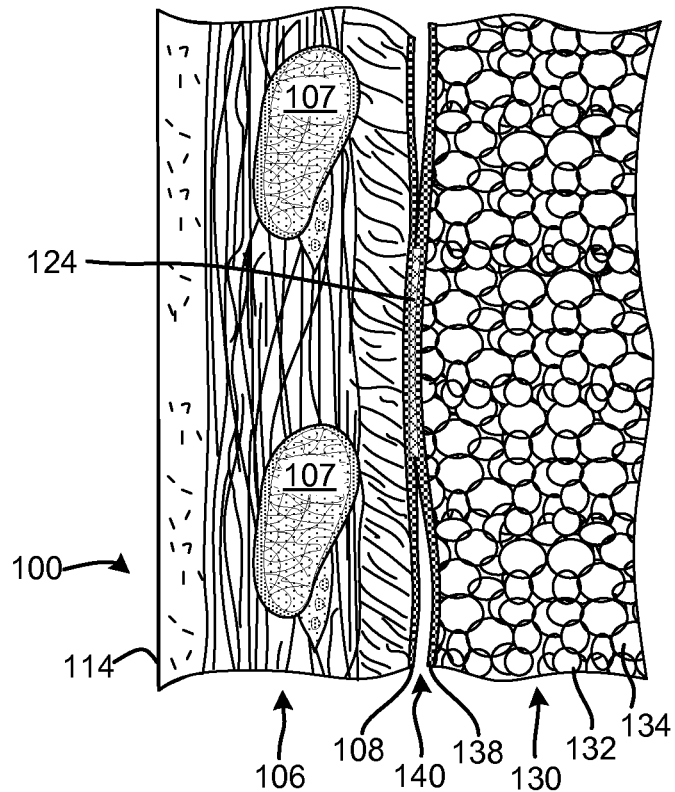

Referring again to FIG. 4A, the formation of a stable pleurodesis may take two or more days depending upon the method used. The second procedure of the first technique should not be performed until sufficient time has passed for the pleurodesis to be secure. Thus, at step 425 of the first technique, there is a waiting period having a duration of 48 hours or more. This wait step is acceptable because the initial pleurodesis procedure can be performed on an outpatient basis and the patient may, therefore, resume their regular activities between the first procedure and second procedure. FIG. 4C illustrates the formation of a stable pleurodesis. Note that in the localized region of pleurodesis 124, the visceral membrane 138 is fused with the parietal membrane 108 and there is no longer pleural space 140 between the pleural membranes in the localized target area.

Figure 4D:
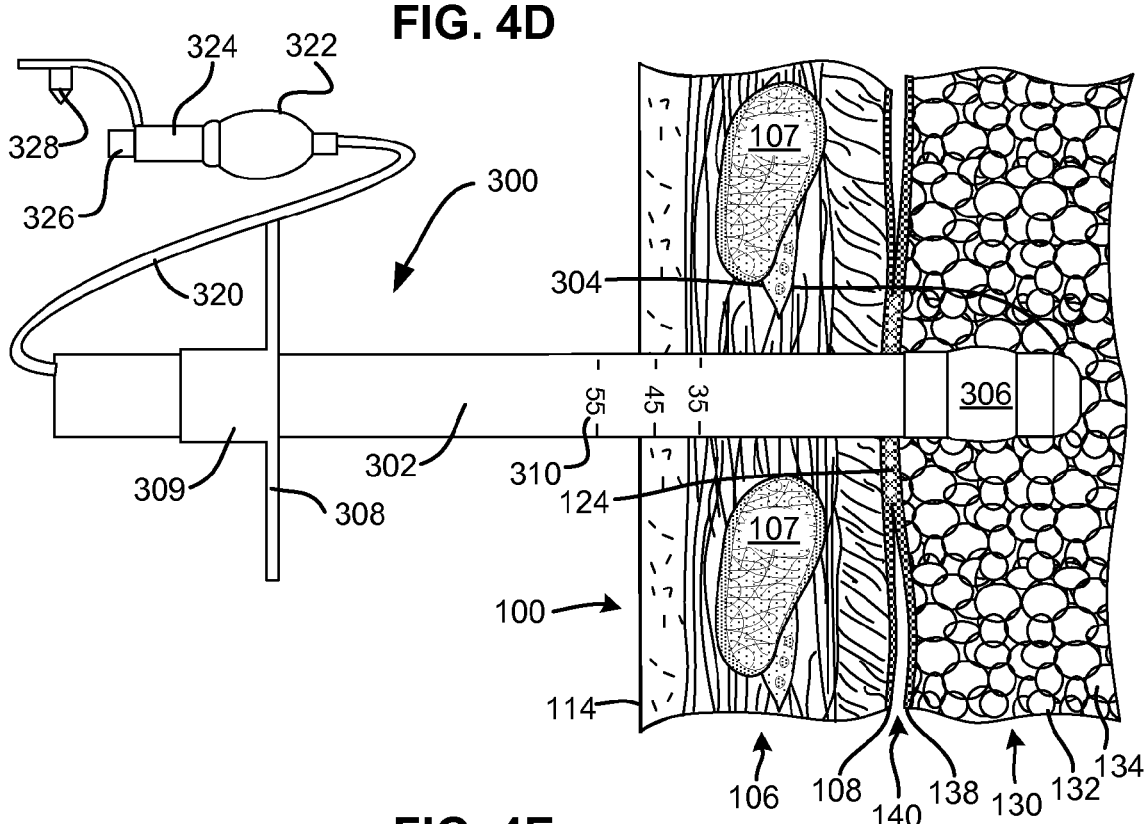
FIGS. 4D-4E illustrate the second phase of the two-phase pneumostomy technique of FIG. 4A.

Referring again to FIG. 4A, the second procedure begins at step 426. The patient is prepared using local anesthesia at the target site in addition to a sedative or general anesthesia. A chest tube may optionally be inserted into the pleural cavity in a standard manner. An incision is then opened over the pleurodesis at step 428 and the physician performs dissection to reach the parietal membrane. At step 430, the physician may palpate and/or observe the parietal membrane to verify the existence of a stable pleurodesis at the incision. At step 432, the physician creates an incision through the fused parietal and visceral membranes within the pleurodesis. If the pleurodesis has been formed correctly, the incision should not leak air into the pleural cavity and the lung will remain inflated and pushed against the chest wall. At step 434, the physician inserts the pneumostomy catheter 300 into the lung through the incision. The insertion may, alternatively, be accomplished using the percutaneous insertion tool 370 of FIGS. 3D-3E instead of making an incision. Pneumostomy catheter 300 should be inserted until the distal tip of the pneumostomy catheter and the entirety of pneumoplasty balloon 306 is located within the parenchymal tissue. FIG. 4D shows the pneumostomy catheter 300 correctly positioned through the chest wall 106 and passing through pleurodesis 124 so that the distal tip 304 of the pneumostomy catheter 300 and the entirety of deflated pneumoplasty balloon 306 is located within the parenchymal tissue 132 of lung 130.

Because the pneumostomy catheter 300 will likely fill the incision through chest wall 106, the pneumostomy catheter is provided with markings 310 so that the physician may gauge the placement of the catheter 300. The physician should measure the distance from the skin to the parietal membrane and then insert the catheter to the appropriate depth. The physician may conduct a dissection of the parenchymal tissue prior to insertion of the pneumostomy catheter—however, the parenchymal tissue is generally rather friable especially in patients with advanced COPD and so dissection may not be necessary. If a large incision in the pleural membranes was made then a purse-string suture should be made around the opening prior to incision of the catheter. The purse-string suture may be tightened after insertion of pneumostomy catheter 300.

Referring again to FIG. 4A, at step 436, after pneumoplasty balloon 306 has been correctly positioned within the parenchymal tissue, a water-filled, saline-filled or air-filled syringe is connected to the coupling of the pneumostomy catheter and material is injected into the pneumoplasty balloon. Although the filling of the pneumoplasty balloon may not be directly observed, the physician may palpate the pilot balloon 322 as a marker for pneumoplasty balloon inflation. Additionally, the amount of air, water or saline required to inflate the pneumoplasty balloon to the desired shape is relatively predictable. A contrast medium may be used to inflate the pneumostomy balloon thereby allowing the position and size of the balloon to be observed and verified, for example, with X-ray or ultrasound visualization. Inflation of pneumoplasty balloon 306 pushes aside parenchymal tissue 132 within lung 130 creating a cavity with the parenchymal tissue. The cavity should be approximately the same size and shape as pneumoplasty balloon 306. The inflated pneumostomy balloon 306 secures the distal end of the pneumostomy catheter 300 within the parenchymal tissue of the lung 130.

Figure 4E:
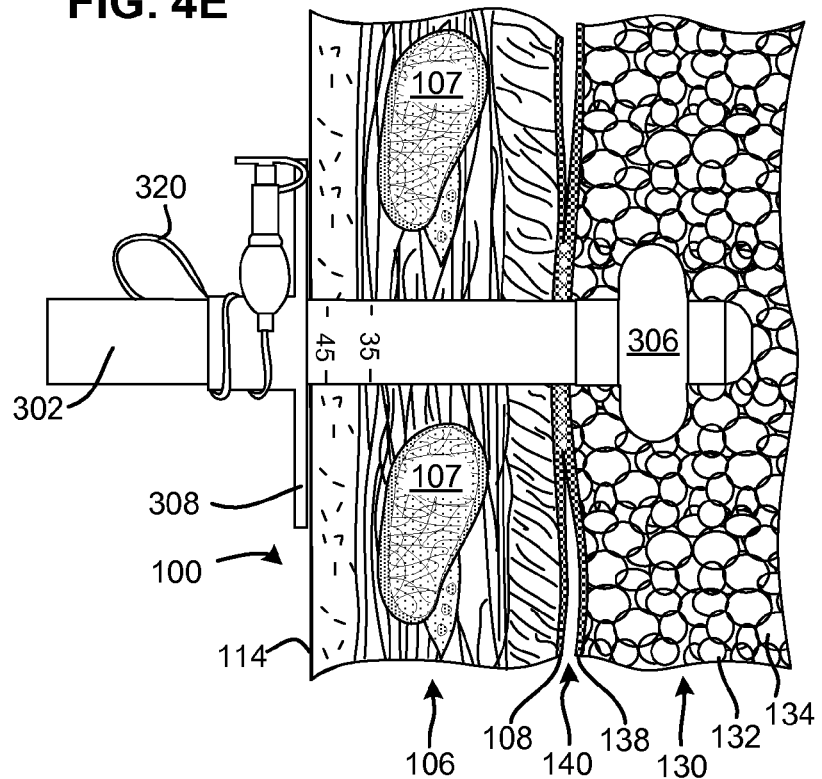

When the pilot balloon 322 indicates that the pneumoplasty balloon is inflated, the syringe is removed and the cap 328 inserted in coupling 326. At step 438, after the pneumoplasty balloon 306 is inflated, the incision through the chest wall is closed around the pneumostomy catheter using one or more sutures as necessary. A suture technique suitable for a straight incision is preferred over a, purse-string suture. Access flange 308 is then pushed against the skin of the chest wall. A slight tension is applied to the pneumostomy catheter 300. In the event of air leakage around the incision, this tension will serve to occlude the leak and prevent a pneumothorax from developing. When the desired degree of tension has been achieved, the collar 309 is fixed to tube 302 with, for example, a suture, a clamp, a hose clamp, locking collar, pin, and/or surgical tape. Access flange 308 is also secured to the skin of the patient. With access flange 308 pushed against the skin and secured, inflation tube 320 can be pulled out of the open portion of inflation lumen 332 of tube 320 up to the back of collar 309. Tube 302 can then be shortened leaving enough length to connect main lumen 330 to a water seal. Inflation tube 320 is then wrapped around collar 309 and secured. The pneumostoma site is dressed and the patient provided with standard postoperative care. FIG. 4E, illustrates pneumostomy catheter 300, with the inflated pneumoplasty balloon 306 properly located within the parenchymal tissue 132, the access flange 308 against the skin 114 of the chest 100 and the inflation tube 320 secured.

Figure 4F:
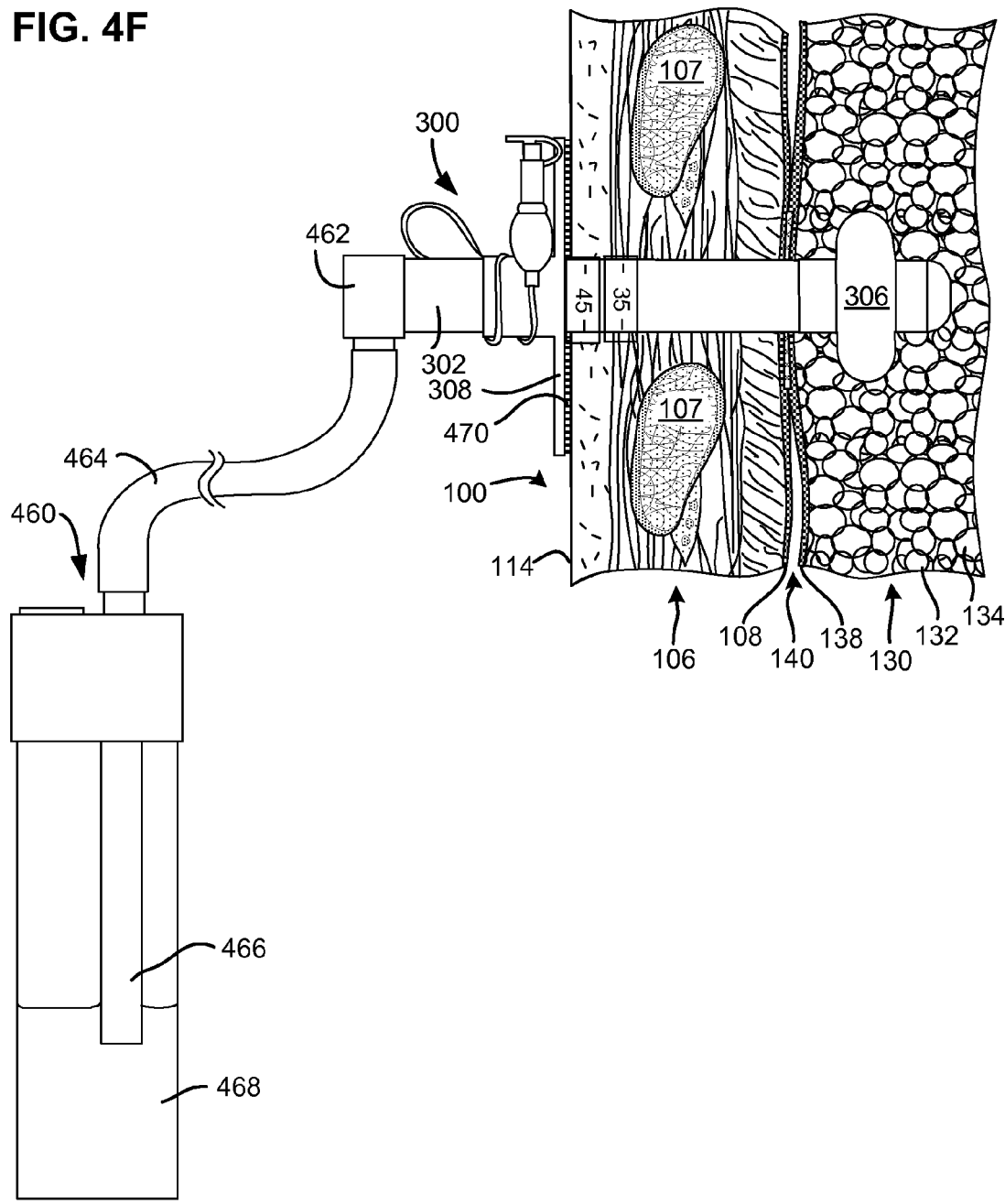
FIG. 4F illustrates an optional step of the second phase of the two-phase pneumostomy technique of FIG. 4A.

In some cases it may be desirable to connect tube 302 to a water seal, Heimlich valve or similar sealing device during the immediate postoperative period to trap air or discharge from tube 302 and prevent entry of material into the lung 130 through tube 302. FIG. 4F, illustrates pneumostomy catheter 300, with the inflated pneumoplasty balloon 306 properly located within the parenchymal tissue 132, the access flange 308 against the skin 114 of the chest 100 and the tube 302 connected to a sealing device 460. Access flange 308 may be temporarily secured to the skin of the patient using adhesive 470. As shown in FIG. 4F, a right-angle adapter 462 is connected to the proximal end of tube 302 of pneumostomy catheter 300. A flexible tube 464 connects right-angle adapter 464 to sealing device 460. Right-angle adapter 462 reduces the profile/trajectory of tube 464 away from the chest 100 of the patient. Tube 464 may be taped or secured to the chest of the patient. Sealing device 460 may be secured to the patient but will more likely be secured bedside during the immediate postoperative period.

As shown in FIG. 4F, sealing device 460 may comprise a water seal which maintains the outlet of a tube 466 under water 468. The use of a water seal for sealing device 460 allows for direct observation of any air that may exit through tube 302. Air exiting the lung via tube 302 is visible as bubbles leaving tube 466 and passing through water 468. Although a water seal is shown, sealing device 460 may alternatively comprise any suitable sealing device including a Heimlich valve, flapper valve vacuum bottle and the like. After the immediate post-operative period, the sealing device 460 may be removed and pneumoplasty catheter 300 protected with a dressing or protective cover as shown, for example, in FIGS. 9D-9G.

The patient may be discharged after a short period of observation so long as there is no evidence of air leakage into the pleural cavity and consequent pneumothorax. If a chest tube has been inserted, the chest tube may be removed when no gases are being expelled from the pleural cavity. The chest tube opening is closed and dressed after removing the chest tube. The pneumostoma catheter is left in place from seven days to two weeks as the pneumostoma heals. Air flow out through the main lumen 330 of pneumostomy catheter 300 is expected and is not an indicator of pneumothorax. It is, however, preferable to prevent air flow into the lung through the main lumen during the immediate postoperative. Thus, during this time, the proximal end of main lumen 330 may be sealed with a check valve, water seal or provided with slight vacuum. The patient may be observed on an outpatient basis during this period until the pneumostoma has healed. The dressing may be changed periodically and the pneumostoma observed to ensure that the pneumostomy catheter 300 is not disturbed and pneumoplasty balloon 306 remains inflated.

When the physician considers that the pneumostoma has healed adequately, the pneumostomy catheter 300 is removed and the pneumostoma is inspected. The physician will then confirm the size of the pneumostoma as preliminarily indicated by the markings 310 on the pneumostomy catheter 300. The physician will then provide a pneumostoma management device (PMD) of the appropriate size. PMD's are described in applicants' Provisional Application No. 61/029,826 titled "Pneumostoma Management Device And Method For Treatment Of Chronic Obstructive Pulmonary Disease" filed Feb. 19, 2008; Provisional Application No. 61/029,830 titled "Enhanced Pneumostoma Management Device And Methods For Treatment Of Chronic Obstructive Pulmonary Disease" filed Feb. 19, 2008; and Provisional Application No. 61/032, 877 titled "Pneumostoma Management System And Methods For Treatment Of Chronic Obstructive Pulmonary Disease" filed Feb. 29, 2008. The application of the PMD to the pneumostoma upon removal of pneumostomy catheter is described in more detail with respect to FIGS. 8A and 8B, below.

Accelerated Two-Phase Pneumostomy Technique

FIG. 5A is a flowchart showing the steps of an accelerated two-phase pneumostomy technique 512. This pneumostomy technique 512 is similar to the two-phase technique 412 with the primary difference that the accelerated two-phase technique 512 is performed as a single procedure. Because there is a limited time for the pleurodesis to form in this technique, different pleurodesis technology is utilized. The patient is prepared using local anesthesia at the target site in addition to a sedative or general anesthesia. A chest tube may optionally be inserted into the pleural cavity in a standard manner. At step 522, an incision is opened at the target location and the physician performs dissection to expose the parietal membrane. A larger incision may be required than in the first technique to permit use of the acute pleurodesis technology.

At step 524, a material or device is delivered to the localized area surrounding the target location to create a seal between the visceral and parietal membranes in an acute manner. The seal is created in an acute manner between the pleural membranes using biocompatible glues, adhesive meshes or mechanical means such as clamps, staples, clips and/or sutures. A range of biocompatible glues are available that may be used on the lung, including light-activatable glues, fibrin glues, cyanoacrylates and two part polymerizing glues. The application of energy such as RF energy may also be used to weld the visceral and parietal membranes to each other in an acute manner. The membranes are heated to an adequate temperature using the directed energy to sufficiently denature the collagen and/or other connective tissue fibers. The membranes are then pushed into contact allowing the partially denatured fibers of the parietal and visceral membranes to contact one another, mingle and bind to each other. In a preferred embodiment, RF energy is used to denature the collagen fibers which are then pressed together using a vacuum device. The adhesive, mechanical seal or tissue weld preferably develops into a pleurodesis over time (step 525). One or more of the pleurodesis agents discussed above may be used in conjunction with the sealing agent in order to promote pleurodesis formation following the procedure.

Figure 5B:
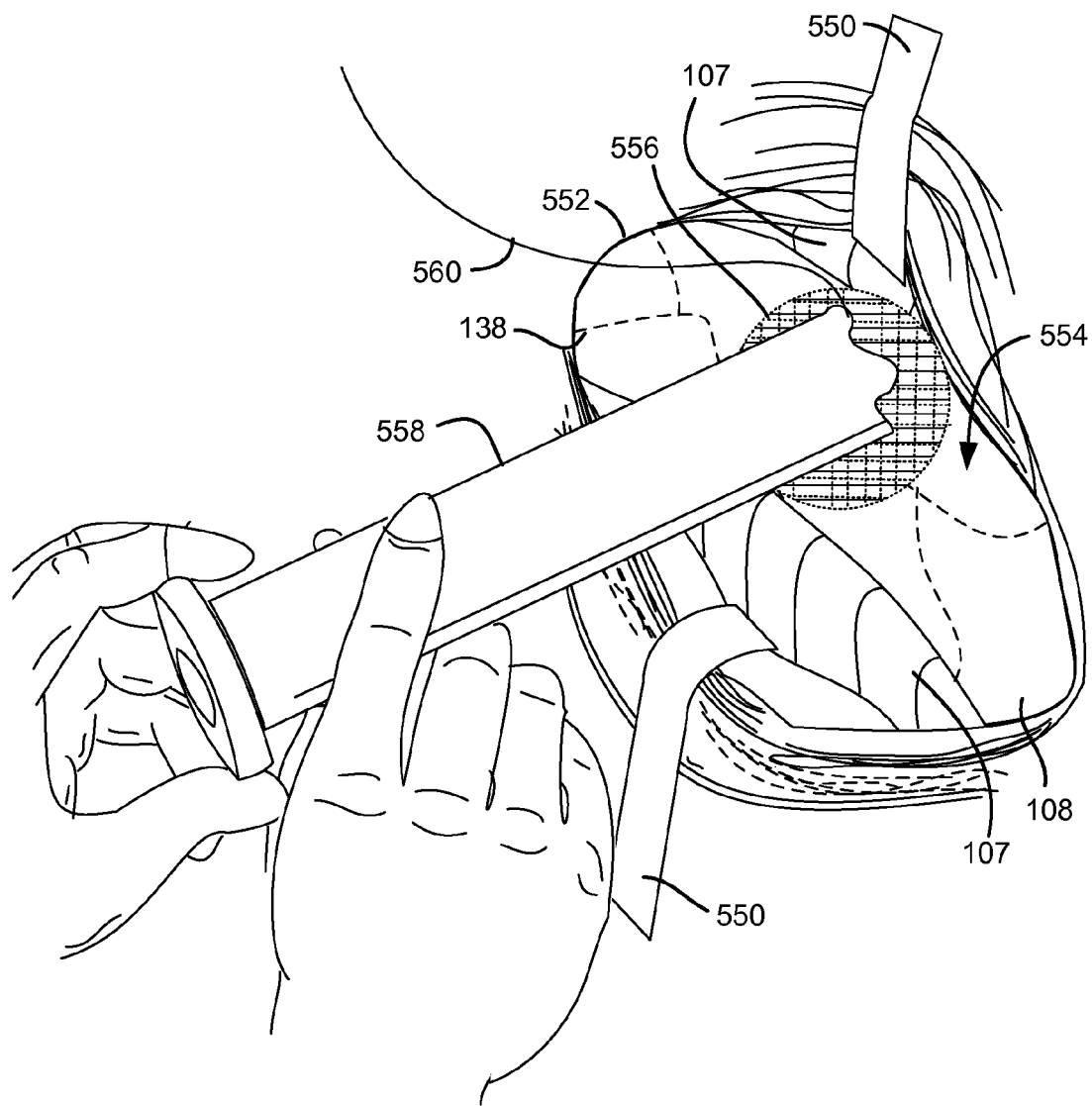
FIG. 5B illustrates the first part of the procedure of the accelerated two-phase pneumostomy technique of FIG. 5A.

As shown in FIG. 5B, an incision 552 is created over an intercostal space 554 between ribs 107. Dissection is used to expose the parietal membrane 108. The visceral membrane 138 should be visible through the parietal membrane 108. One or more retractors 550 may be used to aid visualization of the intercostal space 554. A polyglactin mesh torus 556 may be coated with an adhesive and introduced between the visceral membrane 138 and the parietal membrane 108 as shown.

After insertion of the polyglactin mesh torus 556, further steps may optionally be taken to secure the visceral membrane 138 to the parietal membrane 108 surrounding the target site. For example, an automated device 558 such as automated purse-string suturing device may be used to place a ring of suture 560 around the target site and mesh (see FIG. 5C). A suitable automated purse-string suturing device may be found in U.S. Pat. No. 5,891,159, which is incorporated herein by reference. Alternatively, suture 560 may be placed by hand. Although a purse-string suture is preferred, other tissue approximation devices such as tissue anchors, staples and clips may be used instead of, or in addition to, the adhesive and mesh in order to create an interpleural seal in an acute manner at the target location. Depending on the technology/adhesive used, the interpleural seal may be stable immediately or after a period of a few minutes.

Referring again to FIG. 5A, at step 530, the physician palpates and/or observes the parietal membrane to verify the existence of a stable interpleural seal at the incision. At step 532 the physician creates an incision through the parietal and visceral membranes within the sealed region. If the interpleural seal has been formed correctly, the incision should not leak significant amounts of air into the pleural cavity and the lung will remain inflated and pushed against the chest wall 106. A purse-string suture may be placed by hand in the visceral membrane around the incision. At step 534, the physician inserts the pneumostomy catheter 300 into the lung through the incision. The insertion may alternatively be accomplished using the percutaneous insertion tool 370 of FIGS. 3D-3E instead of making an incision.

Figure 5C:
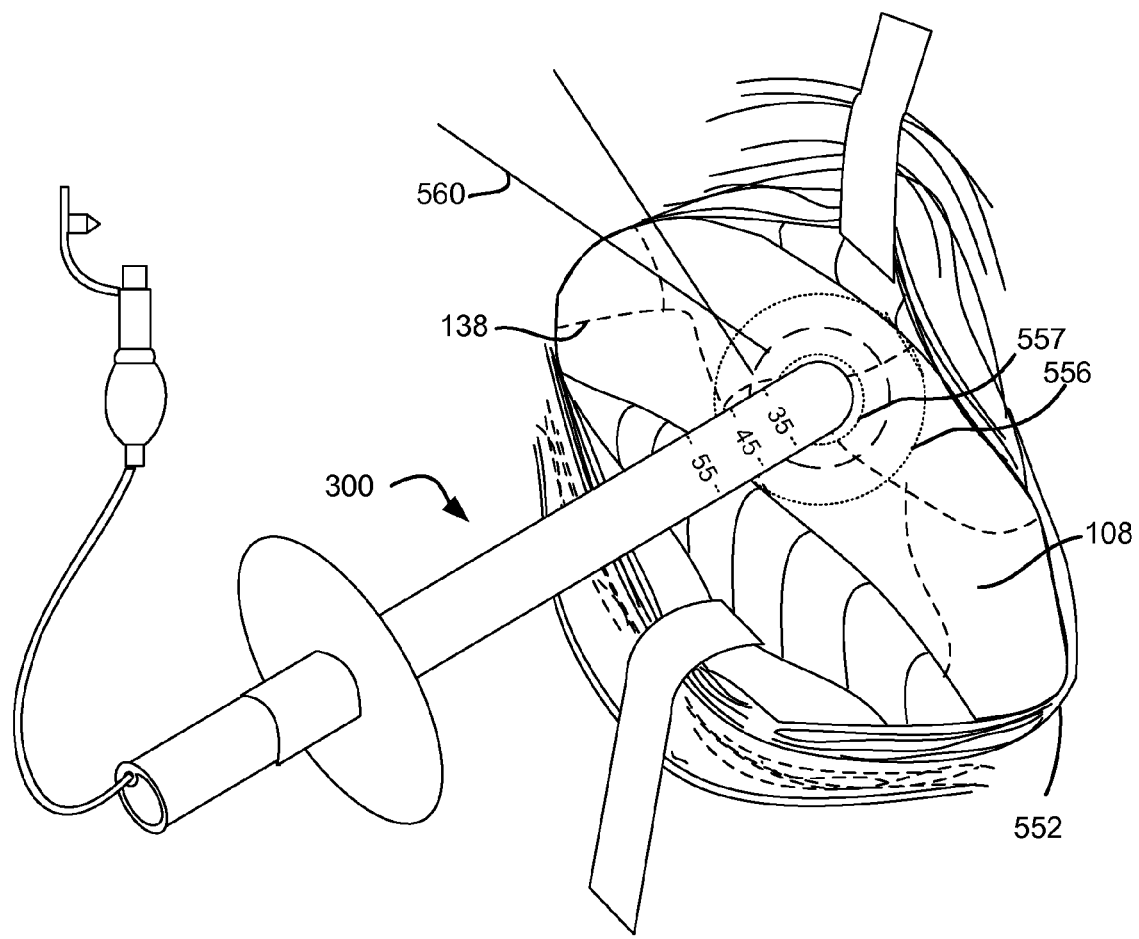
FIG. 5C illustrates the second part of the procedure of the accelerated two-phase pneumostomy technique of FIG. 5A.

As before, the pneumostomy catheter 300 should be inserted until the distal tip of the pneumostomy catheter 300 and the entirety of pneumoplasty balloon 306 are located within the parenchymal tissue. FIG. 5C illustrates the insertion of pneumostomy catheter 300 through the hole 557 in the center of polyglactin mesh torus 556 and through the parietal membrane 108 and visceral membrane 138. As described above, a purse string suture may be placed in the visceral membrane in addition to any suture of anchoring device that may be introduced to hold the visceral membrane to the parietal membrane. Where a mesh is used, the mesh is provided with a central opening which constrains the aperture through the visceral membrane without the use of a purse-string suture. Where the technology used to form the adhesion/pleurodesis does not constrain the opening through the visceral membrane with a two-dimensional structure, a purse-string suture may be useful around the opening in the visceral membrane. The purse-string suture 560 may be tightened prior to inflation of pneumoplasty balloon 306.

Referring again to FIG. 5A, at step 536, after pneumoplasty balloon 306 is located within the parenchymal tissue, a saline, air or water-filled syringe is connected to the coupling of the pneumostomy catheter and the pneumoplasty balloon is inflated as in the first technique. At step 538, after the pneumoplasty balloon 306 is inflated, the incision 552 (FIG. 5C) through the chest wall is closed around the pneumostomy catheter 300 using one or more sutures as necessary. A suture technique suitable for a straight incision is preferred over a purse-string suture. Flange 308 is then pushed against the skin of the chest and secured and dressed as in the two-phase technique. (see FIG. 4E and accompanying text).

The patient is provided with the same postoperative treatment as with the two-phase technique. When the physician considers that the pneumostoma has healed adequately, the pneumostomy catheter 300 is removed and the pneumostoma is inspected. The physician will then verify the size of the pneumostoma and provide a pneumostoma management device (PMD) of the appropriate size. The application of the PMD to the pneumostoma upon removal of pneumostomy catheter 300 is described in more detail with respect to FIGS. 8A and 8B, below.

Percutaneous Approach for Two-Phase Pneumostomy Techniques

The two-phase pneumostomy techniques described in FIGS. 4A-4F and 5A-5C and accompanying text may be performed, in whole or in part, using a percutaneous approach. In an exemplary procedure, a catheter is introduced to the pleural cavity using a technique such as the Seldinger technique. A needle is passed percutaneously into the pleural cavity. A guidewire is placed into the pleural cavity through the needle. The needle is then removed. A catheter is then percutaneously introduced into the pleural cavity over the guidewire. The catheter is guided fluoroscopically to the desired position for creating a pleurodesis between the visceral and parietal membranes. The catheter delivers an agent or device for forming an adhesion/pleurodesis between the visceral and parietal membranes at the desired location. The device may be, for example, an adhesive, adhesive mesh, tissue welding device, pleurodesis agent or other agent or device for bonding the visceral and parietal membranes to each other in an acute manner. In the second step of the technique, the pneumostomy catheter is introduced through the adhesion/pleurodesis into the lung. The introduction of the pneumostomy catheter may also be carried out percutaneously. The introduction of the pneumostomy catheter may be performed in a separate procedure (two-phase technique) or in the same procedure (accelerated two-phase technique) depending upon the technology used to form the adhesion/pleurodesis.

As part of the percutaneous approach a percutaneous catheter may be used to apply energy, such as RF energy, to weld the visceral and parietal membranes to each other in an acute manner. The catheter is introduced to the pleural cavity using a technique such as the Seldinger technique and guided to the desired site of the pleurodesis using e.g. fluoroscopic visualization. The catheter then heats the membranes to an adequate temperature using directed energy to sufficiently denature the collagen and/or other connective tissue fibers. In a preferred embodiment, RF energy is used as the heat source. The catheter then applies a vacuum to the parietal and visceral membranes, pushing them into contact, and allowing the partially denatured fibers of the parietal and visceral membrane to contact one another, mingle and bind to each other.

Single-Phase Pneumostomy Technique

Figure 6A:
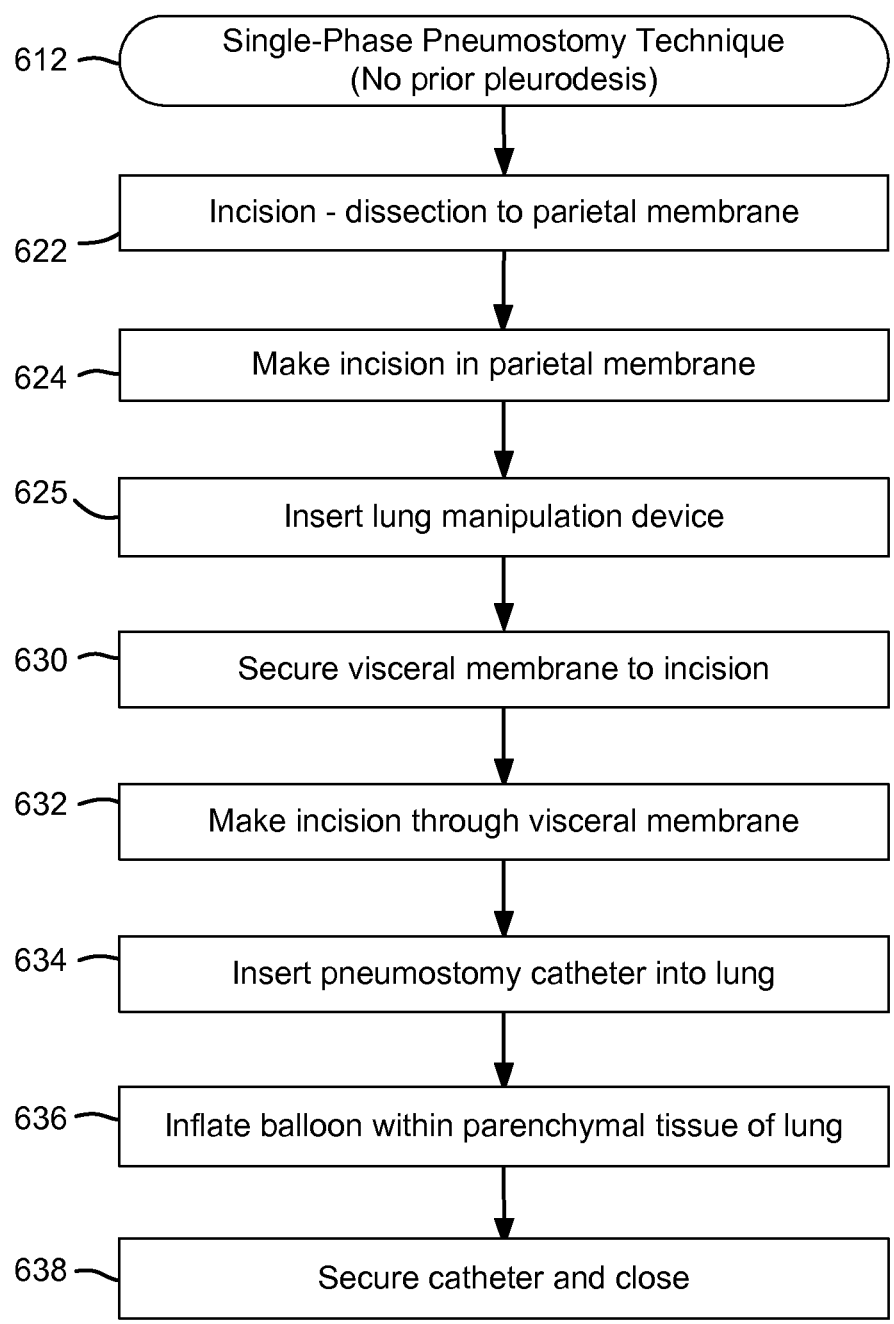
FIG. 6A shows the steps of a single-phase pneumostomy technique in accordance with an embodiment of the present invention.

FIG. 6A is a flowchart showing the steps of the single-phase pneumostomy technique. This technique is similar to the accelerated two-phase technique 512 with the exception that no interpleural seal is created prior to entering the pleural space and lung. Because no preliminary interpleural seal is created, the lung may deflate during the procedure resulting in a temporary pneumothorax. The technique 612 begins with the patient given a general anesthetic, intubated and ventilated via the other lung. A chest tube is inserted into the pleural cavity in a standard manner at a location away from the target area to assist with re-inflation of the lung after the procedure. At step 622, an incision is opened at the target location and the physician performs dissection to expose the parietal membrane 108. A larger incision may be required than in the first two techniques to permit access to the pleural cavity. In some cases a minithoracotomy may be performed, in other cases, a smaller rib resection may be used instead of a minithoracotomy. In other cases, sufficient access may be obtained by retracting the ribs without resection. At step 624, a small incision is made in the parietal membrane at the target location. The incision in the parietal membrane allows air to enter the pleural space causing the lung to shrink away from the parietal membrane 108. At step 625, a lung manipulation device is inserted through the incision to grasp the visceral membrane of the lung and approximate it to the opening in the parietal membrane. A pleurodesis agent may be applied between the visceral membrane and parietal membrane surrounding the opening at this time to promote pleurodesis after the procedure.

Figure 6B:
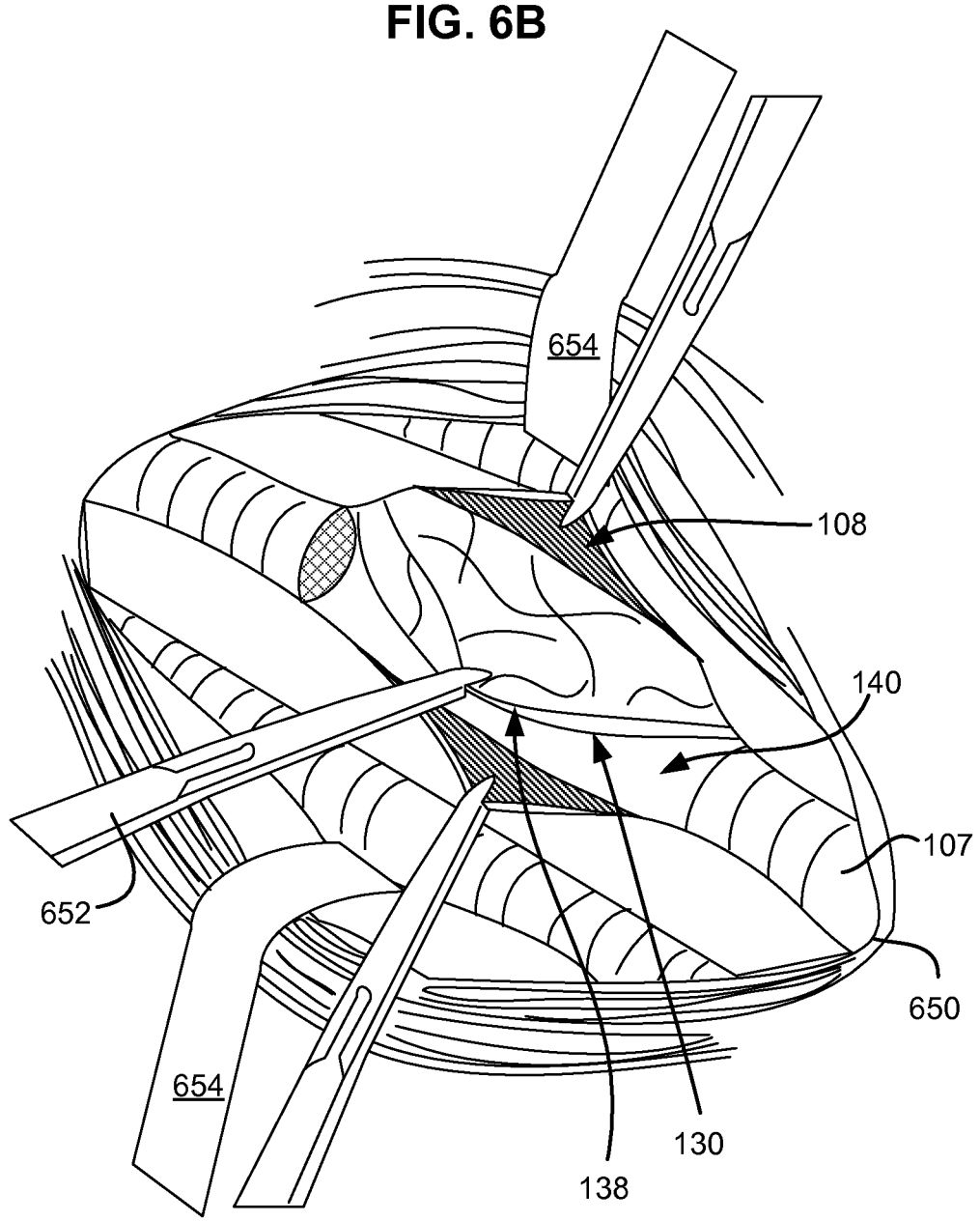
FIGS. 6B-6C illustrate steps of the single-phase pneumostomy technique of FIG. 6A.

FIG. 6B shows a minithoracotomy in which a section of a rib 107 has been resected to provide access to the pleural cavity 140 through an incision 650. Dissection is used to expose the parietal membrane 108. The parietal membrane 108 has been retracted around opening 650 to provide access to the lung 130. One or more retractors 654 may be used to aid with visualization of the pleural cavity 140. Note that the lung 130 has pulled back from the parietal membrane because air has entered the pleural cavity 140. A lung manipulation device 652 is, therefore, inserted through the opening 650 to manipulate the visceral membrane 138 of the surface of lung 130. The lung manipulation device 652 may be a blunt forceps or a suction device or similar tool designed to grip the visceral membrane without tearing the visceral membrane. One or more of the pleurodesis agents discussed above may be applied to the parietal membrane 108 or visceral membrane at this time to promote pleurodesis formation following the procedure.

Referring again to FIG. 6A, at step 630, the physician may choose to secure the visceral membrane 138 to the parietal membrane 108 around the opening into the pleural cavity 140. The lung manipulation device 652 is used to approximate the visceral and parietal membranes. When the membranes are approximated, the visceral membrane 138 is fixed to the parietal membrane 108 using several sutures distributed around the perimeter of the opening in the parietal membrane. Although sutures are preferred, other materials and methods may be used, such as, e.g. adhesives, staples, clips, tissue anchors and the like.

At step 632, the physician creates a small incision through the visceral membrane. The surgeon may additionally put a purse-string suture around the site of the incision. At step 634, the physician inserts the distal tip of the pneumostomy catheter 300 through the incision into the lung. If the visceral membrane was not secured to the parietal membrane at step 630, it will be necessary to provide counter-pressure with the lung manipulation tool during introduction of the pneumostomy catheter 300 into the lung. As before, the pneumostomy catheter 300 should be inserted until the distal tip of the pneumostomy catheter 300 and the entirety of pneumoplasty balloon 306 is located within the parenchymal tissue of the lung. The purse-string suture may be tightened prior to inflation of pneumoplasty balloon 306. At step 636, after the pneumoplasty balloon 306 is located within the parenchymal tissue, a saline, water or air-filled syringe is connected to the coupling of the pneumostomy catheter 300 and the pneumoplasty balloon 306 is inflated as in the first technique.

Figure 6C:
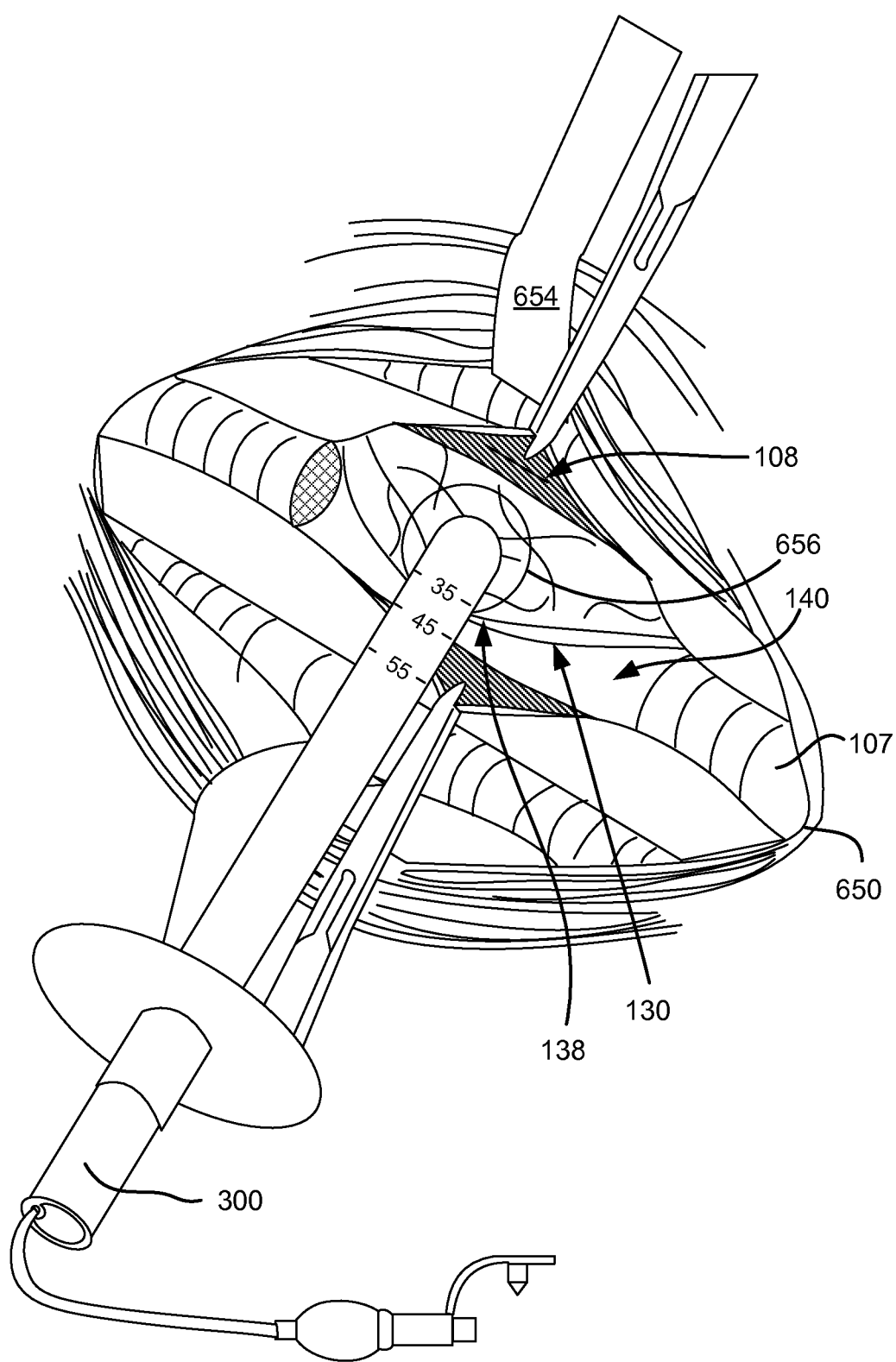

FIG. 6C illustrates a pneumostomy catheter 300 inserted through the visceral membrane 138 into the parenchymal tissue of lung 130. A purse-string suture 656 is shown around the pneumostomy catheter 300. The lung 130, shown in FIG. 6C, was not fixed to the parietal membrane prior to insertion of pneumostomy catheter 300. However, now that the pneumostomy catheter is secured within the lung by the pneumoplasty balloon and the purse-string suture, the visceral membrane may be approximated to the parietal membrane during the closing of the opening.

Referring again to FIG. 6A, at step 638, after the pneumoplasty balloon 306 is inflated, the incision through the chest wall is closed around the pneumostomy catheter using one or more sutures as necessary. If the pleural membranes were not previously secured to one another, the visceral membrane is drawn into contact with the parietal membrane using the pneumostomy catheter 300. After the opening through the chest wall has been closed, flange 308 is pushed against the skin of the chest wall and secured as in the two-phase technique (see FIG. 4E and accompanying text). Slight tension is applied to the pneumostomy catheter 300 prior to securing flange 308 to ensure that the pleural membranes are in good contact with each other. The pneumostoma site is dressed. At this point, the chest should be sealed and there should be little air leaking into the pleural cavity at the site of the pneumostomy catheter. However, some air may continue to leak until a pleurodesis forms between the visceral and parietal membranes surrounding the pneumostomy catheter. The chest drain should, therefore, be left in to apply negative pressure to the pleural cavity to re-inflate and then maintain the inflation of the lung until there is no longer any leakage into the pleural cavity. This may take from one to three days. After any air leakage into the pleural cavity is resolved, the chest tube is removed. The pneumostomy catheter is left in place from one to two weeks while the pneumostoma heals as in the two-phase pneumostomy techniques.

Although this procedure has been illustrated using a minithoracotomy for access to the lung, other approaches may be used. For example, the procedure may also be performed in a less invasive fashion by entering the pleural cavity through the intercostal space and retracting the ribs rather than removing a section of rib. The procedure may also be performed using a minimally invasive approach under thorascopic guidance.

The patient is provided with the same postoperative treatment as with the two-phase pneumostomy techniques. When the physician considers that the pneumostoma has healed adequately, the pneumostomy catheter is removed and the pneumostoma is inspected. The physician will then verify the size of the pneumostoma and provide a pneumostoma management device (PMD) of the appropriate size. The application of the PMD to the pneumostoma upon removal of pneumostomy catheter is described in more detail with respect to FIGS. 8A and 8B, below.

Percutaneous Single-Phase Pneumostomy Technique

FIG. 7A is a flowchart showing the steps of a percutaneous single-phase pneumostomy technique 712. This pneumostomy technique is similar to the accelerated two-phase technique 512 with the primary difference that no prior pleurodesis is formed. Because no pleurodesis is formed in this technique, a different technology is utilized to deliver the pneumostomy catheter into the lung. The pneumostomy catheter is assembled with a percutaneous insertion tool and delivered into the parenchymal tissue of the lung through the pleural cavity. Tension on the pneumostomy catheter after the balloon is inflated serves to hold the visceral and parietal pleural membranes in opposition and seals any leakage during pneumostoma formation. A chest tube may be inserted prior to the procedure in order to extract any air that may leak into the pleural cavity during the procedure.

Figure 7B:
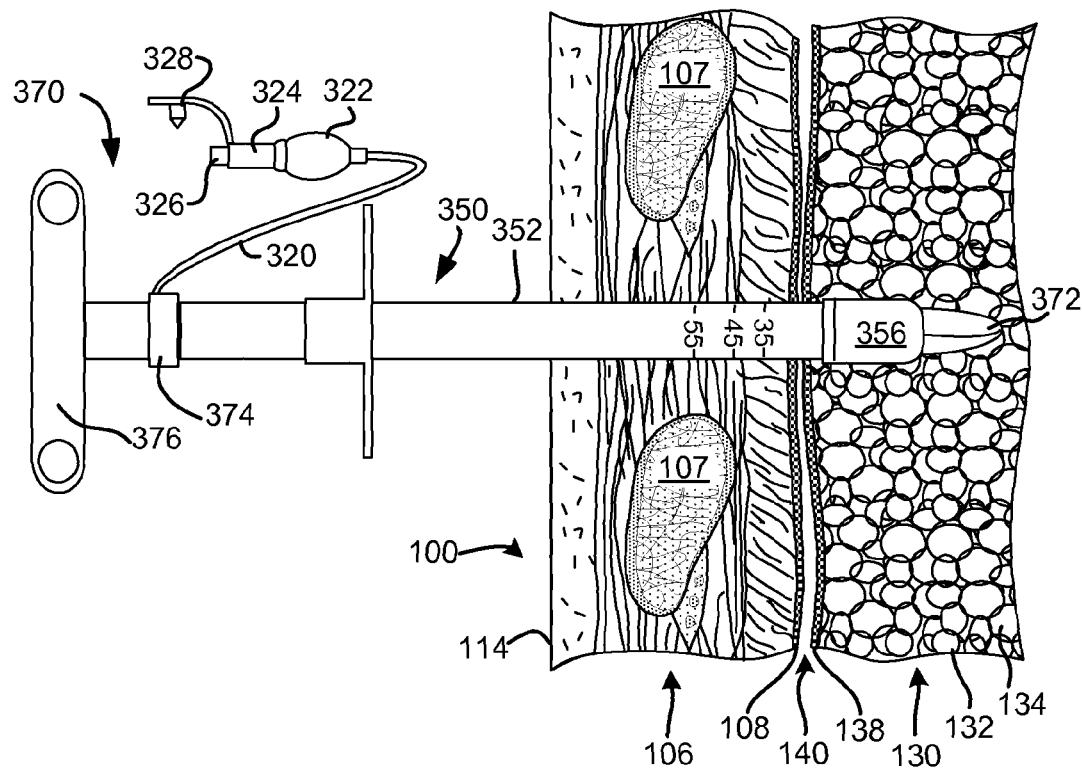
FIGS. 7B-7C illustrate steps of the percutaneous single-phase pneumostomy technique of FIG. 7A.

Referring again to FIG. 7A, prior to the procedure, the patient is prepared using local anesthesia at the target site in addition to a sedative or general anesthesia. A chest tube is preferably inserted into the pleural cavity as a prophylactic measure. At step 722, an incision is opened at the target location and the physician performs dissection to expose the parietal membrane. At step 724, a material or device may be optionally delivered to the localized area surrounding the target location to promote pleurodesis between the visceral and parietal membranes after the procedure. One or more of the pleurodesis agents discussed above may be used in order to promote pleurodesis formation following the procedure, however, it is not expected that the pleurodesis will form during the procedure itself. At step 726, the physician assembles the pneumostomy catheter 350 with the percutaneous insertion tool 370 as described in FIGS. 3D and 3E and accompanying text. At step 734, the physician inserts the pneumostomy catheter 350 into the lung through the parietal and visceral membranes using the percutaneous insertion tool 370. As before, the pneumostomy catheter 350 should be inserted until the distal tip of the pneumostomy catheter 350 and the entirety of pneumoplasty balloon 356 are located within the parenchymal tissue. FIG. 7B illustrates the insertion of pneumostomy catheter 350 through the parietal membrane 108 and visceral membrane 138 through the pleural cavity 140. Because there is no pleurodesis between the parietal membrane 108 and visceral membrane 138, a small amount of air may leak into the pleural cavity around tube 352. However, the chest tube should be able to extract the small amount of air and the lung 130 will remain inflated and pushed against the chest wall 106.

Figure 7C:
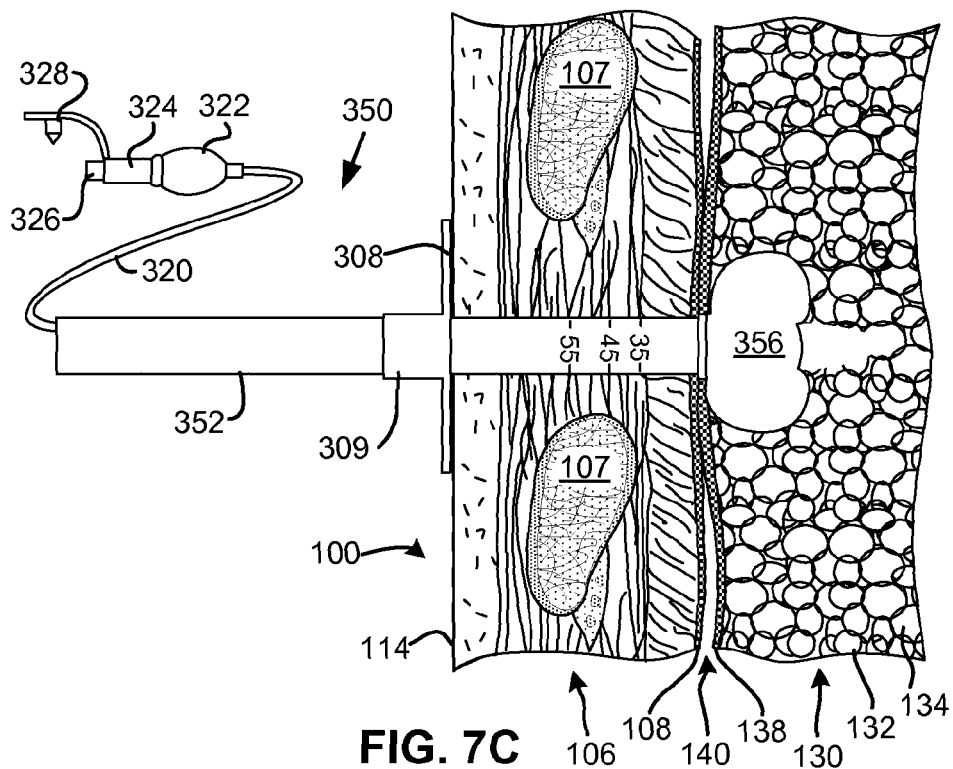

Referring again to FIG. 7A, at step 736, after pneumoplasty balloon 356 is located within the parenchymal tissue 132 the pneumoplasty balloon 356 is inflated as in the first technique. At step 737, the percutaneous insertion tool 370 is removed from the main lumen of pneumostomy catheter 350 (this step may alternatively be performed before balloon inflation). At step 738, after the pneumoplasty balloon 356 is inflated, flange 308 is pushed against the skin of the chest as shown in FIG. 7C. Tension is applied to tube 352 of pneumostomy catheter 350 drawing the lung 130 towards thoracic wall 106 and bringing the parietal membrane 108 and visceral membrane 138 into contact. The contact between the parietal membrane 108 and visceral membrane 138 should reduce or eliminate any air leak around tube 352. Moreover, the contact between the parietal membrane 108 and visceral membrane 138 should mature into a pleurodesis during the postoperative period. The balloon 356 and tube 352 may be coated and/or impregnated with a pleurodesis agent to promote the formation of the pleurodesis. After the tension is applied to tube 352, pneumostomy catheter 350 is secured and dressed as in the two-phase technique. (see FIG. 4E and accompanying text).

The patient is provided with the same postoperative treatment as with the two-phase technique. When the physician considers that the pneumostoma has healed adequately, the pneumostomy catheter 350 is removed and the pneumostoma is inspected. The physician will then verify the size of the pneumostoma and provide a pneumostoma management device (PMD) of the appropriate size. The application of the PMD to the pneumostoma upon removal of pneumostomy catheter 350 is described in more detail with respect to FIGS. 8A and 8B, below.

Referring again to FIG. 7A, additional tools or devices may be used at step 724 to stabilize the parietal and visceral membranes in the region surrounding the target location for the pneumostoma. Such tools and/or devices may be used to stabilize the visceral and parietal membranes before insertion of the pneumostomy catheter 350. They may optionally remain in place after insertion of the pneumostomy catheter 350. In some cases, the devices may be implantable and/or absorbable such that they may be left in place and be absorbed by the body over time.

FIG. 7D shows an example of a lung retraction tool 740 inserted percutaneously through thoracic wall 106 into the lung 130 prior to insertion of the pneumostomy catheter 350. Refraction tool 740 comprises a thin tubular shaft 742 in which is received a rod 744. At the proximal end of shaft 742 is mounted an actuator 746. Operation of actuator 746 generates reciprocal movement of rod 744 and shaft 742.

At the distal end of shaft 742 is mounted an anchor 748. Anchor 748 has a first low-profile configuration (not shown) in which it has approximately the same diameter as shaft 742. Anchor 748 may be readily introduced percutaneously into the lung in this first low-profile configuration. After anchor 748 is positioned within the lung, actuator 746 is operated to move rod 744 within shaft 742. The movement of rod 744 relative to shaft 742 causes anchor 748 to reconfigure into a second configuration (as shown) in which it extends laterally from the diameter of shaft 742. In this second configuration (as shown), anchor 748 is designed to engage the visceral membrane 138 of the lung 130.

After anchor 748 has been deployed to the second configuration, a slight tension may be applied to lung refraction tool 740 to draw visceral membrane 138 into contact with parietal membrane 108. Lung retraction tool 740 may then be secured into position using a locking flange 747 mounted on shaft 742. Lung retraction tool 740 is preferably positioned laterally displaced and adjacent the target site for the pneumostoma in the same intercostal space. A second lung refraction tool 740 may be positioned on the other side of the target site with sufficient space between the lung retraction tools for introduction of pneumostomy catheter 350. After introduction and deployment of the pneumostomy catheter (as described above), the anchor 748 is returned to the first low-profile configuration and the lung retraction tool(s) is (are) removed.

A number of different devices may be delivered percutaneously to stabilize the visceral and parietal membranes, including for example, suture, clips, staples, adhesive and/or adhesive patches. FIG. 7E shows an example of a lung anchor 750 inserted percutaneously through thoracic wall 106 into the lung 130 prior to insertion of the pneumostomy catheter 350. Lung anchor 750 comprises an elongate body 752. At the distal end of body 752 is anchor head 758. Along the elongated body 752 are arrayed a plurality of barbs 754 oriented so as to prevent distal movement of elongate body 752 through tissue in the direction of anchor head 758.

Lung anchor 750 is inserted into a thin walled needle/cannula 760 for insertion through the chest wall. Needle/cannula 760 holds anchor head 758 in a low profile configuration during introduction into lung 130. When anchor head 758 is correctly positioned within the lung 130, needle/cannula 760 is withdrawn. Anchor head 758 springs into a wide profile configuration designed to engage the visceral membrane of the lung—see anchor head 758a. After needle/cannula 760 has been withdrawn, barbs 754 are also able to engage the tissue of chest wall 130. As light tension may be applied to elongate body 752 to draw visceral membrane 138 into contact with parietal membrane 108, barbs 754 engage the tissue of chest wall 130 to maintain the tension in elongate body 752. One or more lung anchors 750 may be introduced adjacent the target site for the pneumostoma in the same intercostal space to stabilize the visceral and parietal membranes during insertion of pneumostomy catheter 350.

Lung anchor 750 may be made from biocompatible metals and/or polymers. In particular lung anchor 750 may be made from a superelastic metal, for example nitinol. Alternatively, lung anchor 750 may be made of an absorbable material, for example, polyglactin. Where the anchoring device is made of an absorbable material it may be left in place and absorbed following the introduction and securing or pneumostomy catheter 350.

Figure 7F:
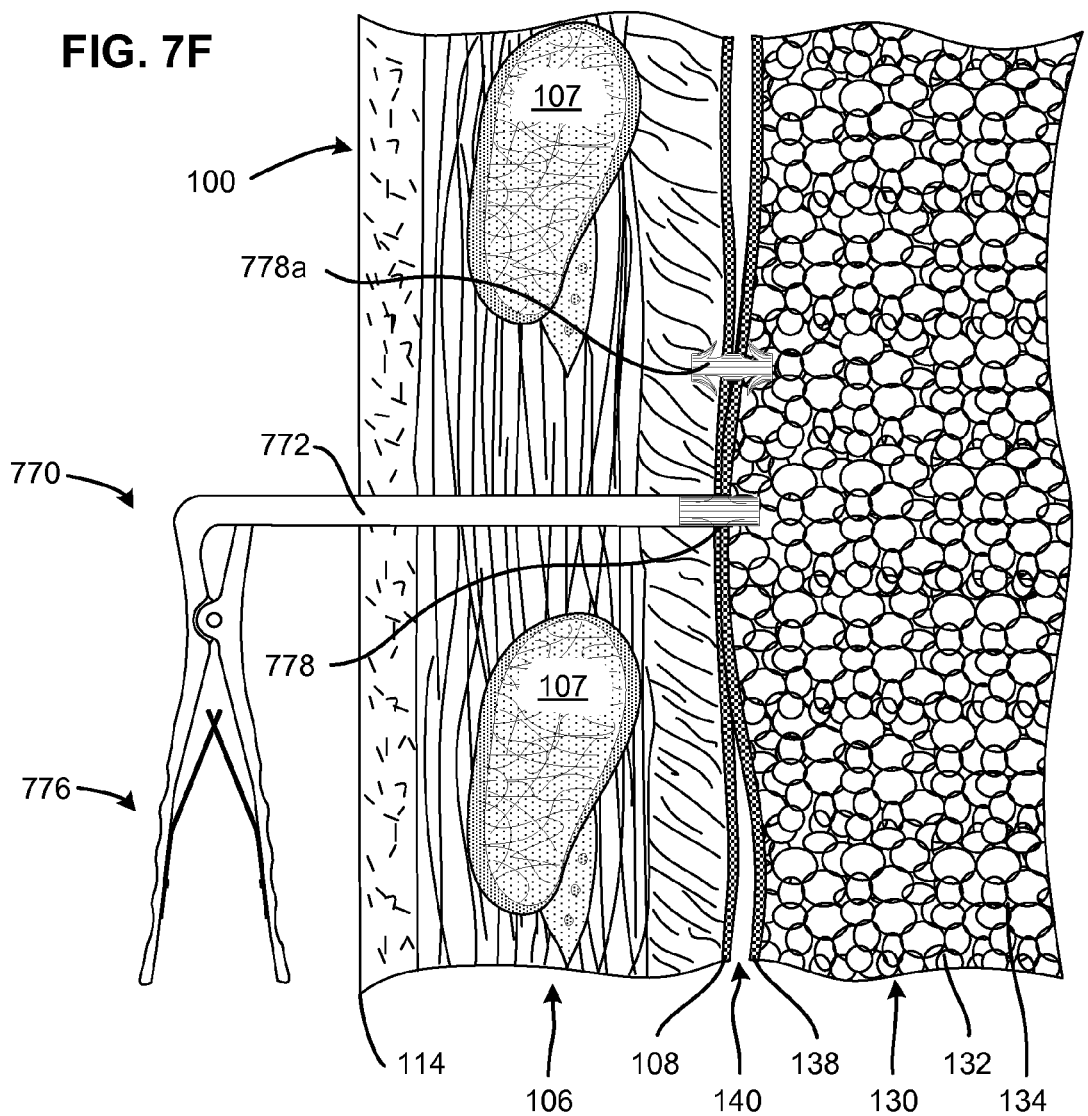
FIGS. 7F-7H illustrate a lung anchor and applicator for use in pneumostomy procedures in accordance with embodiments of the present invention.
Figure 7G:
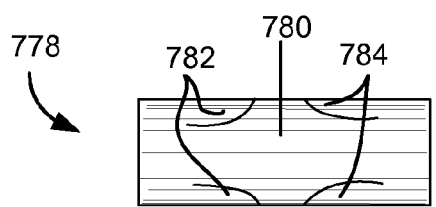
Figure 7H:
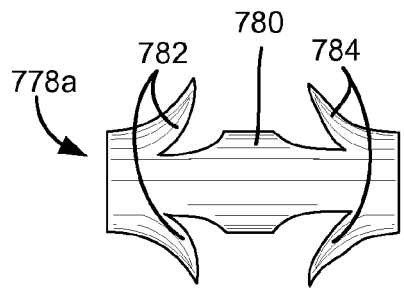

FIGS. 7F-7H illustrate an alternative lung anchor 778 which may be used to stabilize the visceral membrane 138 and parietal membrane 108 prior to and during the pneumostomy procedure. As shown in FIG. 7F, lung anchor 778 is implanted with an applicator 770. Applicator 770 has a thin tubular shaft 772 in which is received lung anchor 778. Shaft 772 is inserted percutaneously until lung anchor 778 is correctly positioned. At the proximal end of shaft 772 is mounted an actuator 776. Operation of actuator 776 operates to eject lung anchor 778 from shaft 772 into tissue adjacent the distal end of shaft 772 in the manner of a surgical staple or clip applier. Actuator 776 is then removed leaving the lung anchor in position to stabilize the parietal membrane 108 and visceral membrane 138—see deployed anchor 778a of FIG. 7F. One or more lung anchors 778 are preferably positioned laterally displaced and adjacent the target site for the pneumostoma in the same intercostal space prior to the pneumostomy procedure.

FIG. 7G shows an enlarged view of lung anchor 778. Lung anchor 778 includes a longitudinal body 780, a first set of retainers 782 and a second set of retainers 784. As shown in FIG. 7G, the retainers 782, 784 lie flat against the body 780 in the undeployed configuration. The lung anchor is placed in applicator 770 in this undeployed configuration. After insertion into the tissue, retainers 782, 784 move away from body 780 to engage tissue as shown in FIG. 7G. FIG. 7H shows a lung anchor 778a with retainers 782, 784 in the deployed configuration. Retainers 782, 784 are oriented in opposite directions so that one set of retainers may engage the parietal membrane 108 and the other set may engage the visceral membrane 138 and thereby secure the two pleural membranes to one another.

The transition from undeployed configuration to deployed configuration may be achieved in a number of ways. For example, lung anchor 778 may be mechanically constrained in the undeployed configuration by tubular shaft 772 such that, when released, retainers 782, 784 spring out into the deployed configuration. Alternatively, lung anchor 778 may be formed of a shape memory polymer or metal such that upon insertion into the tissue, the material of the anchor transitions from the undeployed configuration 778 (FIG. 7G) to the stored deployed configuration 778a (FIG. 7H). Lung anchor 778 may be made from biocompatible metals and/or polymers. In particular lung anchor 778 may be made from a superelastic metal, for example, nitinol. Alternatively, lung anchor 778 maybe made of an absorbable material, for example polyglactin. Where the anchoring device is made of an absorbable material it may be left in place and absorbed following the pneumostomy procedure.

Pneumostoma Management Device

As described above, a pneumostoma may be created to treat the symptoms of chronic obstructive pulmonary disease. A patient is typically provided with a pneumostoma management system to protect the pneumostoma and keeps the pneumostoma open on a day-to-day basis. In general terms, a pneumostoma management device ("PMD") comprises a tube which is inserted into the pneumostoma and an external component which is secured to the skin of the patient to keep the tube in place. Gases escape from the lung through the tube and are vented external to the patient. The pneumostoma management device may, in some, but not all cases, include a filter which only permits gases to enter or exit the tube. The pneumostoma management device may, in some, but not all cases, include a one-way valve which allows gases to exit the lung but not enter the lung through the tube.

Figure 8A:
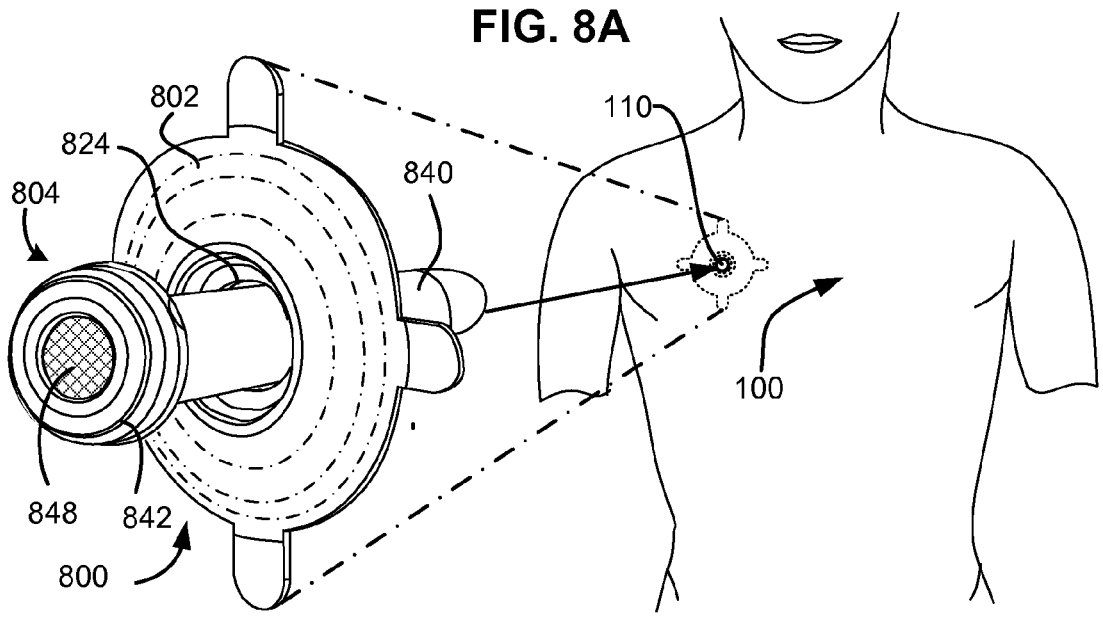
FIGS. 8A and 8B show use of a pneumostoma management device after removal of a pneumostomy catheter in accordance with any one of the above procedures.
Figure 8B:
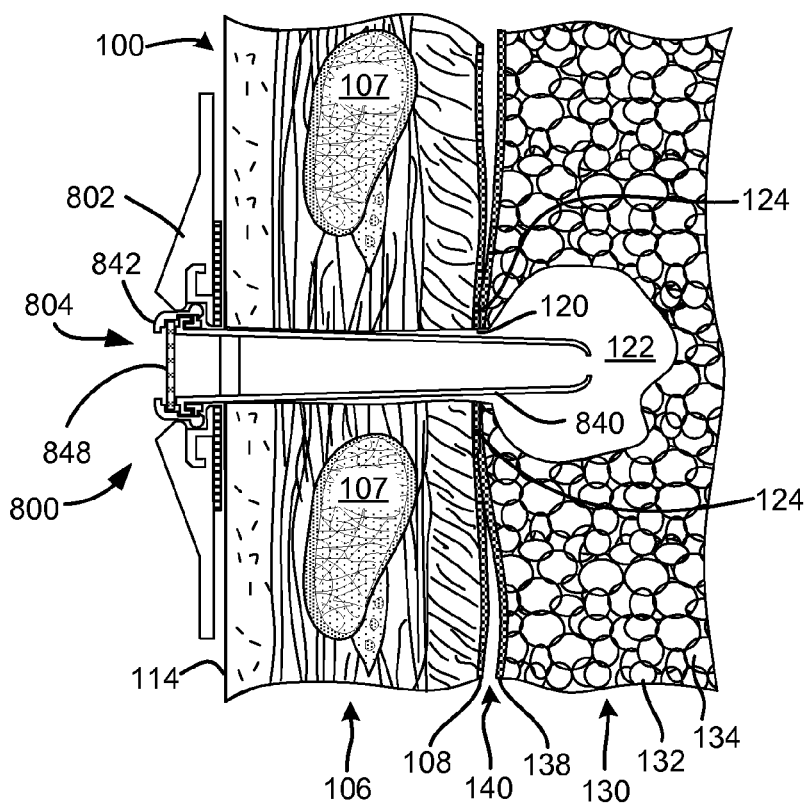

FIGS. 8A and 8B illustrate application of a pneumostoma management device ("PMD") 800 to a pneumostoma 110 formed in accordance with a pneumostomy procedure of the present invention. PMD 800 includes a chest mount 802 which may be mounted to the chest 100 of the patient and a pneumostoma vent 804 which is fitted to the chest mount 802. Pneumostoma vent 804 is mounted through an aperture 824 in chest mount 802. Chest mount 802 has a first coupling that engages a second coupling of the pneumostoma vent to releasably secure the pneumostoma vent 804 to the chest mount 802. A patient will typically wear a PMD at all times after formation of the pneumostoma, and, thus, the materials should meet high standards for biocompatibility. A pneumostoma management device and system for use with such a pneumostoma management device is described in provisional patent application 61/032,877 entitled "Pneumostoma Management System And Methods For Treatment Of Chronic Obstructive Pulmonary Disease" filed Feb. 29, 2008, which is incorporated herein by reference.

Pneumostoma vent 804 includes a tube 840 sized and configured to fit within the channel of pneumostoma 110. Tube 840 is stiff enough that it may be inserted into pneumostoma 110 without collapsing. Tube 840 may be round, oval or some other shape depending on the shape of the pneumostoma. Over time a pneumostoma may constrict and the PMD 800 is designed to preserve the patency of the channel 120 of pneumostoma 110 by resisting the natural tendency of the pneumostoma to constrict. Pneumostoma vent 804 includes a cap 842 and a hydrophobic filter 848 over the proximal end of tube 840. Hydrophobic filter 848 is positioned and mounted such that material passing in and out of pneumostoma 110 through tube 840 of pneumostoma vent 804 must pass through hydrophobic filter 848.

Tube 840 of pneumostoma vent 804 is sufficiently long that it can pass through the thoracic wall 106 and into the cavity 122 of a pneumostoma inside the lung 130. Pneumostoma vent 804 is not, however, so long that it penetrates so far into the lung 130 that it causes injury. The length of tube 840 required for a pneumostoma vent 804 varies significantly between different pneumostomas. A longer tube 840 is usually required in patients with larger amounts of body fat on the chest. A longer tube 840 is usually required where the pneumostoma is placed in the lateral position 112 rather than the frontal position 110. Because of the variation in pneumostomas, pneumostoma vents 804 are manufactured having tubes 840 in a range of sizes. Tube 840 may be from 30 to 180 mm in length and from 5 mm to 20 mm in diameter depending on the size of a pneumostoma. A typical tube 840 may be between 40 mm and 100 mm in length and between 8 mm and 12 mm in diameter. When the pneumostomy catheter is removed, the physician should gauge the size of the pneumostoma that has been created for the particular patient and provide a pneumostoma vent 804 having a tube 840 of appropriate length for the pneumostoma. The markings on the side of the pneumostomy catheter 300 may also assist the physician in determining the approximate length of pneumostoma vent 804.

To use PMD 800, chest mount 802 is first positioned over a pneumostoma and secured with adhesive to the skin 114 of the patient. Chest mount 802 may be positioned by manual alignment of the aperture 824 of chest mount 802 with the aperture of the pneumostoma 110. Alternatively, a pneumostoma vent 804 or an alignment tool may be used to help align the chest mount 802. As shown in FIG. 8B, the low profile of chest mount 802 allows it to be inconspicuously positioned on the chest 100 of a patient in either of the frontal 110 or lateral 112 locations illustrated in FIG. 1A. Cap 842 of pneumostoma vent 804 is received in a recess in chest mount 802 such that tube 840 is secured inside the channel 120 of the pneumostoma 110.

The removal of the pneumostomy catheter 300 and application of the first PMD 800 will be performed by the physician. However, the patient will subsequently be responsible for applying and removing the chest mount 802 and the insertion, removal and disposal of pneumostoma vent 804. The pneumostoma management device 800 is preferably provided as part of a system which assists the patient in utilizing the chest mount and pneumostoma vent and keeping the pneumostoma clean and free of irritation/infection while trapping sputum, mucous and other discharge. The patient will exchange one pneumostoma vent 804 for another and dispose of the used pneumostoma vent 804. Pneumostoma vent 804 will be replaced periodically, such as daily, or when necessary. The patient will be provided with a supply of pneumostoma vents 804 of the appropriate size by a medical practitioner or by prescription. Chest mount 802 will also be replaced periodically, such as weekly, or when necessary. The patient will also be provided with a supply of chest mount 802 by a medical practitioner or by prescription. A one week supply of pneumostoma vent 804 (such as seven pneumostoma vents 804) may be conveniently packaged together with one chest mount 802. Pneumostoma management devices of different designs as discussed in the previously referenced patent applications may also be used.

Alternative Pneumostomy Instruments

FIGS. 9A-E show alternative pneumostomy instruments for use in pneumostomy procedures in accordance with embodiments of the present invention. The instruments have an expanding mechanism (such as a balloon) for creating a cavity in the parenchymal tissue of the lung thereby engaging the parenchymal tissue and allowing the lung to be drawn towards the thoracic wall. The instruments have a tube connected to the expanding mechanism for drawing the expanding mechanism towards the chest wall and having a lumen to connect to the cavity in the parenchymal tissue. The instruments have a securing mechanism (such as a sliding flange) for securing the position of the expanding mechanism after applying tension to the tube. The function of the various components can be achieved in a variety of ways.

Figure 9A:
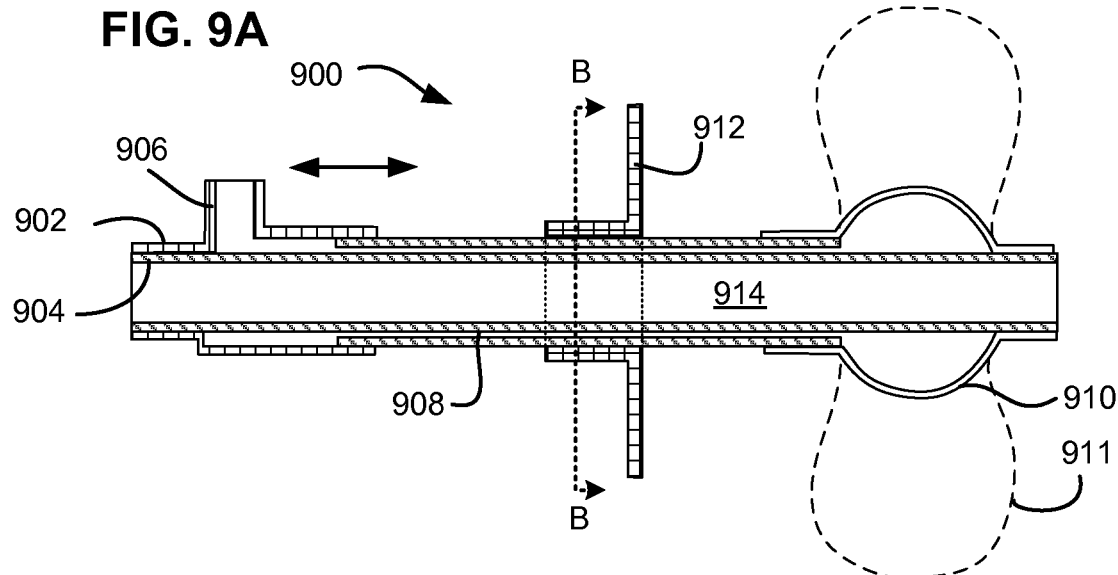
FIGS. 9A-9G show alternative pneumostomy instruments and accessories for use in pneumostomy procedures in accordance with embodiments of the present invention.
Figure 9B:
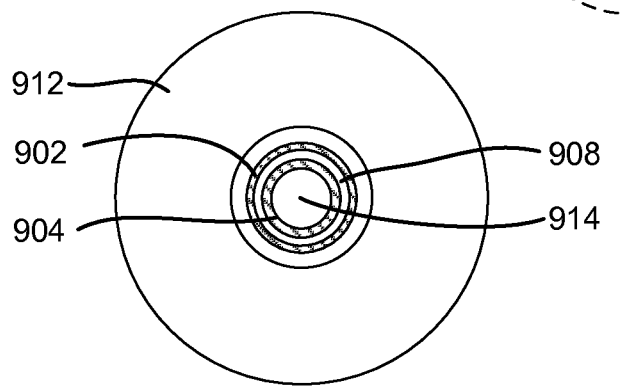

FIGS. 9A and 9B show different sectional views an alternative pneumostomy instrument 900 having an outer tube 902 and an inner tube 904 in a coaxial relationship. The inner tube is 904 connected to the outer tube 902 at the proximal end of the instrument by a fitting 906. An inflation lumen 908 is defined by the space between the inner tube 904 and outer tube 906. The inflation lumen 908 is sealed at the proximal end of the instrument 900 by the fitting 906. At the distal end, the inner tube 904 protrudes beyond the end of the outer tube 906. An inflatable pneumoplasty balloon 910 is connected between the end of the inner tube 904 and the end of the outer tube 906 as shown in FIG. 9A thereby sealing the distal end of the inflation lumen 908. Thus air, water or saline inserted through fitting 906 passes through inflation lumen 908 into pneumoplasty balloon 910 thereby inflating balloon 910 to the position shown by dotted line 911. An access flange 912 is provided in sliding engagement with the exterior of the outer tube 902. FIG. 9B shows a sectional view of pneumostomy instrument 900 along the line B-B of FIG. 9A. FIG. 9B shows outer tube 902, inner tube 904, inflation lumen 908 and main lumen 914. Pneumostomy instrument 900 is used in the same way as pneumostomy catheter 300 of FIGS. 3A through 3C with the exception that pneumostomy instrument 900 has no facility to be shortened after the pneumostomy procedure. Pneumostomy instrument 900 may also be used with a percutaneous insertion instrument 370 as shown in FIGS. 3D-3E.

Figure 9C:
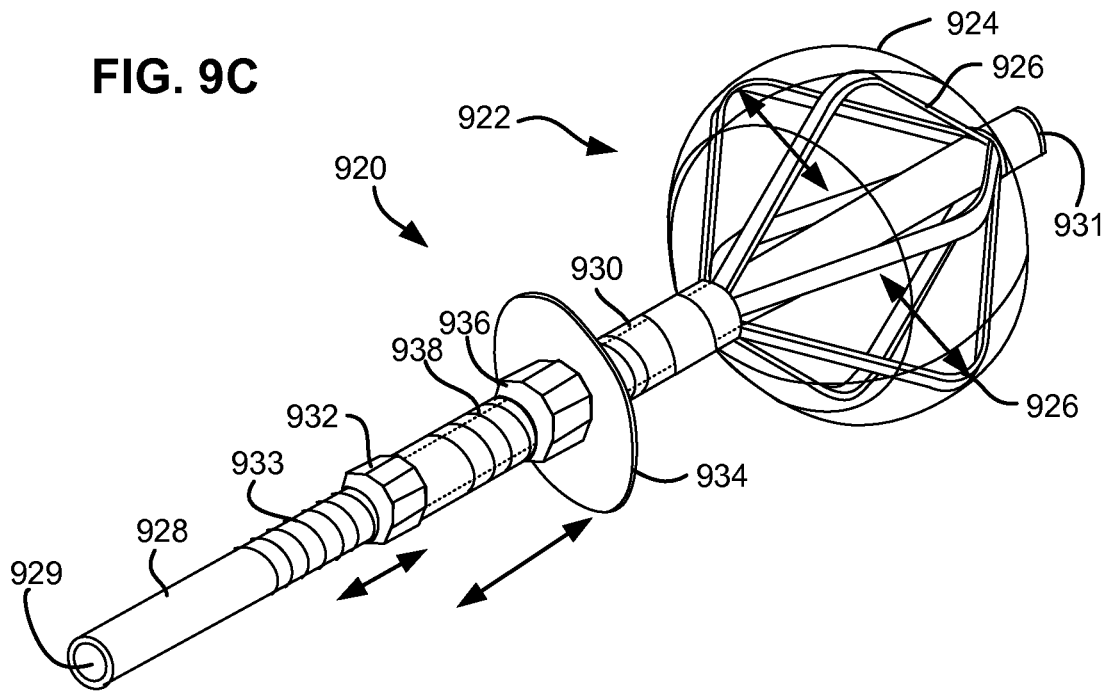

FIG. 9C shows a perspective view of an alternative pneumostomy instrument 920 that uses an expanding pneumoplasty mechanism instead of a pneumoplasty balloon. As shown in FIG. 9C, the expanding pneumoplasty mechanism 922, comprises a polymer skin 924 covering a flexible expanding cage formed of six bars 926. The distal end of each bar 926 is fixed to the distal end of inner tube 928 adjacent atraumatic distal tip 931. The proximal end of each bar 926 is fixed to the distal end of outer tube 930. Outer tube 930 is received over inner tube 928 and can slide relative to inner tube 928. At the proximal end of outer tube 930 is a threaded nut 932 which rides on threads 933 on the exterior of inner tube 928. Inner tube 928 comprises a main lumen 929 which runs from the proximal end to the distal end of pneumostomy instrument 920.

Expanding pneumoplasty mechanism 922 is expanded by turning nut 932 clockwise which drives nut 932 and outer tube 930 distally relative to inner tube 928. When outer tube 930 moves distally relative to inner tube 928, bars 926, which are initially approximately parallel to inner tube 928, bend outwards from inner tube 928 as shown. The bars 926 push polymer skin 924 outwards in the ball shape shown. Nut 932 may be provided with a stop to indicate when the expanding pneumoplasty mechanism 922 is fully expanded. Nut 932 may also be provided with a safety lock, such as a ratchet which locks the nut in position until removal of the pneumoplasty instrument is desired.

Pneumostomy instrument 920 includes an access flange 934 which slides on the exterior of outer tube 930 for engaging the chest of the patient. However, as shown in FIG. 9C, access flange 934 is also driven by a nut 936 which rides on threads 938 on the exterior of outer tube 930. Turning nut 936 clockwise drives access flange 934 distally thereby drawing the expanding pneumoplasty mechanism 922 closer towards the chest wall. Nut 936 may also be provided with a safety lock, such as a ratchet which locks the nut in position until removal of the pneumoplasty instrument is desired. Access flange 934 and its driving and locking mechanism may be substituted for access flange 912 or access flange 308.

Pneumostomy instrument 920 is used in the same way as pneumostomy catheter 300 of FIGS. 3A through 3C with the exceptions that expansion of expanding pneumoplasty mechanism 922 is by turning nut 932 rather than inflating a balloon and positioning of access flange 934 is by turning nut 936 rather then sliding and suturing. Pneumostomy instrument 920 may also be used with a percutaneous insertion instrument 370 as shown in FIGS. 3D-3E.

Figure 9D:
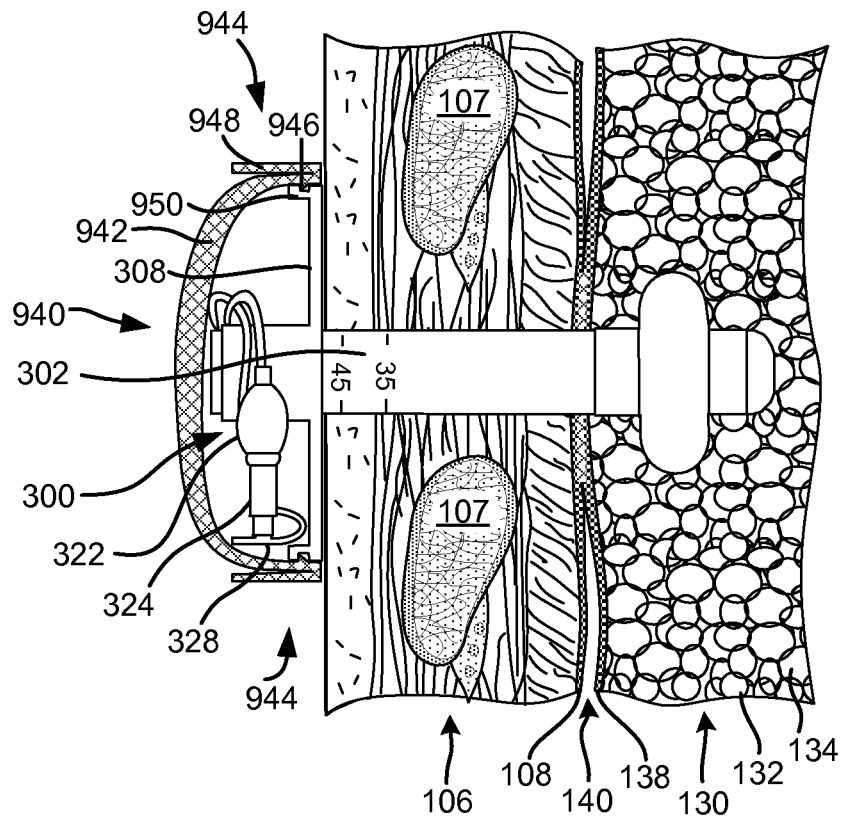
Figure 9E:
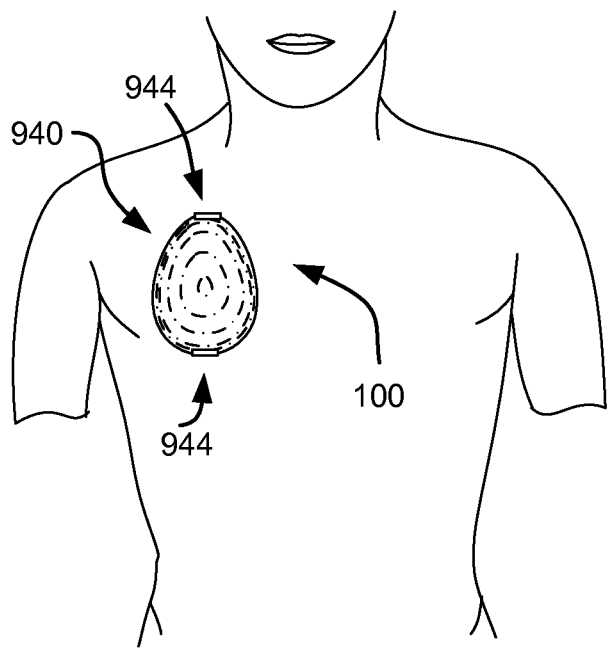

FIGS. 9D and 9E show sectional and perspective views respectively of a post-operative protective cover 940. Protective cover 940 includes dome 942 which is specially-shaped to protect the exterior components of the pneumostomy catheter 300 during the post-operative period in which a pneumostoma is healing. As shown in FIGS. 9D and 9E, dome 942 is pear-shaped to accommodate the pilot balloon 322, check valve 324 and cap 328. Flange 308 is shaped to fit snugly within cover 940, and, thus, is also pear-shaped. The contact between the inside edge of dome 942 and the raised lip 950 of flange 308 effectively seals the space between dome 942 and flange 308. Dome 942 should be relatively low-profile and smooth so as not to restrict movement of the patient or interfere with the patient's clothing.

Protective cover 940 has two clips 944 for engaging access flange 308. Each of clips 944 comprises a catch 946 for engaging a detent in raised lip 950 of flange 308. Each of clips 944 also has a release lever 948 for disengaging catch 946 from flange 308. In use, protective cover 940 can be clipped to flange 308 by pushing clips 944 into position over raised lip 950. Protective cover 940 is released by squeezing lever arms 948 towards dome 942. In other embodiments, protective cover 940 may be releasably secured to flange 308 using other suitable mechanisms or by a releasable adhesive. Alternatively, protective cover 940 may be secured to the chest 100 of the patient directly as shown in FIGS. 9F-9G.

Dome 942 is preferably made of a stiff hydrophobic material such that when protective cover 940 is in position over pneumostomy catheter 300, protective cover 940 prevents entry of water or other foreign matter into tube 302. Dome 942 is also designed to capture any discharge from tube 302. Dome 942 is also preferably porous either in whole or in part to allow air to circulate and pass in and out of tube 302. Protective cover 940 is a disposable component—like a dressing—and will typically be removed and exchanged for a replacement every day or few days as required.

Figure 9F:
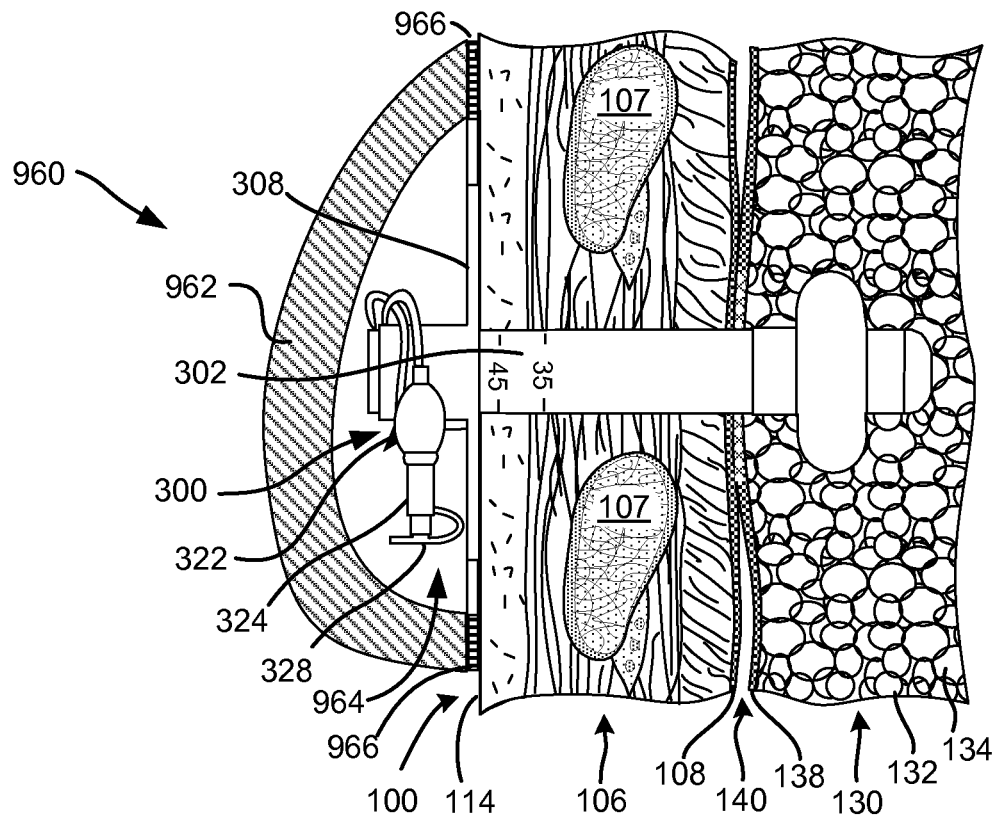
Figure 9G:
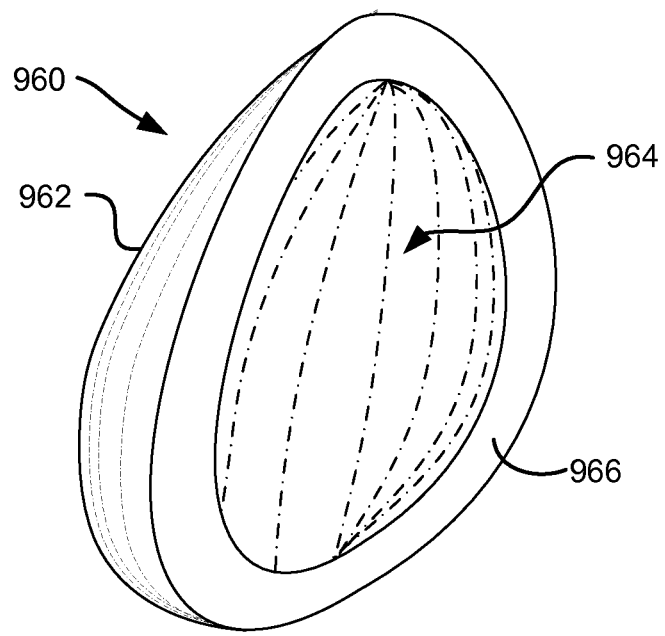

FIGS. 9F and 9G shows sectional and perspective views respectively of an alternative post-operative protective cover 960. Protective cover 960 is similar in shape and function to protective cover 940, however, protective cover 960 attaches directly to the skin of the patient rather than to the flange of the pneumostomy catheter 300. Protective cover 960 includes dome 962 which is specially-shaped to protect the exterior components of the pneumostomy catheter 300 during the post-operative period in which a pneumostoma is healing. As shown in FIGS. 9F and 9G, dome 962 is pear-shaped and defines a cavity 964 sized to accommodate the tube 302, pilot balloon 322, check valve 324, flange 308 and cap 328 of pneumostomy catheter 300. The flat edge of dome 962 is coated with an adhesive 966, such as a hydrocolloid adhesive, to attach cover 960 to the chest 100 of the patient. The contact between the adhesive 966 and the skin 114 on the chest 100 of the patient effectively seals the space surrounding pneumostomy catheter 300. Dome 962 should be relatively low-profile and smooth so as not to restrict movement of the patient or interfere with the patient's clothing during the postoperative period.

Dome 962 is preferably made of a stiff hydrophobic material such that when protective cover 960 is in position over pneumostomy catheter 300, protective cover 960 prevents entry of water or other foreign matter into tube 302. Dome 962 is also designed to capture any discharge form tube 302. Dome 962 is also preferably porous either in whole or in part to allow air to circulate and pass in and out of tube 302. Protective cover 960 is a disposable component—like a dressing—and will typically be removed and exchanged for a replacement every day or every few days as required.

Figure 10D:
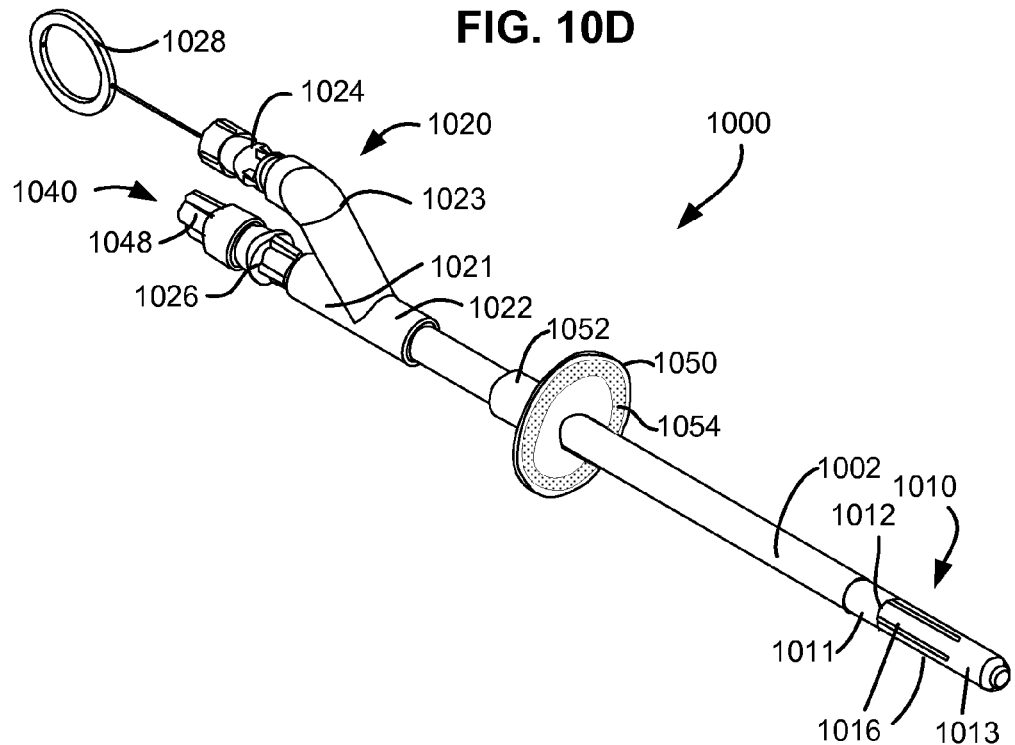
Figure 10E:
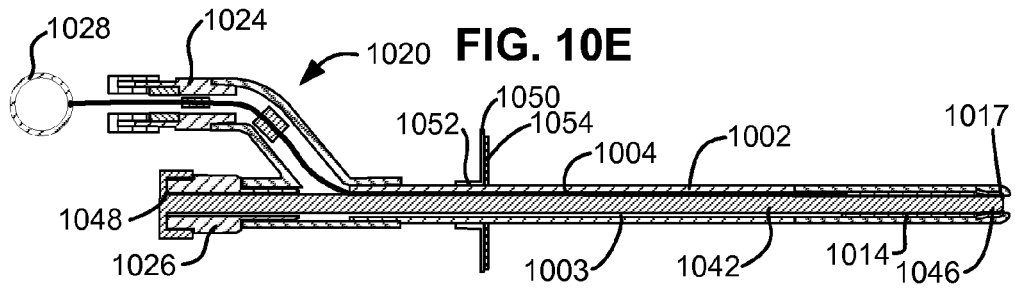
Figure 10F:
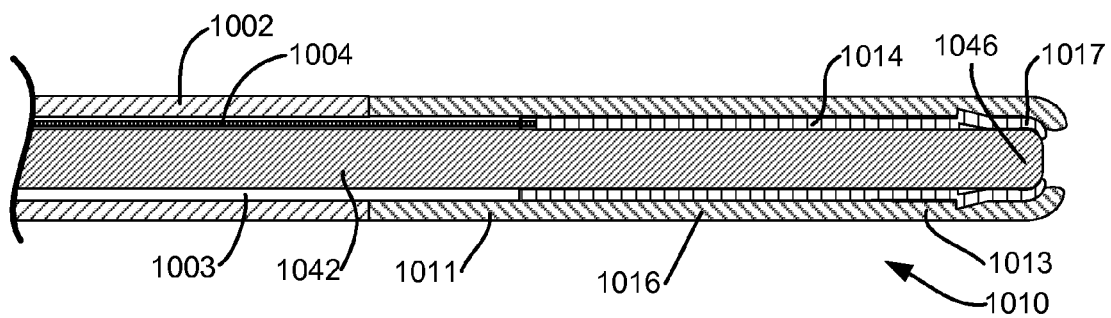

FIGS. 10A-10F show views of an alternate pneumostomy instrument 1000. FIGS. 10A-10C show pneumostomy instrument 1000 in its expanded position in which the pneumostomy instrument is configured to secure the lung of a patient. FIGS. 10D-10F show pneumostomy instrument 1000 in its expanded position in which the pneumostomy instrument is configured during insertion to and removal from the lung.

FIG. 10A shows a perspective view of pneumostomy instrument 1000. FIG. 10B shows a sectional view of pneumostomy instrument 1000 and FIG. 10C shows an enlarged sectional view of the distal end of pneumostomy instrument 1000. As shown in FIG. 10A, pneumostomy instrument 1000 comprises a tube 1002 having at the distal end an expanding basket 1010 and having a proximal structure 1020.

The tube 1002 is between five and ten inches in length and is preferably between six and seven inches in length. The tube may be from one quarter to three quarters of an inch in diameter and is preferably ⅜ of an inch in diameter. The tube has a lumen 1003. In a preferred embodiment, the tube is made from e.g. c-flex 50A). However, other biocompatible thermoplastic elastomers may be used. The relatively soft material of the tube 1002 allows the tube 1002 to fold over outside the body in order that it may be secured during the immediate postoperative period. Reinforcing features may be added to tube 1002 to increase its column strength and tensile strength. However, it is preferred that the reinforcement does not prevent the tube 1002 from bending. For example, longitudinal inelastic reinforcing fibers may be embedded in tube 1002 or otherwise affixed to the tube 1002 in order to increase the tensile strength while still permitting bending. In another example, tube 1002 may be spiral wound with wire (or be embedded with said wire) to increase its column strength while still permitting bending.

The material of the expanding basket 1010 is selected such that it can maintain the desired expanded profile when positioned within the lung but can be safely returned to a low profile for extraction. The harder durometer material of the basket allows it to maintain its expanded shape in the lung. In a preferred embodiment, the expanding basket 1010 is made from a harder durometer material, for example c-flex (e.g. c-flex 90A) than the tube (e.g. c-flex 50A). However, other thermoplastic elastomers may be used.

The expanding basket 1010 may also be covered with a thin elastic covering that allows for expansion and collapsing of the basket, for example, an elastic balloon material. See, for example, polymer skin 924 covering the flexible expanding cage in FIG. 9C. The covering would assist the expanding basket 1010 in pushing aside parenchymal tissue of the lung during expansion of the basket. The covering would, thus, assist anchoring of the expanding basket 1010 within the lung while facilitating later removal of expanding basket 1010 after the pneumostoma has formed. The thin covering may also extend along the length of tube 1002 to maintain a uniform outside diameter and to help with stabilization of the tube 1002. As shown in FIG. 10A, pneumostomy instrument 1000 is provided with a mandrel 1040. Mandrel 1040 includes an elongated member 1042 adapted to fit through tube 1002 into expanding basket 1010. The distal tip 1046 of mandrel 1042 is adapted to engage expanding basket 1010 and stretch it into a linear configuration suitable for insertion and removal of the instrument. The mandrel also imparts extra stiffness to pneumostomy instrument 1000 during insertion and removal. Mandrel 1040 has a luer fitting 1048 attached to the proximal end. Luer fitting 1048 engages the female luer fitting 1026 to secure mandrel 1040 within pneumostomy instrument 1000 during insertion and removal. Mandrel 1040 may be provided with a radio marker, radiopaque or echogenic material incorporated in the distal tip 1046 so that the tip may be visualized during insertion of the pneumostomy instrument.

As shown in FIG. 10A, pneumostomy instrument 1000 may also be provided with an access flange 1050. Access flange 1050 is designed such that it may be secured against the skin of the chest of the patient and collar 1052 may be secured to tube 1002 thereby fixing tube 1002 in position relative to the chest of the patient. Access flange 1052, is slidable along the length of the tube 1002. The flange 1052 is designed to be positioned against the skin. The flange 1050 can be sutured to tube 1002 to secure the flange in position along the catheter or fixed in place by other means such as tape, adhesive, clips and staples and the like or by having a built-in securing mechanism, such as a cam, ratchet, lock or the like. The flange 1052 is designed to maintain a tension between the expanding basket 1010 embedded in the lung and the thoracic wall. Once access flange 1050 is secured to tube 1002, access flange 1050 provides the necessary counterforce for the expanding basket 1010. Access flange 1050 may also be provided with an adhesive coating 1054 to temporarily secure the flange 1050 to the skin of the patient and thereby preclude accidental dislodgment of the catheter.

FIG. 10C shows a sectional view of expanding basket 1010. Expanding basket 1010 comprises an outer section 1012 and an inner section 1014. Outer section 1012 has a proximal tube 1011 and a distal tube 1013 connected by a plurality of expanding elements 1016. Proximal tube 1011 is bonded to tube 1002. Distal tube 1013 ends in distal aperture 1018. Optional, side apertures may also be provided in distal tube 1013 and or proximal tube 1011. Expanding elements 1016 are shaped such that they extend radially from the long axis of expanding basket 1010. Expanding elements are formed in the expanded configuration. Outer section 1012 is butt joined to the distal end of tube 1002. Expanding basket 1010 may be provided with a radio marker, radiopaque or echogenic material incorporated in the distal tip 1046 so that the tip may be visualized during insertion of the pneumostomy instrument. Expanding basket 1010 is designed to push aside the parenchymal tissues of the lung when expanded thereby creating a cavity within the parenchymal tissue. Expanding basket 1010 is also designed to anchor pneumostomy catheter 1000 within the parenchymal tissue of the lung. Alternative expanding devices may be used so long as they achieve these same functions.

Inner section 1014 is generally tubular and fits within proximal tube 1011 and distal tube 1013 of outer section

1012. In a preferred embodiment inner section 1014 is a hollow metal tube having a reduced diameter tip 1017. Inner section 1014 is bonded to distal tube 1013. Inner section 1014 also has a plurality of barbs 1015 for securing inner section 1014 to distal tube 1013. Inner section 1014 is slidingly received within proximal tube 1011.

A length of suture 1004 is fixed to the proximal end of inner section 1014. Suture 1004 may be used to secure inner section 1014 in the position shown in FIG. 10C. Suture 1004 runs through the lumen 1003 of tube 1004 and out through proximal structure 1020. As shown in FIG. 10B, two stops 1006 and 1007 are crimped and/or UV-bonded to suture 1004. The distal stop 1007 is responsible for limiting the pull or throw of the suture, preventing the physician from over expanding the basket. The proximal stop 1006 is used to assure the basket stays expanded while in place in the body. The proximal end of suture 1004 is securely fixed to a pull-ring 1028 which helps the physician or user grasp and pull the suture.

FIG. 10B shows a sectional view of proximal structure 1020. In the distal end of inner section 1014 and section 1012 (as shown in FIG. 10C) suture 1004 runs through the lumen 1003. Proximal structure 1020 includes a plastically Y-connector 1022. The distal end of Y-connector 1022 is bonded to the proximal end of tube 1002 with a UV-cured adhesive. The straight arm 1021 of the Y-connector 1022 is attached to a high flow female luer fitting 1026 with a UV-cured adhesive. The side arm 1023 of the Y-connector is attached to a Tuohy Borst connector (Tuohy) 1024. The components may be secured to each other using adhesive, welding, melting or other techniques appropriate to the materials to be secured. Suture 1004 passes through the Tuohy 1024. Stop 1006 is sized such that when Tuohy 1024 is open it may pass through grommet 1025. However, when Tuohy 1024 is closed (as shown in FIG. 10B) stop 1006 may not pass through grommet 1025. Stop 1007 is too large to pass into Tuohy 1024.

FIGS. 10D-10F show views of pneumostomy instrument 1000 configured for introduction or removal from the lung of a patient. In this configuration mandrel 1040 has been inserted into pneumostomy instrument 1000. As shown in FIG. 10D the luer fitting 1048 of mandrel 1040 has been secured to female luer 1026 of pneumostomy instrument 1000. The insertion of mandrel 1040 has caused expanding head 1010 to assume a reduced diameter configuration in which expanding elements 1016 are substantially flush with the surface of proximal tube 1011 and distal tube 1013.

As shown in FIGS. 10E and 10F, mandrel 1040 passes through female luer 1026, through lumen 1003 of tube 1002 and into inner section 1014 of expanding basket 1010. Tip 1046 of mandrel 1040 engages tip 1017 of inner section 1014. Mandrel 1040 is of sufficient length that insertion of mandrel 1040 into pneumostomy instrument 1000 pushes distal tube 1013 of expanding basket 1010 away from proximal tube 1012 thereby causing expanding elements 1016 to be stretched out and assume the configuration shown in FIGS. 10D-10F.

The pneumostomy instrument 1000 may be utilized in any of the pneumostomy procedures described herein including those procedures described in FIGS. 4A-4F, 5A-5C, 6A-6C, 7A-7C and accompanying text. For certain applications, it is desirable to assemble pneumostomy instrument 1000 with a percutaneous insertion tool so that the pneumostoma catheter can penetrate through the chest wall and pleural membranes and the parenchymal tissue without need for previous incision or dissection. The percutaneous insertion tool is a device that permits the rapid deployment of the pneumostomy catheter through chest wall and the parietal and visceral membranes into the lung. The insertion tool preferably prevents deflation of the lung by rapid deployment of the pneumostomy catheter and subsequent expansion of expanding basket 1010. The percutaneous insertion tool may comprise a trocar designed to fit through lumen 1003 of the pneumostomy instrument in place of mandrel 1040 and dissect tissue in a minimally traumatic way thereby allowing the pneumostomy catheter to penetrate the pleural membranes and enter the parenchymal tissue of the lung.

FIGS. 11A-11C show a pneumostomy instrument 1000 assembled with a percutaneous insertion tool 1100. FIG. 11A shows a perspective view of the pneumostomy instrument 1000 assembled with the percutaneous insertion tool 1100. FIGS. 11B and 11C show detailed sectional views of the distal end of the pneumostomy instrument 1000 and insertion tool 1100. Referring first to FIG. 11A, percutaneous insertion tool 1100 is sized to fit through the main lumen of pneumostomy instrument 1000. A dissecting tip 1102 of percutaneous insertion tool 1100 protrudes beyond the distal tip of pneumostomy instrument 1000. Dissecting tip 1102 is preferably a dissecting tip that pushes tissue aside rather than cutting through tissue. A handle 1104 extends from the proximal end of pneumostomy instrument 1000 allowing the physician to control the instrument. A coupling 1106 temporarily secures the percutaneous insertion tool 1100 to the female luer 1026 (shown in FIG. 11A) at the proximal end of pneumostomy instrument 1000.

FIG. 11B shows a sectional view of the distal tip of pneumostomy instrument 1000 and insertion tool 1100. As seen in FIG. 11B, percutaneous insertion tool 1100 includes a sleeve 1101 in which distal tip 1102 is received. The distal end of sleeve 1101 engages the distal end 1017 of inner section 1014 of expanding basket 1010. The dissecting tip extends through the aperture 1018 in the end of pneumostomy instrument 1000. An actuator 1106 comprises a spring-loaded mechanism for withdrawing dissecting tip 1101 back towards the proximal end of pneumostomy instrument. The actuator latches the dissecting tip in the forward position until triggered. The actuator is triggered by the insertion of dissecting tip 1102 through the chest wall and then into the softer tissue of the lung. The refraction of the dissecting tip after passage of the instrument into the parenchymal tissue of the lung helps prevent injury to the lung caused by over insertion. The retraction of the dissecting tip may also be used, in some embodiments, to trigger deployment of expanding basket 1010, by, for example, releasing coupling 1106 and allowing the pneumostomy instrument 1000 to relax and allowing the expanding basket 1010 to take on its expanded configuration.

FIG. 11C illustrates the configuration of the percutaneous insertion tool 1100 and pneumostomy instrument 1000 after deployment into lung tissue. As shown in FIG. 11C, tip 1102 has been retracted into opening 1018 in the distal end of pneumostomy instrument 1000. Expanding elements 1016 have moved out radially from the axis of pneumostomy instrument 1000. The expanding elements push aside the parenchymal tissue to make a cavity and secure the end of pneumostomy instrument 1000 into the lung. Percutaneous insertion tool 1100 may now be removed, leaving pneumostomy instrument 1000 in place. After stabilization of the pneumostoma in 7 to 14 days, a mandrel (such as mandrel 1040 of FIG. 10A) is inserted into the lumen of the pneumostomy instrument 1000 again causing expanding elements 1016 to return to their low profile configuration. When mandrel 1040 is secured to pneumostomy instrument 1000 (see e.g. FIG. 10E) the instrument may be removed from the chest of the patient. A pneumostoma management device should then be placed in the pneumostoma (see FIGS. 8A-8B and accompanying text).

Postoperative Pneumostomy Instrument Support

As described above, the instrument used to create the pneumostoma remains in place in the patient for a period of time in order for the tissues displaced by the instrument to heal and to allow pleurodesis between the visceral and pleural membranes surrounding the instrument. During this immediate postoperative period it is desirable to maintain the comfort and/or mobility of the patient. Thus, it is desirable that the instrument used to perform the pneumostomy procedure be secured in a low-profile configuration that reduces inconvenience to the patient. It is also desirable that the instrument be aligned approximately perpendicular to the chest wall where it passes through the chest wall, so that pneumostoma forms in approximately this configuration. It is also desirable that the instrument be maintained under a slight tension to aid pleurodesis. In order to achieve and maintain the appropriate configuration of the pneumostomy instrument during the post-operative period while reducing inconvenience and discomfort to the patient, a postoperative pneumostomy instrument support is provided. The post-operative pneumostomy instrument support keeps the pneumostomy instrument aligned with the stoma, applies a slight tension to the pneumostomy instrument, prevents kinking of the instrument; and secures the instrument in a low-profile configuration for the post-operative period.

Figure 12A:
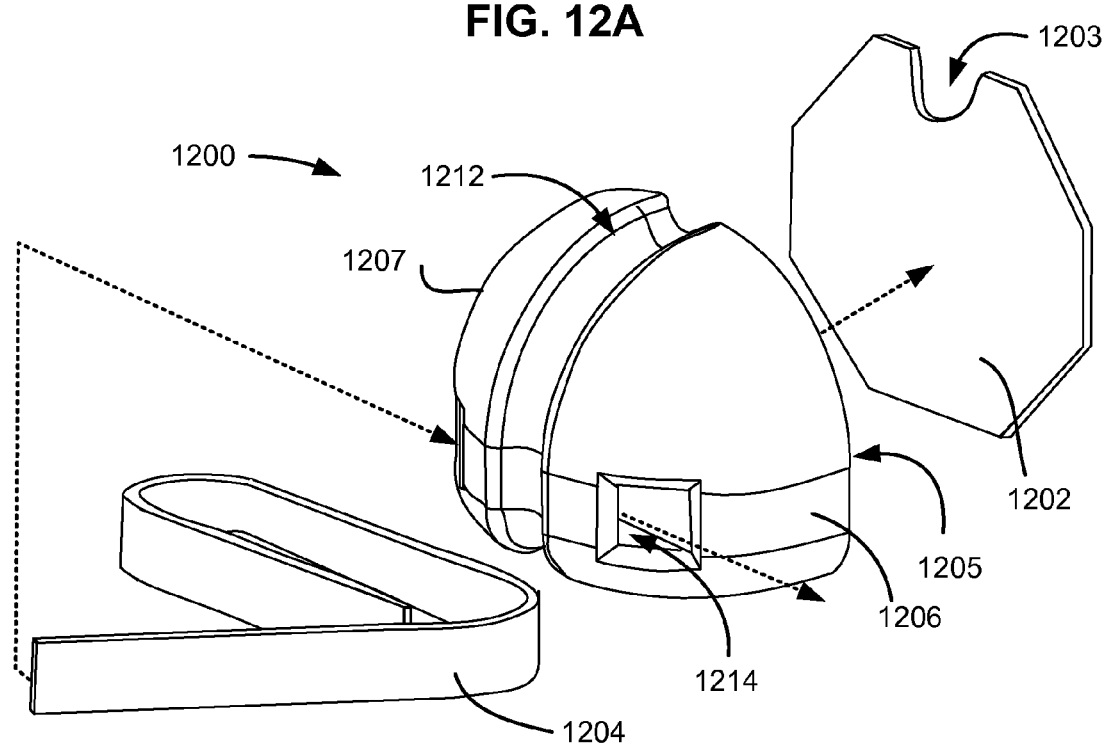
Figure 12B:
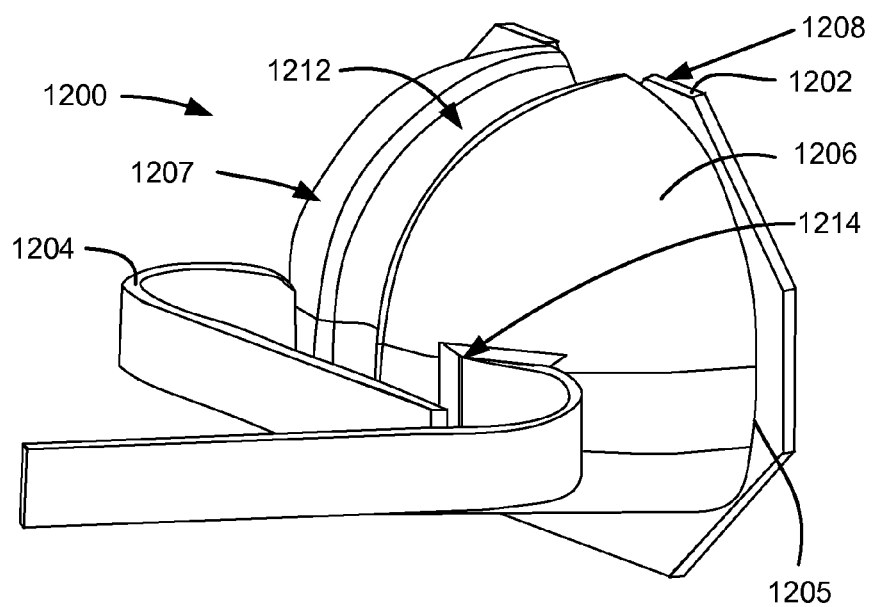

FIGS. 12A and 12B show a postoperative pneumostomy instrument support 1200. FIG. 12A shows an exploded view of the components of support 1200. Support 1200 has three main components: adhesive backing 1202, strap 1204 and block 1206.

Adhesive backing 1202 is a compliant foam pad coated on each side with a thin layer of biocompatible adhesive. The compliant foam allows the pad to conform somewhat to the chest of the patient. The adhesive backing has a U-shaped opening 1203 in one edge to allow it to fit around the pneumostomy instrument at the insertion site. The opening 1203 is large enough that the adhesive backing 1202 does not interfere with the incision.

Block 1206 is formed from light weight rigid and/or semi-rigid foam. The block has a flat surface 1205 for attachment to the adhesive backing 1202. The block has a curved front surface 1207 for supporting the pneumostomy instrument. The front surface 1207 has a semicircular channel 1212 designed to receive the tube of the pneumostomy instrument. The channel 1212 is aligned perpendicular to the patient-side 1208 (shown in FIG. 12B) where the front surface 1207 meets the flat surface 1205. The front surface 1207 of block 1206 and channel 1212 subsequently curve away from perpendicular until approximately parallel with the flat surface 1205. The radius of curvature and shape of the channel is selected so as not to cause the tube of the pneumostomy instrument to kink. An aperture 1214 passes through block 1206 from one side of channel 1212 to the other.

Strap 1204 is designed to hold the pneumostomy instrument to block 1206 and maintain a slight tension in the instrument. Strap 1204 is sized to fit through aperture 1214 of block 1206. Strap 1204 may be provided with a releasable adhesive for securing the strap to itself and the pneumostomy instrument. Strap 1204 may additionally, or alternatively, be provided with a fastener for securing the pneumostomy instrument. Strap 1204 is preferably made of a somewhat elastic material to aid in fixing the instrument to block 1206 and applying tension to the pneumostomy instrument without crushing the pneumostomy instrument.

FIG. 12B shows the assembled support 1200. Strap 1204 is positioned through aperture 1214 such that the free ends of strap 1204 are available to secure a pneumostomy instrument into channel 1212. Adhesive backing 1202 is secured to the flat surface 1205 of block 1206 by a layer of adhesive. Typically, the remaining adhesive layer is protected with a removable layer of paper until ready for use. The U-shaped opening 1203 is aligned with channel 1212. Note that adhesive backing 1202 is preferably larger in area than the flat surface 1205 of block 1206 to facilitate removal of support 1200 by peeling up of adhesive backing 1202.

FIG. 12C shows a sectional view through support 1200 to illustrate the use of support 1200 in conjunction with a pneumostomy instrument 1000 positioned within a pneumostoma 110. Block 1206 is secured to the skin 114 of chest 100 adjacent pneumostoma 110 by adhesive backing 1202. As shown in FIG. 12C, tube 1002 is aligned perpendicular to the wall of chest 100 where tube 1002 exits chest 100. Tube 1002 follows the curvature of block 1206 until approximately parallel with chest 100. The shape of channel 1212 (shown in FIGS. 12A and 12B) and the radius of curvature of block 1206 prevent tube 1002 from kinking Tube 1002 is releasably secured to block 1206 and under tension by strap 1204. Using support 1200 in this manner allows the pneumostomy instrument 1000 to be secured to the chest of the patient in a low profile configuration during the post operative period while maintaining the alignment of the pneumostoma 110.

FIG. 12C also illustrates the use of a discharge trap 1220 with pneumostomy instrument 1000. During the immediate postoperative period, there may be drainage of blood and other fluids through pneumostomy instrument 1000 in addition to gases from the lung. It is desirable to contain such discharge using a passive of vacuum discharge trap. Discharge trap 1220 has a fitting 1224 to mate with the female luer fitting of pneumostomy instrument 1000. Gases and/or discharge flow though the fitting 1224 into a vessel 1222 via a valve 1226. Valve 1226 is a one-way valve which prevents discharge from reentering the pneumostomy instrument from vessel 1222. Discharge 1230 may collect in vessel 1222 which may be emptied or changed when necessary. Gases may escape from vessel 1222 through outlet 1228. Outlet 1228 preferably includes a hydrophobic filter element to prevent the exit of discharge from vessel 1222. Outlet 1228 may vent to atmosphere or may alternatively be connected to a regulated vacuum source (such as a medical vacuum line).

Figure 12D:
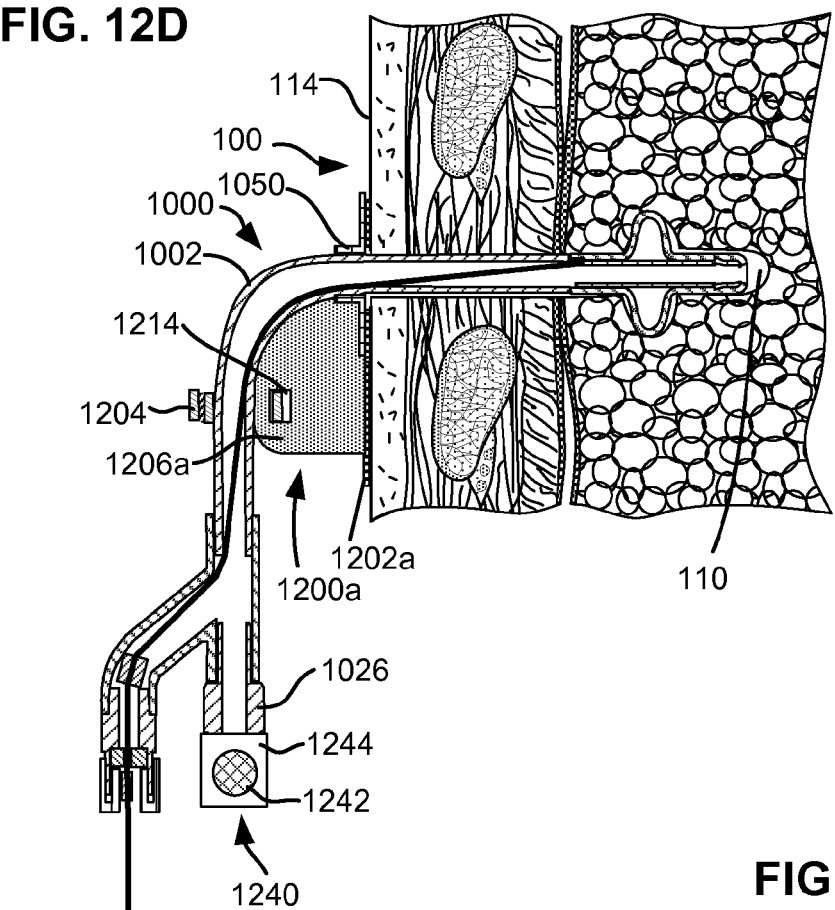

Support 1200 may be used instead of, or in addition to, flange 1050 of pneumostomy instrument 1000 (not shown but see FIG. 10A). FIG. 12D shows a sectional view through a support 1200a to illustrate the use of a support 1200a in conjunction with a pneumostomy instrument 1000 having a flange 1050 (see FIG. 10A). Support 1200a is similar to support 1200 but has adaptations to make it compatible with flange 1050. Block 1206a is secured to the skin 114 of chest 100 adjacent flange 1050 by adhesive backing 1202a. Block 1206a and adhesive backing 1202a are adapted to provide sufficient space for flange 1050. Block 1206a may also be provided with a clip, strap or other fastener to secure support 1200a to flange 1050. As shown in FIG. 12D, tube 1002 is aligned perpendicular to the wall of chest 100 where tube 1002 exits chest 100. Flange 1050 works in conjunction with block 1206a to align tube 1002 and apply tension to tube 1002. Using support 1200a in this manner again allows the pneumostomy instrument 1000 to be secured to the chest of the patient in a low profile configuration during the post operative period while maintaining the alignment of the pneumostoma 110.

FIG. 12D also illustrates the use of a cap 1240 with pneumostomy instrument 1000. During the immediate postoperative period there may be drainage of blood and other fluids through pneumostomy instrument 1000 in addition to gases from the lung. After a few days however, there may be little further drainage. Thus, it may be possible to remove the discharge trap or vacuum source attached to instrument 1050. In order to prevent contaminants entering the lung through pneumostomy instrument 1000, a cap 1240 may be used to close the lumen of the instrument. Cap 1240 has a fitting 1244 to mate with the female luer fitting of pneumostomy instrument 1000. Cap 1240 may optionally be provided with a vent 1242 to allow gases to escape. Cap 1240 may be used to enhance patient mobility with occasional use of a discharge trap or vacuum aspiration to clear any discharge from instrument 1000.

Figure 12E:
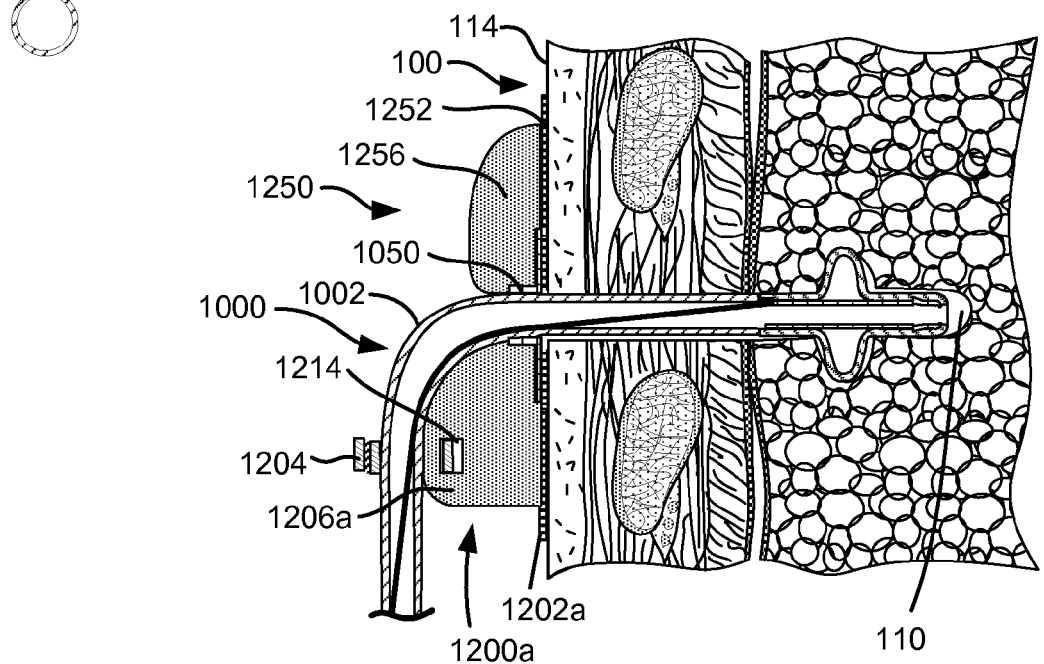

Supports 1200, 1200a may be used in conjunction with a second support 1250. FIG. 12E shows a sectional view through a support 1200a to illustrate the use of a support 1200a in conjunction with a pneumostomy instrument 1000 having a flange 1050 (see FIG. 10A) and a second support 1250. Second support 1250 comprises a block 1256 secured to the skin 114 of chest 100 adjacent flange 1050 by adhesive backing 1252. Block 1256 and adhesive backing 1252 are adapted to provide sufficient space for flange 1050. Block 1256 may also be provided with a clip, strap or other fastener (not shown) to secure second support 1250 to flange 1050. As shown in FIG. 12E, tube 1002 is aligned perpendicular to the wall of chest 100 where tube 1002 exits chest 100. Second support 1250 works in conjunction with support 1200a and flange 1050 to align tube 1002 and apply tension to tube 1002. Second support 1250 helps constrain tube 1002 perpendicular to the wall of chest 100 while relieving strain in tube 1002 that might otherwise misalign the pneumostoma 110. Second support 1250 may in some cases be attached to support 1200a or even formed in one piece with support 1200a. In some embodiments, the distance between support 1250 and support 1200a may be adjusted in order to adjust the radius of curvature of the tube 1002.

Pneumostomy Techniques Using the Alternate Pneumostomy Instrument

Figure 13B:
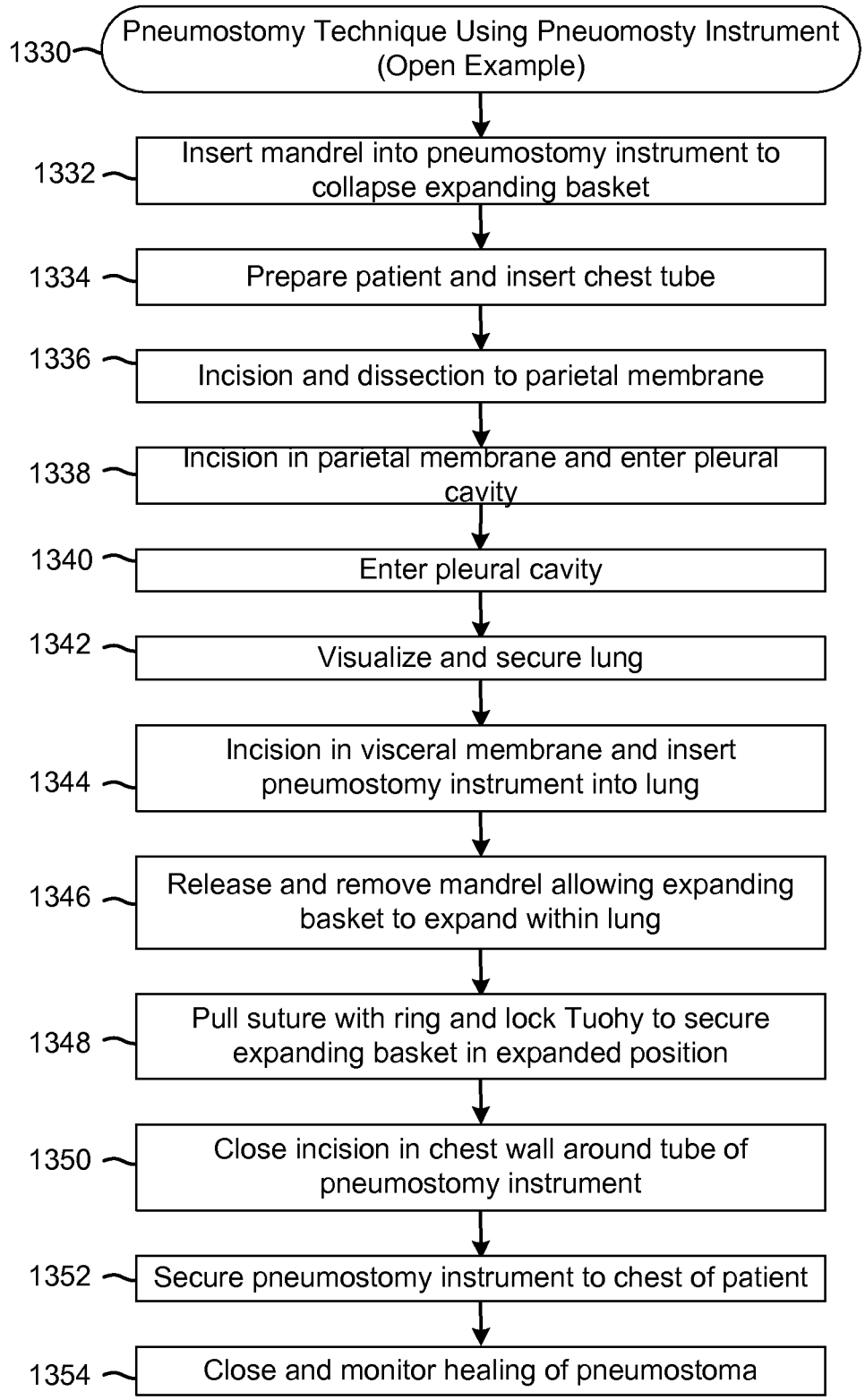

The pneumostomy instrument 1000 may be utilized in any of the pneumostomy procedures described herein including those procedures described in FIGS. 4A-4F, 5A-5C, 6A-6C, 7A-7C and accompanying text. FIGS. 13A and 13B are flowcharts showing the steps of a single-phase pneumostomy technique utilizing pneumostomy instrument 1000. In these single-phase techniques no prior pleurodesis is required ahead of the procedure. In the percutaneous single-phase procedure (FIG. 13A), the pneumostomy instrument 1000 is introduced without collapsing the lung. In the open single-phase procedure (FIG. 13B), the lung may be allowed to inflate prior to insertion of pneumostomy instrument 1000 and then reinflated after pneumostomy instrument 1000 is secured within the lung.

Percutaneous Technique

Referring first FIG. 13A which shows the steps of the percutaneous single-phase technique 1300 utilizing pneumostomy instrument 1000. Pneumostomy instrument 1000 is first assembled with percutaneous insertion tool 1100 as shown in FIG. 11A (step 1302). In this configuration the expanding head is secured in a low-profile configuration ready for insertion into the lung. The patient is prepared (step 1304) using local anesthesia at the target site in addition to a sedative or general anesthesia. A chest tube is preferably inserted into the pleural cavity as a prophylactic measure. The physician optionally makes an incision at the target location and dissects to the parietal membrane (step 1306). The physician optionally introduces a pleurodesis agent to the outer surface of the parietal membrane or, by injection, through the parietal membrane into the pleural space at the target location (step 1308) to promote pleurodesis between the visceral and parietal membranes after the procedure. One or more of the pleurodesis agents discussed above may be used in order to promote pleurodesis formation following the procedure, however, it is not expected that the pleurodesis will form during the procedure itself. At step 1310, the physician inserts the pneumostomy instrument and percutaneous insertion tool through the parietal and visceral membranes using the percutaneous insertion tool. Insertion is made by way of the incision if made, or otherwise directly through the chest wall if no prior incision was made. The pneumostomy instrument is inserted until the expanding head is through the visceral membrane and embedded within the parenchymal tissue of the lung. Because there has been no pleurodesis between the parietal membrane and visceral membrane, a small amount of air may leak into the pleural cavity around the tube of the pneumostomy instrument. However, the chest tube should be able to extract the small amount of air and the lung will remain inflated and pushed against the chest wall.

Referring again to FIG. 13A, at step 1312 the physician releases the expanding head and allows it to expand within the parenchymal tissue of the lung. Note that in some embodiments an actuator automatically deploys the expanding head after it is positioned with the lung. At step 1314, the suture and stop may be pulled through the open Tuohy and the Tuohy closed to secure the expanding head in the expanded configuration. The percutaneous insertion tool is removed from the main lumen of the pneumostomy instrument (this step may alternatively be performed before balloon inflation). At step 1316, the flange or instrument support is secured to the skin of the chest of the patient adjacent the instrument. At step 1318, a slight tension is applied to the tube of the pneumostomy instrument, drawing the expanding head and lung towards the thoracic wall. The tension brings the parietal membrane and visceral membrane into contact. The contact between the parietal membrane and visceral membrane reduces or eliminates any remaining air leak around the instrument. Moreover, the contact between the parietal membrane and visceral membrane allows pleurodesis to occur resulting in adhesion between the pleural membranes and sealing of the pneumostoma from the pleural cavity. Some or the entirety of the pneumostomy instrument may be coated and/or impregnated with a pleurodesis agent to promote the formation of the pleurodesis. After the tension is applied, the pneumostomy instrument is secured to the flange or instrument support (step 1320).

The remainder of the instrument is then secured to the chest/abdomen of the patient (step 1322). In some procedures it may be desirable to apply a water seal or slight vacuum to the instrument during the immediate postoperative period to collect blood and discharge and reduce the opportunity for any infectious agents to enter the lung. If an incision was made, it is now closed using sutures, staples and/or tissue glue (step 1324). The patient is then monitored to ensure that pneumothorax has not occurred. A chest tube is inserted or maintained as necessary until it is clear that there is no leakage of air into the pleural cavity. Air flow through the pneumostomy instrument is also monitored. Healing of the pneumostoma is monitored and the pneumostomy instrument is removed when the physician believes the pneumostoma is sufficiently stable to tolerate the removal of the instrument (see FIG. 13C).

Open Technique

Referring next to FIG. 13B which shows the steps of the open single-phase technique 1330 utilizing pneumostomy instrument 1000. Pneumostomy instrument 1000 is first assembled with mandrel 1040 as shown in FIG. 10A (step 1332). In this configuration the expanding head is secured in a low-profile configuration ready for insertion into the lung. The patient is prepared (step 1334) using local anesthesia at the target site in addition to a sedative or general anesthesia. If a general anesthesia is applied, the patient will also be intubated and ventilated. A chest tube is inserted into the pleural cavity. The physician makes an incision at the target location and dissects to the parietal membrane (step 1336). At step 1338, the surgeon makes an incision through the parietal membrane and enters the pleural cavity (step 1340). At step 1342, the physician visualizes the lung, and engages it with a surgical tool, and secures the lung to the chest wall adjacent the incision. The surgeon may use sutures, staples, clips, surgical adhesive and/or a surgical adhesive patch to secure the visceral membrane of the lung to the chest wall in step 1342. The physician optionally introduces a pleurodesis agent to the outer surface of the parietal membrane or, by injection, through the parietal membrane into the pleural space at the target location (step 1338) to promote pleurodesis between the visceral and parietal membranes after the procedure. One or more of the pleurodesis agents discussed above may be used in order to promote pleurodesis formation following the procedure, however, it is not expected that the pleurodesis will form during the procedure itself.

At step 1344, the physician makes an incision through the visceral membrane and inserts the pneumostomy instrument and mandrel through the incision into the parenchymal tissue of the lung. The pneumostomy instrument is inserted until the expanding head is through the visceral membrane and embedded within the parenchymal tissue of the lung. Counter pressure may need to be applied to secure the lung as the pneumostomy instrument is inserted.

Referring again to FIG. 13B, at step 1346 the physician releases the expanding head and allows it to expand within the parenchymal tissue of the lung. At step 1348, the suture and stop may be pulled through the open Tuohy and the Tuohy closed to secure the expanding head in the expanded configuration. The mandrel may also be removed from the main lumen of the pneumostomy instrument. At step 1350, the incision in the chest wall is closed around the tube of the pneumostomy instrument. At step 1352 the pneumostomy instrument is then tensioned and secured as described in steps 1316-1322 of FIG. 13A.

With the incision closed and slight tension applied to the pneumostomy instrument, the removal of air through the chest tube will be sufficient to reinflate the lung. The patient is then monitored to ensure that the lung inflates. A chest tube is inserted or maintained as necessary until it is clear that there is no leakage of air into the pleural cavity. Air flow though the pneumostomy instrument is also monitored. Healing of the pneumostoma is monitored (step 1354) and the pneumostomy instrument is removed when the physician believes the pneumostoma is sufficiently stable to tolerate the removal of the instrument (see FIG. 13C).

Removal of Pneumostomy Instrument

When the physician considers that the pneumostoma has healed adequately, the pneumostomy instrument is removed and the pneumostoma is inspected. The physician will then verify the size of the pneumostoma and provide a pneumostoma management device (PMD) of the appropriate size. Removal of the pneumostomy instrument requires that the expanding basket be collapsed to the low profile configuration.

Figure 13C:
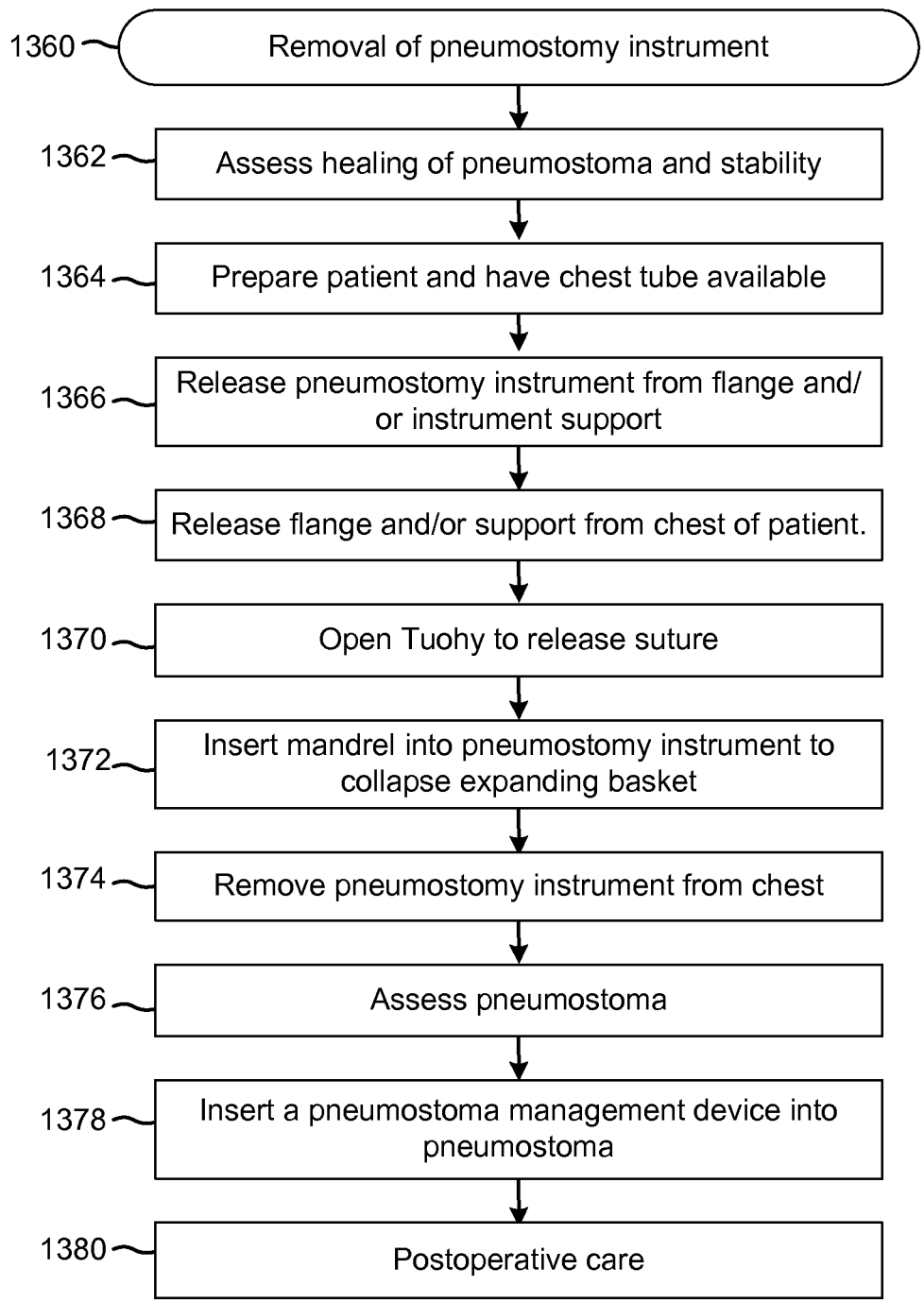

Referring next to FIG. 13C which shows the steps (1360) for removal of the pneumostomy instrument 1000. The surgeon should first assess the healing and stability of the pneumostoma (step 1362). The pneumostomy instrument should not be removed until the pneumostoma is sufficiently healed to tolerate the removal procedure. The patient is prepared (step 1364). A local anesthesia may be applied and a sedative provided. A chest tube should be available in case removal of the pneumostomy instrument causes leakage of air into the pleural cavity. The pneumostomy instrument is first released from the flange and/or instrument support (step 1366). The flange and/or support are then released from the chest of the patient (step 1368) providing access to inspect and clean the stoma. The Tuohy is opened to release the stop which secured the expanding basket in the expanded position (step 1370). A mandrel is then inserted into the pneumostomy instrument causing the expanding basket (within the lung) to collapse to a low profile configuration (step 1372). The pneumostomy instrument is then withdrawn from the pneumostoma (step 1374). The pneumostoma should be quickly assessed (step 1376). A pneumostoma management device should then be inserted into the pneumostoma to preserve patency during the continued healing period (step 1378). The patient should be observed to ensure that the procedure has not caused leakage of air into the pleural cavity. If leakage occurs a chest tube should be inserted into the pleural cavity (at another site) until the air leakage is resolved. The patient will be provided with standard postoperative care transitioning to outpatient care and continued pulmonary rehabilitation (step 1380). The first pneumostoma management device will typically be left in place till the first outpatient visit to a physician. At the first outpatient visit, the first pneumostoma management device will be removed, the pneumostoma inspected again. The physician, or more typically the patient under the physician's direction, will then insert the next PMD. The PMD's will thereafter be exchanged by the patient or a caregiver on a regular basis and/or as needed.

Materials

In preferred embodiments, the pneumostomy instruments and PMD are formed from biocompatible polymers or biocompatible metals. In a particular embodiment pneumostomy catheter 300 and PMD 800 are made from PEBAX®, a polyether block amide manufactured by Arkema in France, polypropylene and ABS. The balloon of the pneumostomy catheter 300 is preferably made of polyurethane or the equivalent. In a preferred embodiment, pneumostomy instrument 1000 is made from C-FLEX® thermoplastic elastomer manufactured by Saint-Gobain Performance Plastics in Clearwater, Fla. A patient will typically have a pneumostomy catheter implanted for from one to two weeks depending upon the time required for the pneumostoma to heal and form, and, thus, the materials, particularly of pneumostomy catheter 300, should meet high standards for biocompatibility. In general, preferred materials for manufacturing a pneumostomy instrument or PMD are biocompatible thermoplastic elastomers that are readily utilized in injection molding and extrusion processing. As will be appreciated, other suitable similarly biocompatible thermoplastic or thermoplastic polymer materials can be used without departing from the scope of the invention. Biocompatible polymers for manufacturing PMD may be selected from the group consisting of polyethylenes (HDPE), polyvinyl chloride, polyacrylates (polyethyl acrylate and polymethyl acrylate, polymethyl methacrylate, polymethyl-coethyl acrylate, ethylene/ethyl acrylate), polycarbonate urethane (BIONATE®), polysiloxanes (silicones), polytetrafluoroethylene (PTFE, GORE-TEX®, ethylene/chlorotrifluoroethylene copolymer, aliphatic polyesters, ethylene/tetrafluoroethylene copolymer), polyketones (polyaryletheretherketone, polyetheretherketone, polyetherether-ketoneketone, polyether-ketoneetherketoneketone polyetherketone), polyether block amides (PE- BAX®, PEBA), polyamides (polyamideimide, PA-11, PA-12, PA-46, PA-66), polyetherimide, polyether sulfone, poly(iso)butylene, polyvinyl chloride, polyvinyl fluoride, polyvinyl alcohol, polyurethane, polybutylene terephthalate, polyphosphazenes, nylon, polypropylene, polybutester, nylon and polyester, polymer foams (from carbonates, styrene, for example) as well as the copolymers and blends of the classes listed and/or the class of thermoplastics and elastomers in general. Reference to appropriate polymers that can be used for manufacturing a pneumostomy instrument or PMD can be found in the following documents: PCT Publication WO 02/02158, entitled "Bio-Compatible Polymeric Materials;" PCT Publication WO 02/00275, entitled "Bio-Compatible Polymeric Materials;" and, PCT Publication WO 02/00270, entitled "Bio-Compatible Polymeric Materials" all of which are incorporated herein by reference. Other suitable materials for the manufacture of the pneumostomy instrument or PMD include medical grade inorganic materials such stainless steel, titanium, ceramics and coated materials.

Additionally, components of the PMD and/or pneumostomy instrument that are in contact with the pneumostoma before or after healing may be designed to deliver a pharmaceutically-active substance. For purposes of the present disclosure, an "active pharmaceutical substance" is an active ingredient of vegetable, animal or synthetic origin which is used in a suitable dosage as a therapeutic agent for influencing conditions or functions of the body, as a replacement for active ingredients naturally produced by the human or animal body and to eliminate or neutralize disease pathogens or exogenous substances. The release of the substance in the pneumostoma has an effect on the course of healing and/or counteracts pathological changes in the tissue due to the presence of the temporarily implanted medical devices. In particular, it is desirable in some embodiments to coat or impregnate the PMD with pharmaceutically-active substances that preserve the patency of the pneumostoma and/or are antimicrobial in nature but that do not unduly irritate the tissues of the pneumostoma. In particular, it is also desirable in some embodiments to coat or impregnate the pneumostoma instrument with pharmaceutically-active substances that aid pleurodesis, healing and/or epithelialization of the pneumostoma and/or are antimicrobial in nature but that do not unduly irritate the tissues of the pneumostoma.

In particular cases, suitable pharmaceutically-active substances may have an anti-inflammatory and/or antiproliferative and/or spasmolytic and/or endothelium-forming effect, so that the functionality of the pneumostoma is maintained. Suitable pharmaceutically-active substances include: antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) llb/llla inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes—dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6a-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (inaperturethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; antisense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); silver compound and protease inhibitors.

In some embodiments, the active pharmaceutical substance is selected from the group consisting of amino acids, anabolics, analgesics and antagonists, anaesthetics, anti-adrenergic agents, anti-asthmatics, anti-atheroscleroticss, antibacterials, anticholesterolics, anti-coagulants, antidepressants, antidotes, anti-emetics, anti-epileptic drugs, antifibrinolytics, anti-inflammatory agents, antihypertensives, antimetabolites, antimigraine agents, antimycotics, antinauseants, antineoplastics, anti-obesity agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and neurotrophins, osmotic diuretics, parasympatholytics, para-sympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, saccharides, polysaccharides, glycoproteins, hyaluronic acid, and any excipient that can be used to stabilize a proteinaceous therapeutic.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

What is claimed is:

1. A pneumostomy technique used to create a pneumostoma through a chest wall, parietal membrane and visceral membrane into a lung of a patient, wherein:
    the pneumostomy technique comprises a first procedure, an interval and a second procedure;
    the first procedure comprises,
    (1a) accessing the parietal membrane by making an incision in the chest wall and exposing a localized region of the parietal membrane without puncturing the parietal membrane; and
    (1b) treating the localized region of said parietal membrane to induce a pleurodesis without puncturing the parietal membrane;
    the interval comprises a waiting period between the first procedure and the second procedure in order to allow the pleurodesis to form; and
    the second procedure comprises,
    (2a) identifying the position of the localized region,
    (2b) verifying that a pleurodesis has been formed between the parietal and visceral membranes within the localized region,
    (2c) making an incision through parietal and visceral membranes within the localized region and pleurodesis,
    (2d) inserting a distal end of a pneumostomy catheter through the incision into the lung such the distal end of the pneumostomy catheter is embedded within parenchymal tissue of the lung,
    (2e) expanding an expandable device at the distal end of the pneumostomy catheter to displace parenchymal tissue surrounding the distal end of the pneumostomy catheter for creating a cavity in the parenchymal tissue and securing the pneumostomy catheter within the lung,
    (2f) applying tension to the pneumostomy catheter to draw the lung towards the incision;
    (2g) after the lung is drawn toward the incision, securing the pneumostomy catheter to the chest wall of the patient thereby stabilizing the incision during healing of the pneumostoma;
    (2h) leaving the distal end of the pneumostomy catheter embedded in the parenchymal tissue to create the pneumostoma;
    (2i) collapsing the expandable device at the distal end of the pneumostomy catheter;
    (2j) removing the pneumostomy catheter from the patient after formation of the pneumostoma, wherein the pneumostoma includes an artificial channel connecting the cavity in the parenchymal tissue created by the pneumostomy catheter to the air external to the patient's body; and
    (2k) inserting a pneumostoma management device into the pneumostoma to protect the pneumostoma and maintain patency of the pneumostoma, wherein the pneumostoma management device has a different structure than the pneumostomy catheter.

2. The pneumostomy technique of claim 1, wherein the first procedure is performed as an outpatient procedure and without the use of general anesthetic.

3. The pneumostomy technique of claim 1, wherein the expandable device at the distal end of the pneumostomy catheter is a balloon which is connected by a tube to a coupling at a proximal end of the pneumostomy catheter and wherein step (2e) comprises:
    (2e) operating a syringe connected at the proximal end of the pneumostomy catheter to introduce a fluid through the tube into the balloon thereby expanding the balloon at the distal end of the pneumostomy catheter to displace parenchymal tissue of the lung and secure the pneumostomy catheter within the lung.

4. The technique of claim 1 wherein the interval is one or more days.

5. The technique of claim 1, wherein step (2h) of the second procedure comprises leaving the distal end of the pneumostomy catheter embedded in the parenchymal tissue for one to two weeks to create the pneumostoma.

6. A surgical technique used to create a pneumostoma through a chest wall, parietal membrane and visceral membrane into a lung of a patient, wherein:
    the surgical technique comprises a first procedure, an interval and a second procedure;
    the first procedure comprises,
    (1a) accessing the parietal membrane by making an incision in the chest wall and exposing a localized region of the parietal membrane without puncturing the parietal membrane; and
    (1b) treating the localized region of said parietal membrane to induce a pleurodesis without puncturing the parietal membrane;
    the interval comprises a waiting period between the first procedure and the second procedure in order to allow the pleurodesis to form; and
    the second procedure comprises,
    (a) identifying the position of the localized region,
    (b) verifying that a pleurodesis has been formed between the parietal and visceral membranes within the localized region,
    (c) inserting a distal end of a pneumostomy catheter into the lung through the chest wall, parietal membrane and visceral membrane within the localized region such the distal end of the pneumostomy catheter is embedded within parenchymal tissue of the lung,
    (d) expanding an expandable component attached to the distal end of the pneumostomy catheter to displace parenchymal tissue surrounding the distal end of the pneumostomy catheter for creating a cavity in the parenchymal tissue and securing the distal end of the pneumostomy catheter within the lung;
    (d1) applying tension to the pneumostomy catheter to draw the expandable component towards the incision;
    (d2) after the expanded component is drawn toward the incision, securing the pneumostomy catheter to the chest wall of the patient thereby stabilizing the pneumostoma during healing;
    (e) leaving the distal end of the pneumostomy catheter embedded in the parenchymal tissue to create the pneumostoma;
    (f) collapsing the expandable component at the distal end of the pneumostomy catheter;
    (g) removing the pneumostomy catheter from the patient after formation of the pneumostoma, wherein the pneumostoma includes an artificial channel connecting the cavity in the parenchymal tissue created by the pneumostomy catheter to the air external to the patient's body; and
    (h) inserting a pneumostoma management device into the pneumostoma to protect the pneumostoma and maintain patency of the pneumostoma, wherein the pneumostoma management device has a different structure than the pneumostomy catheter.

7. The surgical technique of claim 6, wherein the first procedure is performed as an outpatient procedure and without the use of general anesthetic.

8. The surgical technique of claim 6, wherein the expandable component at the distal end of the pneumostomy catheter is a balloon and wherein step (d) comprises inflating the balloon with a fluid to displace parenchymal tissue of the lung and secure the pneumostomy catheter within the lung.

9. The surgical technique of claim 6 wherein:
the first procedure includes the additional step of depositing adjacent the localized region a marker which may be visualized external to the patient; and
step (a) of the second procedure comprises locating the localized region by locating the marker from external to the patient.

10. The surgical technique of claim 6 wherein:
the first procedure includes the additional step of depositing adjacent the localized region a radiopaque marker; and
step (a) of the second procedure comprises locating the localized region by locating the radiopaque marker using x-rays.

11. The technique of claim 6 wherein the interval is one or more days and the leaving step (e) is one or more days.

12. The technique of claim 6, wherein step (e) of the second procedure comprises leaving the distal end of the pneumostomy catheter embedded in the parenchymal tissue for more than one week to create the pneumostoma.

13. A surgical technique used to create a pneumostoma through a chest wall, parietal membrane and visceral membrane into a lung of a patient comprising:
an outpatient procedure to create a localized pleurodesis;
an interval of one or more days between the outpatient procedure and before an inpatient procedure, wherein the inpatient procedure creates a pneumostoma,
the inpatient procedure comprising
introducing a distal end of a pneumostomy catheter into parenchymal tissue of the lung through the chest wall, parietal membrane and visceral membrane, and within the localized pleurodesis,
expanding the distal end of the pneumostomy catheter within the parenchymal tissue of the lung thereby displacing the parenchymal tissue of the lung in order to urge the parenchymal tissue of the lung towards the localized pleurodesis and after the parenchymal tissue of the lung is adjacent to the localized pleurodesis securing the pneumostomy catheter to the chest wall,
leaving the distal end of the pneumostomy catheter embedded in the parenchymal tissue to create the pneumostoma,
removing the pneumostomy catheter after a period of three or more days to expose the pneumostoma, and
inserting a pneumostoma management device into the pneumostoma to protect the pneumostoma and maintain patency of the pneumostoma, wherein the pneumostoma management device has a different structure than the pneumostomy catheter.

14. The surgical technique of claim 13, wherein the distal end of the pneumostomy catheter comprises a balloon and the step of expanding the distal end of the pneumostomy catheter includes inflating the balloon.

15. The surgical technique of claim 13, wherein the outpatient procedure to create the localized pleurodesis further comprises introducing a radiopaque marker to identify the location of the pleurodesis.

* * * * *